(12) United States Patent
Nishio

(10) Patent No.: US 7,388,100 B2
(45) Date of Patent: Jun. 17, 2008

(54) TERTIARY AMINE COMPOUNDS

(76) Inventor: Tetsuya Nishio, 2-4-6-404, Funabori, Edogawa-ku, Tokyo (JP)

( * ) Notice: Subject to any disclaimer, the term of this patent is extended or adjusted under 35 U.S.C. 154(b) by 0 days.

(21) Appl. No.: 11/295,925

(22) Filed: Dec. 7, 2005

(65) Prior Publication Data

US 2006/0145145 A1 Jul. 6, 2006

(51) Int. Cl.
*C07D 209/08* (2006.01)
(52) U.S. Cl. .................................... 548/469
(58) Field of Classification Search ............... 548/469, 548/455
See application file for complete search history.

(56) References Cited

U.S. PATENT DOCUMENTS 5,368,966 A * 11/1994 Nakamura et al. ......... 430/58.5

OTHER PUBLICATIONS

Caplus RN 848942-96-1.*

Labadie et al. Indol-2-yltributylstannane: A Versatile Reagent for 2-Substituted Indoles *J. Org. Chem.* 59(15):4250-4254 (1994).

K. Ziemelis "Putting It On Plastic", *Nature* 393:619620 (1998).

Koezuka et al. "Polythiophene Field-Effect Transistor With Polypyrrole Worked as Source and Drain Electrodes", *Appl. Phs. Lett. Am. Inst. Phys.* 62(15:)1794-1796 (1993).

* cited by examiner

*Primary Examiner*—Joseph McKane
*Assistant Examiner*—Shawquia Young
(74) *Attorney, Agent, or Firm*—Myers, Bigel, Sibley & Sajovec, P.A.

(57) ABSTRACT

An object of the present invention is to provide an organic semiconductor device comprising a semiconductor layer containing a compound with improved cohesive force, controllable molecular orientation, high packing property, high overall electrical conduction, high durability and high time-dependent stability. The present invention provides; a tertiary amine compound represented by formula (1); an organic semiconductor device comprising a substrate; a gate electrode; source and drain electrodes; and a semiconductor layer, wherein the semiconductor layer contains the tertiary amine comuound represented by formula (1).

5 Claims, 2 Drawing Sheets

- CATHODE ELECTRODE (LiO$_2$, Ag, ITO)
- EMISSIVE LAYER
- HOLE TRANSPORT LAYER
- SURFACE MODIFICATION LAYER
- ANODE ELECTRODE (Cr)
- SUBSTRATE

- CATHODE ELECTRODE (LiO$_2$, Ag, ITO)
- EMISSIVE LAYER
- HOLE TRANSPORT LAYER
- ANODE ELECTRODE (Cr)
- SUBSTRATE

TERTIARY AMINE COMPOUNDS

BACKGROUND OF THE INVENTION

1. Field of the Invention

The present invention relates to a tertiary amine compound, and an organic semiconductor device and organic electroluminescence device using the compound.

2. Description of Related Art

Organic semiconductor devices typically have a gate electrode, an insulating layer stacked on/above the gate electrode, a source electrode and a drain electrode formed on/above the insulating layer, and a semiconductor layer of an organic compound interposed between the source electrode and drain electrode. The semiconductor layer is formed by the vapor deposition method, application method, drop encapsulation method, vacuum encapsulation method or the like. Organic semiconductor materials suited for respective film forming methods and excellent in current voltage efficiency and length of life are under investigation. Owing to ease of the formation of a semiconductor layer, organic semiconductor devices have advantages such as low cost and mass productivity in a short time.

Such organic semiconductor devices using an organic compound and available at a lost cost can be classified into three groups, that is, low molecule type, polymer type and liquid crystal type.

First, as a polymer type, Appl. Phys. Lett., 62, 1794(1993) describes that organic semiconductor devices using polythiophene, polypyrrole and the like are described. These polymer types are excellent in mass productivity because semiconductor layer can be formed by the application method. In the polymer type organic semiconductor device, however, a polymer is used for the formation of a semiconductor layer between a source electrode and a drain electrode. The polymer has a short life and has higher electrical resistance than a low molecule.

Appl. Phys. Lett., 63, 1372(1993) describes that polythiophene is used frequently as a semiconductor layer in the polymer type. Polythiophene is sparingly soluble in a solution and in addition, owing to heating at high temperature while using a solution of a strong acid such as hydrochloric acid, it tends to cause corrosion of electrodes or deterioration of device performance. It is therefore inferior in mass productivity and device reliability.

Secondly, as a low molecule type, an organic semiconductor device using pentacene is under investigation. It has, however, been generally pointed out as a problem that in this device, an excess voltage must be applied to a gate electrode because a current running between a source electrode and a drain electrode is inevitably small, which results in a drastic increase in a consumed power and in addition, tends to cause dielectric breakdown of an organic film. It burdens an external IC and in addition, makes circuit design difficult, which leads to a cost increase of the IC and deterioration in mass productivity. Also from the viewpoint of performance, the device becomes unstable and has reduced reliability. As a further problem which is expected to occur, the external IC will require a high level and complex circuit design in order to overcome the excessive current flow.

Moreover, pentacene is a low molecular weight compound so that when it is crystallized after vapor deposition, a crystallized portion may presumably become a nucleus of dielectric breakdown. A deposited film of pentacene has many pores so that a uniform film cannot be formed. The semiconductor layer formed using it has a low strength, which lowers the reliability of the device.

As described above, low molecular weight compounds (such as pentacene) used so far for organic semiconductor devices have a problem that a current hysteresis relative to a drive voltage is large. They also have a problem in time-dependent stability, and reliability against impact.

Thirdly, as the liquid crystal type, Appl. Phys. Lett., 73, 1595(1998) describes that organic semiconductors are manufactured by aligning smectic liquid crystals or discotic liquid crystals with an alignment layer formed by an alignment film.

Smectic liquid crystals are rod-like molecules so that they lack in alignment stability and in turn reliability. In addition, liquid crystals are insulators and have high electrical resistance so that the application of a voltage to such semiconductors does not cause smooth current flow, which results in poor switching performance. This increases a load to an external IC and at the same time, may destroy the circuit by much heat generated by high electrical resistance of the materials. As a result, the resulting semiconductor devices have poor mass productivity and reliability.

Many heterocyclic compounds such as thiophene and pyrrole to be ordinarily used for liquid-crystal organic semiconductor devices have a chemical structure not permitting easy packing, have high electrical resistance and lack in durability.

Discotic liquid crystals are disc-shaped molecules. Their molecules pack in the form of columns but difficulty in conjugation results in deterioration in performance related to electrical conduction performance, response and stability.

Such liquid crystals used for liquid-crystal type organic semiconductor devices tend to become nematic by a temperature increase at the starting time of operation so that the packing effect cannot be exhibited fully. Even in smectic liquid crystals, conduction in the direction of their main chain can only be used. Since they are low molecular weight liquid crystals, the conduction mechanism in the main chain cannot be used, resulting in deterioration of the conduction performance of the liquid crystal type organic semiconductor device and conduction performance by the electric field effect.

Most of liquid crystal compounds existing at present are ion conductive type and their response time is slow. Transfer of ions by themselves and accumulation on an electrode on one side leads to deterioration of the device performance. There is accordingly a demand for low-molecular weight organic compounds with which a semiconductor layer can be formed by vapor deposition or injection while making use of the packing effect of them as low molecular weight compounds and have good packing property.

SUMMARY OF THE INVENTION

With a view to overcoming the above described problems, the invention has been made. A first object is to provide an organic semiconductor device comprising a semiconductor layer containing a compound capable of improving the cohesive force and controlling molecular orientation, and having high packing property, high overall electrical conduction, and also high durability and time-dependent stability.

A second object of the invention is to provide a compound having improved electrical conduction and voltage response as well as the properties as described in the first object, and an organic semiconductor device and organic electroluminescence device, each comprising a semiconductor layer containing the compound.

In the invention, there is thus provided a tertiary amine compound represented by the following formula (1):

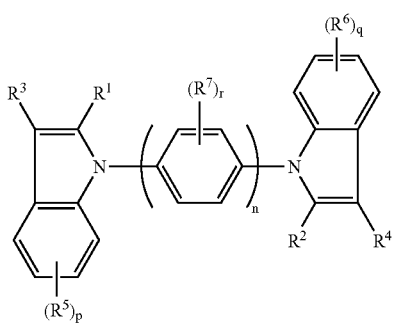

(1)

wherein n stands for an integer of from 1 to 6, p, q and r each stands for an integer of from 0 to 4; $R^1$ and $R^2$ each independently represents a group containing an aromatic ring and/or a heterocycle, $R^3$ and $R^4$ each independently represents a hydrogen atom or a $C_{1-20}$ alkyl group, and $R^5$, $R^6$ and $R^7$ each independently represents or a $C_{1-20}$ alkyl group. p, q and r represent the number of $R^5$, $R^6$ and $R^7$, respectively, which can substitute one to four hydrogen atoms of the respective ring.

In another aspect of the invention, there is also provided a metal complex containing the tertiary amine compound as a ligand.

In a further aspect of the invention, there is also provided an organic semiconductor device comprising a substrate, a gate electrode, a gate insulating layer, source and drain electrodes, and a semiconductor layer, said semiconductor layer comprising the above-described tertiary amine compound.

In a still further aspect of the invention, there is also provided an organic electroluminescence device comprising a substrate, a cathode electrode, an emissive part and an anode electrode, said emissive part comprising the tertiary amine compound.

According to the invention, it is possible to obtain a tertiary amine compound having a high packing property, excellent in overall electrical conduction and voltage response because hopping conduction occurs efficiently, and having high durability and time-dependent stability.

In addition, according to the invention, it is possible to obtain a tertiary amine compound having improved electrical conduction and voltage response, and an organic semiconductor device and organic electroluminescence device, each comprising a semiconductor layer containing the tertiary amine compound.

DETAILED DESCRIPTION OF PREFFERED EMBODIMENTS

Figure 1:
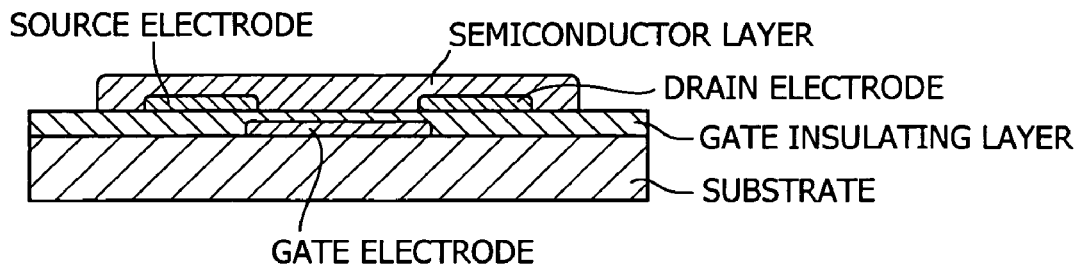
FIG. 1 is a cross-sectional view illustrating one example of the organic semiconductor device of the invention.

The tertiary amine compound of the invention has, as a basic structure, a tertiary amine compound represented by the following formula (1'):

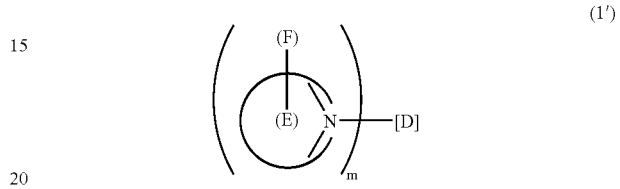

(1')

wherein N represents a nitrogen atom; a bond unit (E) binds with a bond unit [D] via a nitrogen atom in the bond unit (E); the bond unit (E) forms a covalent bond with a bond unit (F); the bond unit (E) represents an aromatic heterocyclic compound group composed of a skeleton structure other than a carbazole derivative and imide derivative and having no substituent or one or more substituents; the bond unit (F) represents an aryl or aromatic heterocyclic compound group having no substituent or one or more substituents; the bond unit [D] represents an aromatic ring compound group or aromatic heterocyclic compound group having no substituent or one or more substituents; and m stands for an integer of 1 or greater, with the proviso that when m stands for an integer of 2 or greater, the bond units (F) may be the same or different and the bond units (E) may be the same or different.

In the formula (1'), a bond unit—which is an electron donating (donor) bond unit apt to cause intermolecular overlapping (packing) of π electrons, in other words, a group more electron donative (a group tending to generate an acceptor, that is, a hole) than the bond unit (E) or (F) of the end group connected to a nitrogen atom, is therefore capable of improving the packing property owing to an interaction between intramolecular donor and intramolecular acceptor (charge transfer interaction or Van der Waals force), and moreover is three-dimensionally rotatable relative to a bond axis—is placed as the bond unit [D] existing at the center and connected to a nitrogen atom. This enables improvement in the packing property, resulting in improvement in molecular orientation.

In addition, in the tertiary amine compound represented by the formula (1'), a semiconductor layer, an emissive layer or a hole injection layer with excellent time-dependent stability can be formed by placing an intramolecular donor and intramolecular acceptor in the end groups (that is, the bond unit (E) and bond unit (F)), thereby heightening the intermolecular cohesive force. At the same time, electrons transfer easily in the end groups so that the electrical conduction of the above-described layer can be improved.

The amorphous property is also heightened by binding the bond unit (E) having almost a flat structure (which will hereinafter be called "quasi-planar structure") with the bond unit (F) having the different bond axis from that of the unit (E) in the end group, the bond unit being three-dimensionally rotatable around the bond axis. It becomes possible to form a semiconductor layer which does not crystallize easily and is excellent in time-dependent stability.

A tertiary amine compound represented by the following formula (2) to a tertiary amine compound represented by the following formula (11) have a similar effect to that of the tertiary amine compound of the formula (1') because they have a similar structure to that of the tertiary amine compound of the formula (1').

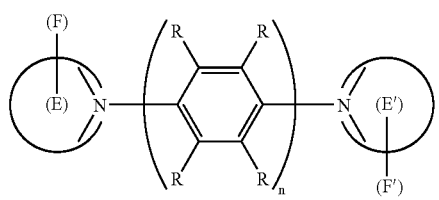

(2)

wherein N represents a nitrogen atom; a bond unit (E) or a bond unit (E') each binds, via a nitrogen atom in the respective bond unit, to a phenylene group having no substituent or one or more substituents; the bond unit (E) forms a covalent bond with a bond unit (F), and the bond unit (E') forms a covalent bond with a bond unit (F'); the bond unit (E) and bond unit (E') each represents an aromatic heterocyclic compound group having no substituent or one or more substituents; the bond unit (F) and the bond unit (F') each represents an aryl or aromatic heterocyclic compound group having no substituent or one or more substituents; Rs each independently represents a substituent; and n stands for an integer of 1 or greater.

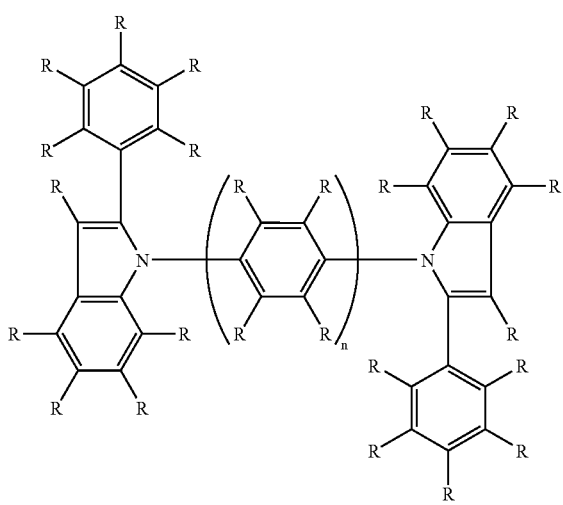

(11)

wherein Rs each independently represents a substituent; and n stands for an integer of 1 or greater.

In the tertiary amine compound of the formula (1') to a tertiary amine compound represented by the following formula (5):

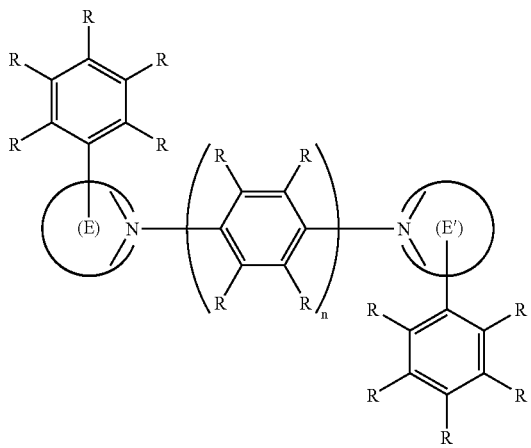

(5)

{wherein N represents a nitrogen atom; a bond unit (E) and a bond unit (E') bind, via a nitrogen atom in the respective bond units, with a phenylene group having no substituent or one or more substituents; the bond unit (E) and bond unit (E') each binds with a phenyl group having no substituent or one or more substituents; the bond unit (E) and bond unit (E') each represents an aromatic heterocyclic compound group having no substituent or one or more substituents; Rs each independently represents a substituent, and n stands for an integer of 1 or greater}, the bond unit (E) and bond unit (E') are each defined to be a compound other than a carbazole derivative and imide derivative (maleimide derivative or the like), because oxygen which binds with carbon contained in the imide derivative deactivates the electrical conduction (contribution of d electrons of ITO, if any, improves electrical conduction, but electrical conduction is deactivated when p electrons contribute to the bond). The bond unit (E) and bond unit (E') such as those containing oxygen (particularly containing a double bond of oxygen and carbon) are omitted even if they are not imide derivatives. In addition, carbazole derivatives are also omitted from the bond unit (E) and bond unit (E') because they have a low polarizing property and have a chemical structure not permitting easy formation of intramolecular donor and acceptor. Use of the tertiary amine compound of the invention for the formation of a semiconductor layer therefore enables improvement of electrical conduction and charge mobility.

Owing to increased overlapping of wave functions of conjugated π electrons between the molecules of the tertiary amine compound of the invention (improvement in the packing performance), the hopping conductivity between the molecules is improved, resulting in high electrical conduction performance and moreover, decrease in a current/voltage load. Consequently, a heat generated in the device (organic semiconductor device and/or organic electroluminescence device) decreases when the electric field is switched on, which reduces the heat-induced damage to the device, thereby improving the reliability of the device. In addition, a voltage load or current load to an externally driven IC decreases, which facilitates designing of the externally driven IC and enables the production at a low cost. This leads to improvement in mass productivity.

In the tertiary amine compound represented by the formula (1'), at least two end groups are bridged via the bond unit [D] so that molecular vibration due to heat does not occur frequently (bridge effect). In addition, orientation of the functional groups is stabilized by the central bond unit [D] which easily causes packing because of its stereostructure. This improves the intermolecular packing, lessens the voltage-induced variations in electrical conduction and makes it possible to provide an organic semiconductor device having excellent current and voltage stability. Moreover, functional groups of the end groups on the quasi-planar structure are bridged by the bond unit [D] so that the arrangement of the end groups is not disturbed and maintained even at a high temperature. This realizes the use of the compound over a wide temperature range.

Even if a central substituent rotates and molecular vibration is induced by the electrical field, free rotation of the molecule relaxes the vibration and molecular orientation instantly occurs. This improves stability of the intermolecular packing, lessens the voltage-induced variations in electrical conduction and makes it possible to provide an organic semiconductor device having excellent current and voltage stability.

In short, the glass transition point (Tg) of the tertiary amine compound increases by the effect of cross-link (bridge) and cohesive force of an intramolecular donor and intramolecular acceptor, and improvement in durability of a film formed from the tertiary amine compound against the heat, voltage or current, the device improves reliability.

Prevention of Inversion of $sp^3$ Nitrogen Atom=Prevention of Shortening

As can be seen from the fabricated molecule model of a tertiary amine compound represented by the following formula (9):

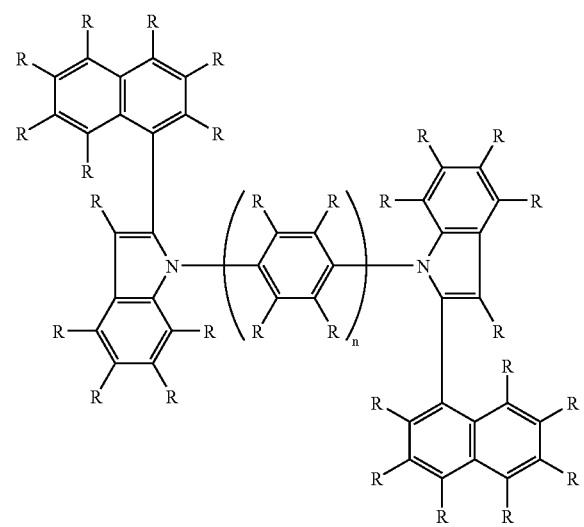

(9)

{wherein, Rs each independently represents a substituent and n stands for an integer of 1 or greater} and having a hydrogen atom as each of the substituents Rs and 2 as n, its stereostructure is complexly intertwined around the nitrogen atom. In particular, the hydrogen atom connected to the 8- or 8'-carbon of the naphthalene skeleton collides with the hydrogen atom connected to the 3-, 3'-, 5- or 5'-carbon atom of the benzene directly connected to the nitrogen atom in the divalent biphenyl group at the center. This causes inversion of the stereostructure found in $sp^3$ nitrogen. The above-described collision does not occur when the molecule model is fabricated using a tertiary compound represented by the following formula (7):

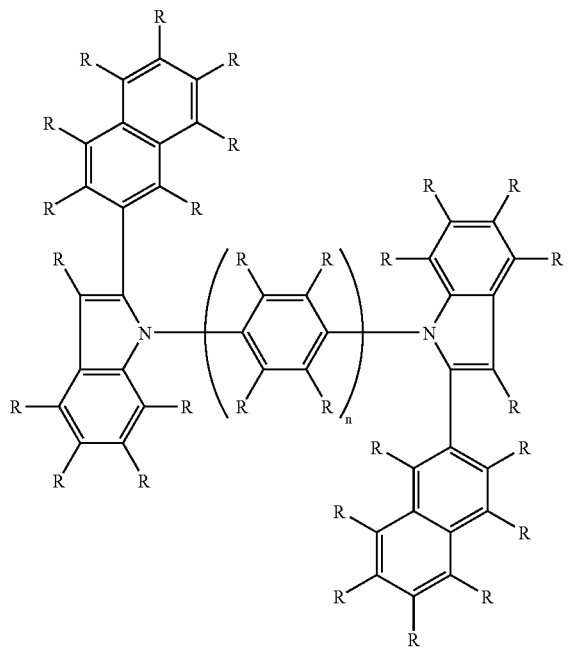

(7)

{wherein Rs each independently represents a substituent and n stands for an integer of 1 or greater) and having a hydrogen atom as each of the substituents R and 2 as n. As a result, inversion of the stereostructure found in $sp^3$ nitrogen can be prevented so that the device can improve reliability while overcoming the shortening phenomenon induced by the excessive voltage application.

In addition, the tertiary amine compound of the invention has improved cohesive force by the intermolecular action (charge transfer interaction or Van der Waals force) between an intramolecular acceptor and donor in the end groups. The film formed by the tertiary amine compound therefore has increased hardness, which lessens damage due to excessive voltage or external impact and attains both the device performance and life (reliability).

In short, it is possible to avoid turbidity (presumed to result from an increase in the intermolecular distance or inversion of a stereostructure due to crystallization) which is a time-dependent change as can often be found in a low molecular weight deposited film.

Effects of Incorporation of a Metal Compound

In the tertiary amine compound of the invention, a metal ion and/or a metal complex may be incorporated. Co-deposition of a metal complex, for example, causes packing of the ligand of the metal complex with the bond unit [D] at the center of the tertiary amine compound, which stabilizes, with the passage of time, the film formed by the tertiary amine compound and the metal complex (improves the stability of the film). This is presumed to owe to that a laminar compound is formed by the intercalation of the metal complex to the bond unit [D] at the center and the control of conformation of the bond unit [D] or end group controls turbidity (crystallization). The incorporation of a metal complex having phenylpyridine as a ligand in the tertiary amine compound of the invention, particularly in the case where the ligand is phenylpyridine and the bond unit [D] at the center of the tertiary amine compound is biphenyl, tends to cause intermolecular packing because of a similar stereostructure between them. This brings about improvement in reliability. A metal complex in which the metal is surrounded spherically by ligands forms a laminar compound with the end group of the tertiary amine compound having a quasi-planar structure so that the film has improved stability. Since a metal ion has a structure capable of forming a laminar compound between the end group and the metal, use of it also improves reliability.

Guideline for Designing of the Present Material

The tertiary amine compound of the invention has a divalent biphenyl group, naphthyl group or the like and therefore is properly steric with a quasi-planar structure, and in addition, contains a skeleton structure facilitating mutual packing so that with substantially no deviation in a plane direction and no gap, it is superior in electrical conduction to an ordinary single planar molecule.

Generation Mechanism of an Intramolecular Donor and Acceptor and Intramolecular Polarization In molecules having an aromatic ring but different in chemical structure, the time necessary for transfer of a conjugated bond and charging of carbon atoms just below the bond portion differs, depending on their structure, which leads to difference in the electron attracting property in the molecule. This results in intramolecular polarization. Portions having a longer conjugated bond have a stronger electron attracting property. Accordingly, when three connected groups of the tertiary amine compound are different from each other, packing property is improved by the intramolecular polarization, which heightens cohesive force among molecules and improves the film durability. The above-described advantage is utilized in the invention.

Improvement 1 of Stability in Stereostructure

It is generally known that a tertiary amine compound emits fluorescence and $sp^3$ nitrogen is a recombination center. It becomes $sp^2$ when the nitrogen forms a polaron with an aromatic ring. There is however a possibility of its stereostructure being inverted upon re-conversion from $sp^2$ to $sp^3$. Even partial inversion of the stereostructure destroys the charge transfer complex of the film and causes dotted turbidity (crystallization), which is presumed to lead to deterioration in electrical conduction and reliability (shortening of the life due to an increase in resistance). An end group having high steric hindrance such as naphthyl group is therefore introduced into the tertiary amine to improve its dielectric strength or time-dependent stability.

Improvement 2 of Stability in Stereostructure

As documents or the like suggest, devices composed of a low molecular weight material with high planarity have higher brightness but shorter life than ordinary light emitting devices composed of a low molecular weight material with a complex stereostructure. This means that, compared with a molecule with higher planarity, a molecule having a complex stereostructure has higher resistance but is superior in stability. In short, a film composed of a low molecular weight material having a complex stereostructure becomes stable, because almost all the structures of the charge transfer complex are maintained stably. In the tertiary amine compound, the three-dimensional rotation of the respective aromatic rings connected to the nitrogen atom of the tertiary amine compound causes complex intermolecular packing, which controls steric inversion peculiar to the $sp^3$ structure which will otherwise occur in the nitrogen atom of the tertiary amine compound; and a complex stereostructure controls molecular vibration to be transmitted from molecule to molecule by the thermal vibration and along with the intramolecular polarization effect stabilizes the structure of charge transfer complex, thereby stabilizing the film. The invention makes use of the tertiary amine compound having such a property. Accordingly, the chemical structure has a great influence on the structural stability of the charge transfer complex.

Improvement of Electrical Conduction by Intramolecular Polarization

In the tertiary amine compound of the invention, groups connected to the nitrogen atoms of the tertiary amine are different from each other, which leads to difference in their electron donating properties. Since transfer of electrons from electron donating group to electron withdrawing group heightens the possibility of collision between electrons and holes, recombination tends to occur and besides, shortage of both electrons and holes facilitates charge transfer. This increases the mobility of charges, improves the response time of a semiconductor device and reduces a drive voltage.

For example, in the case of a tertiary amine compound represented by the formula (7) in which an electron donating group (indolyl group) is connected to an electron withdrawing group (naphthyl group), they promote intramolecular electron conduction and forms the current flow. As if air is withdrawn toward a water flow having a high flow rate, electrons are supplied from the internal bond unit [D] to an acceptor capable of forming a stable electron state. In other words, holes are formed in the functional group (such as divalent biphenyl group) of the bond unit [D] by the withdrawal of electrons.

A device composed of a low molecular weight compound with high planarity such as the tertiary amine compound of the invention has remarkably low resistance compared with a device composed of a low molecular weight compound having a complex stereostructure. It can easily be imagined that excellent packing performance and good electrical conduction can be attained by planar packing. A stereostructure having too high planarity however lowers reliability because of separation of packing due to molecular vibration. In the invention, a functional group with a quasi-planar structure is employed as the end group in consideration of the above-described balance so that a device with improved electrical conduction and high reliability can be manufactured. The tertiary amine compound of the invention has a higher molecular weight than pentacene ordinarily employed for manufacturing an organic semiconductor device so that a glass-transition temperature increases and as a result, the device has improved reliability.

Improvement of Electrical Conduction

As can be found from the molecular model fabricated using, for example, the tertiary amine compound represented by the formula (7) in which Rs each independently represents a hydrogen atom and n stands for 2, the divalent biphenyl group in the bond unit [D] at the center and the naphthalene portion at the periphery in the end group get closer to each other or each of two benzene portions in the bond unit [D] and the indole portion in the end group get closer to each other. In particular, the 8-carbon of the naphthyl group gets closest to the 3-, 3'-, 5- or 5'-carbon of the biphenyl in the bond unit [D] at the center directly connected to the nitrogen atom so that hopping conduction of electrons occurs in the molecule from the naphthyl group to the biphenyl. This contributes to charge elimination (no fluorescence is however emitted at this time) of holes of the biphenyl with electrons and as a result, the charges of the end group are consumed, which causes charge deficiency and improves electrical conduction by just that much.

Resolution of the Problem of Hysteresis

The substituent at the end group is a large group with a planar structure so that molecular vibration due to heat or voltage is small and has a small influence (hysteresis) on the history of voltage application to the device. Malfunctions of the device caused by repeated operations are reduced and as a result, the device has improved reliability (device life).

Film Hardness

A description will next be made of a change in film hardness when the end group or center group of the tertiary amine is changed. A difference in the end group of the tertiary amine leads to a difference in cohesive force due to a difference in the intensity between the intramolecular acceptor and intramolecular donor, which in turn appears as a difference in hardness. In other words, in the molecule of the tertiary amine compound asymmetric in the end group, the intramolecular donor and intramolecular acceptor increase their own properties, resulting in improvement in cohesive force. A device with high reliability can therefore be manufactured. A co-deposition film with a tertiary amine compound containing a metal complex becomes a remarkably hard film and owing to good packing property, a film thus formed has high modulus of elasticity. This film is superior in time-dependent stability to a film composed alone of the tertiary amine compound. The hardness can be measured by a Vickers hardness tester and by setting the indentation thickness to 10% or less of the film thickness, the hardness can be measured while reducing the error due to influence of a film thickness.

End Group and Change in Cohesive Force

Owing to the above-described reasons, the tertiary amine compound of the invention has higher cohesive force and a device with high stability can be manufactured when the end group connected to the nitrogen atom is more asymmetric. In other words, the asymmetric structure of the end group as is leads to formation of a donor structure portion and an acceptor structure portion in the molecule and the cohesive force between molecules increases by the intermolecular force between the donor and acceptor.

Resistance of Each Tertiary Amine Compound

As can be found from a molecule model fabricated by the tertiary amine compound represented by the formula (7) in which substituents R each represents a hydrogen atom and n stands for 2, when the end group becomes large and bulky, the end group collides with the functional group at the center (typically, a hydrogen atom connected to the 3-, 3'-, 5'- or 5-carbon of the divalent biphenyl group) and the molecular motion is limited, leading to improvement in the dielectric strength. When a long chain group is introduced at the center, an influence of the collision between the naphthyl group in the end group and the functional group at the center on the vibration of the whole molecule decreases, leading to improvement in the breakdown strength.

It has also been understood that the resistance against voltage can be reduced by introducing, into the end group, a functional group having a great π-covalent bond such as naphthyl group. In the tertiary amine compound of the invention, the dielectric strength is raised and resistance is reduced by enlarging the size of the planar structure of the end group (the drive voltage of the semiconductor by field effect can also be reduced).

Of the tertiary amine compounds, those represented by the formulas (2) to (5), (7), (9) and (11), so-called triamine dimers, particularly produce the advantages of the invention. Triamine dimers producing the advantages of the invention more effectively are compounds having, at both ends of a rod-like molecule thereof, two molecules having an asymmetric heterocyclic structure and they are excellent in the intermolecular packing from the viewpoints of steric limitation of the molecule or intermolecular attractive force.

Triamine dimmers having a chemical structure permitting production of the advantages of the invention still more effectively are, supposing that each substituent is three-dimensionally rotatable, tertiary amine compounds (triamine dimmers) characterized in that in the molecular structure with highest symmetry, they are asymmetric with respect to a plane including a bond axis of the nitrogen and the bond unit [D] and a central axis of an $sp^3$ hybrid orbital electron cloud containing a non-conjugated electron pair of the nitrogen atom (like {N,N'-bis(3-methylphenyl)-N,N'-bis(phenyl)benzidine, commonly called "TPD"}; they have, as substituents thereof, a π-conjugate system aromatic compound or aromatic heterocyclic compound; and the hydrogen atom bonded to the carbon atom is not substituted by another atom or molecule.

Advantage Brought by Having the Naphthalene Skeleton in the Molecule (Improvement in Electrical Conduction)

The tertiary amine compounds capable of producing the advantages of the invention still more effectively are those represented by the formula (2), the following formula (3):

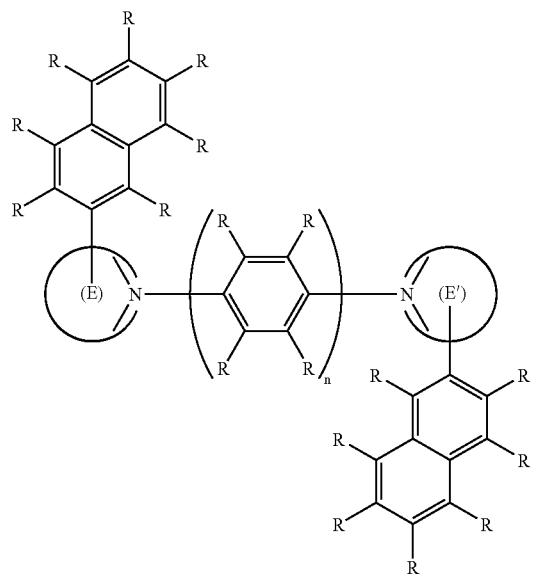

(3)

{wherein N represents a nitrogen atom; a bond unit (E) and a bond unit (E') are each bonded, via a nitrogen atom therein, to a phenylene group having no substituent or one or more substituents; the bond unit (E) and the bond unit (E') are each bonded to a 2-naphthyl group having no substituent or one or more substituents; the bond unit (E) and bond unit (E') each represents an aromatic heterocyclic compound group having no substituent or one or more substituent; Rs each independently represents a substituent, and n stands for an integer of 1 or greater}, the following formula (4):

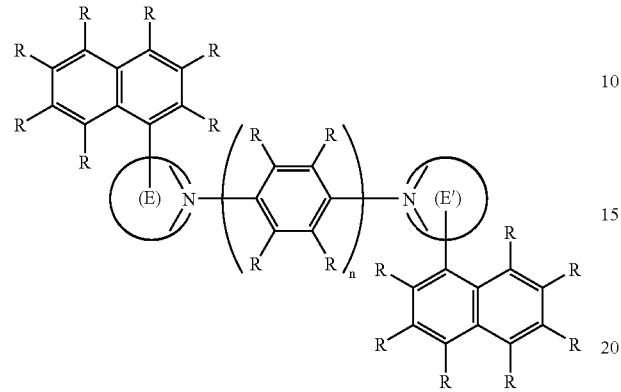

(4)

{wherein N represents a nitrogen atom; a bond unit (E) and a bond unit (E') are each bonded, via a nitrogen atom therein, to a phenylene group having no substituent or one or more substituents; the bond unit (E) and the bond unit (E') are each bonded to a 2-naphthyl group having no substituent or one or more substituents, the bond unit (E) and bond unit (E') each represents an aromatic heterocyclic compound group having no substituent or one or more substituents; Rs each independently represents a substituent; and n stands for an integer of 1 or greater}, the formula (7) and the formula (9). In short, compounds having a naphthalene skeleton in the side chain thereof have especially good electrical conduction (have low resistance) because low molecular weight compounds with a naphthalene skeleton in the side chain thereof form a charge transfer complex. A good semiconductor layer therefore easily forms a charge transfer complex.

The tertiary amine compound of the invention has, as the end group thereof, a functional group with a quasi-planar structure so that the end portion of the molecule is apt to be stacked in the column form while drawing a circle (so-called helix structure or double helix structure). When it has, in the side chain thereof, a naphthyl group, packing of the end groups of the two adjacent molecules occurs and it brings about improvement of hopping conductivity and also improvement of the electrical conduction in the axial direction of the column while drawing a circle (a macromolecule which is a steric molecule version of copper phthalocyanine is expected to be formed as a result of assembly of a plurality of the tertiary amine compounds of the invention), whereby high electrical conduction and decrease in the current/voltage load are attained. As a result, generation of heat decreases, the thermal damage to the film (semiconductor layer or the like) made of the tertiary amine compound decreases and the device has improved reliability. In addition, owing to a reduction in voltage load or current load to an externally driven IC, the IC can be produced at a low cost and mass productivity increases.

The tertiary amine compound constituting the semiconductor layer includes a structure having a function of an intramolecular acceptor (electron withdrawing group) and therefore causes intramolecular polarization. This improves a charge transport function and in turn, improves electrical conduction.

Improvement of Cohesive Force (Improvement of Durability)

The end group is a quasi-planar molecule and has a molecular structure inferior in symmetry so that intramolecular polarization occurs, leading to interaction (charge transfer interaction or Van der Waals force) between molecules (between end groups and between bond unit [D] and end group). For example, in the tertiary amine compound represented by the following formula (6):

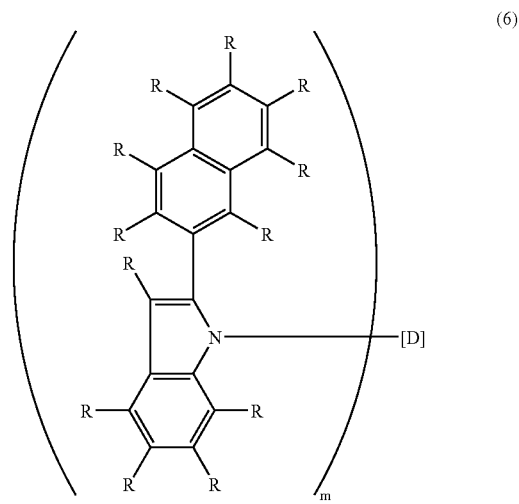

(6)

{wherein bond unit [D] represents a group composed of an aromatic ring compound group or aromatic heterocyclic compound group having no substituent or one or more substituents; Rs each independently represents a substituent; and m stands for an integer of 1 or greater} to the tertiary amine compound represented by the following formula (8):

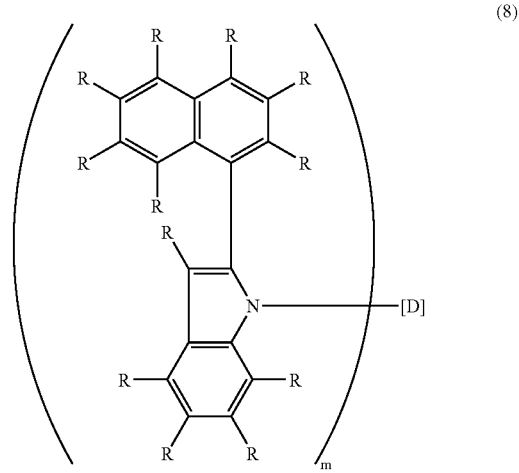

(8)

{wherein bond unit [D] represents an aromatic ring compound group or aromatic heterocyclic compound group having no substituent or one or more substituents, Rs each independently represents a substituent, and m stands for an integer of 1 or greater} and the tertiary amine compound represented by the formula (9), owing to a difference between an acceptor skeleton (naphthyl or the like group) and a donor skeleton (indolyl or the like group), asymmetry is formed relative to a plane including the bond axis of the nitrogen with the bond unit [D] and a central axis of the sp$^3$ hybrid orbital electron cloud containing a non-conjugated electron pair of the nitrogen atom. This asymmetry means not only that from the viewpoints of its structure but also that from the viewpoint of electron withdrawing property and electron donating property. In other words, the naphthyl group has a greater electron withdrawing property than the indolyl group and naphthalene is negatively charged, while indole is positively charged. Owing to the Van der Waals force caused by intramolecular polarization, alternate stacking (packing) tends to occur. During charge transfer, the charge transfer interaction occurs so that stacked packing is maintained and at the same time, electrical conduction is improved.

A Naphthalene-containing Low-molecular-weight Compound Tends to Form a Charge Transfer Complex and, in a Solvent Undergoes a Change into a Color of a Long Wavelength The low-molecular weight tertiary amine compound to which naphthalene has been bonded easily forms a charge transfer complex. As a result, a conjugate system spreads and the compound becomes brown in a solvent (xylene or the like). In other words, the naphthyl group in the end group has a cohesive force for improving the intermolecular packing. In the tertiary amine compound of the invention, incorporation of a chemical structure of naphthalene in the molecule which exists in the end group of the compound and has a planar structure heightens the cohesive force of the molecule, thereby improving the intermolecular packing property.

Advantage Brought by an Electrode Having a Surface Modification Layer

When a surface modification layer is formed on/above the electrode of the organic semiconductor device and/or organic electroluminescence device of the invention, it contributes to efficient charge transfer. The electrode having thereon a surface modification layer facilitates the withdrawal of charges from the surface polarized owing to magnetic anisotropy by utilizing the Lorentz force so that the electrode is not necessarily made of a metal having a high work function such as gold used for ordinary organic semiconductor devices but is made by the high temperature process which was conventionally thought to be impossible. This makes it possible to form the electrode with a metal having a small work function such as chromium. As a result, the electrode has high mass productivity and high reliability. When the electrode is formed by the high temperature process, migration of the surface modification layer to the electrode side can be prevented, making it possible to manufacture an organic semiconductor device or organic electroluminescence device with high reliability.

In the electrode having a surface modification layer, a substantial work function can be reduced. The surface modification layer can be subjected to treatment to form a lattice defect portion therein. It is also possible to remove defects by doping a metal compound into the lattice defect portion and at the same time, form a high-density doping layer locally in the surface portion as shallow as about several tens nm from the surface. As a result, injection of charges (holes or electrons) from the electrode to the semiconductor layer can be accelerated by the energy level of the impurity thus formed.

It is also possible to carry out treatment for intentionally controlling defects to orient elements. Local and regular vacant lattices can be formed in the surface portion as shallow as several tens nm from the surface of the surface modification layer. As a result, charge transfer from the electrode can be improved. For example, regular defects can be formed by irradiation of an argon ion to the surface modification layer, which means control of the orientation of atoms other than defects. As a result, charge injection to the semiconductor layer can be improved.

Uses

The above-described tertiary amine compounds (including dendrimers) are preferably used for semiconductor layers (including dendrimers for semiconductor layers) of organic semiconductor devices. They can also be used for phase difference polarization plates, solar cells, electromagnetic shielding materials, antistatic materials (antistatic agents used for optical films for liquid crystal display), batteries (electrode materials, electrolytes, conductive polymer gels), optical switches (color change switches), sensors, electrophotographic photoreceptors, photorefractive devices, condensers, diodes, transistors (including such as active substrates, integrated circuits and display devices, which comprises transistors), organic electroluminescence devices {(used as an electron transport layer, electron injection layer, emissive layer, hole transport layer, hole injection layer and host of phosphorescence emitting layer, each at an emissive part) (the organic electroluminescence device is used as a back light for liquid crystal display device, illumination, signal display device and the like)}, memories, nonlinear optical materials, optical logic devices, electric generating devices, liquid crystal conductors, liquid crystal magnetic materials, liquid crystal display devices, ICs, and pharmaceuticals (dendrimer preparations such as dendrimers for drug delivery system (DDS)}.

The tertiary amine compound and the organic semiconductor device using the compound, each according to the invention, will next be described specifically.

The unit (E) in the above-described formulas (1') to (5) is not limited but includes indole derivatives (such as derivatives of an indolyl group and derivatives of a benzo[g] indolyl, benzo[h]indolyl or benzo[f]indolyl group), purine derivatives (such as derivatives of a purinyl group), indazole (1H-indazole) derivatives (such as derivatives of an indazolyl group), imidazole derivatives (such as derivatives of an imidazolyl group), tetrazole derivatives (such as derivatives of a tetrazolyl group), pyrrolo[2,3-b]pyridine derivatives (such as derivatives of a pyrrolo[2,3-b]pyridyl group), pyrrolo[3,2-b]pyridine derivatives (such as derivatives of a pyrrolo[3,2-b]pyridyl group), indoline derivatives (such as derivatives of an indolyl group), 1H-naphtho[2,3-d]imidazole derivatives (such as derivatives of a 1H-naphtho[2,3-d]imidazolyl group), and 1,4-benzothiazine derivatives (such as derivatives of a 1,4-benzothiazyl group).

The unit (F) in the above-described formulas (1') and (2) is not limited but includes naphthalene derivatives (such as derivatives of a naphthyl group), naphthyridine (such as derivatives of a naphthyridinyl group), phthalazine derivatives (such as derivatives of a phthalazinyl group), quinoxaline derivatives (such as derivatives of a quinoxalinyl group), quinazoline derivatives (derivatives of a quinazolinyl group), cinnoline derivatives (such as derivatives of a cinnolinyl group), phenylpyridine derivatives (such as derivatives of a phenylpyridyl group), pteridine derivatives (such as derivatives of a pteridinyl group derivatives), benzene derivatives (such as derivatives of a phenyl group), pyridine derivatives (such as derivatives of a pyridyl group), pyrazine derivatives (such as derivatives of a pyrazinyl group), pyrimidine derivatives (such as derivatives of a pyrimidinyl group), pyridazine derivatives (such as derivatives of a pyridazinyl group), thiophene derivatives (such as derivatives of a thiophenyl group), pyridopyrimidine derivatives (such as derivatives of a pyridopyridinyl group), phenanthrene derivatives (such as derivatives of a phenanthryl group), isoquinoline derivatives (such as derivatives of an isoquinolinyl group), and tetraazanaphthalene derivatives (such as derivatives of a tetraazanaphthalinyl group).

How to Distinguish a Bond Unit Serving as an Intramolecular Donor from a Bond Unit Serving as an Intramolecular Acceptor A donor molecule and an acceptor molecule can easily be distinguished by the fluorescence wavelength of a conductive polymer in which the molecule is incorporated as a divalent group adjacent to fluorene as a copolymer of fluorene-based polymer. The fluorene-based polymer absorbs light mainly at its fluorene portion so that its wavelength is shorter than the fluorescence wavelength. The fluorescence wavelength however changes greatly owing to the electron withdrawing property of the divalent group connected to fluorene. In short, as the electron withdrawing property is greater, the fluorescence wavelength tends to shift to the longer wavelength side.

This is also apparent from the fact that the fluorene-based polymer shows almost a fixed absorption wavelength (about 380 nm) irrespective of the nature of the copolymer. This means that when fluorene has an electron withdrawing group as an adjacent group, it expands the electron orbital of LUMO (Lowest Unoccupied Molecular Orbital), thereby causing recombination with HOMO (Highest Occupied Molecular Orbital) in which the electron orbital has been distributed at the center of the fluorene portion. It is obvious that the biphenyl group, phenyl group and naphthyl group which are substituents of N,N'-di(naphthalene-1-yl)-N,N'-diphenyl-benzidine (which will hereinafter be abbreviated as "α-NPD") or N,N'-bis-(3-methylphenyl)-N,N'-bis-(phenyl)-benzidine (which will hereinafter be called "TPD") which is a typical low molecular weight material can be arranged as follows in order of decreasing strength of electron withdrawing property: naphthyl>phenyl>biphenyl.

It is presumed from the fluorescence wavelength that the degree of electron withdrawing property decreases in the following order: fluorene>naphthalene>carbazole>benzene>methylbenzene and biphenyl. Methylbenzene is presumed to be electron donative owing to the hyperconjugation effect of the methyl group. It is also presumed that elongation of the conjugate system energetically stabilizes the molecular orbital of electron, which heightens the electron withdrawing property.

In the case of fluorene having, as an adjacent group, thiazole having a remarkably strong electron withdrawing property, the electron orbital in the fluorene molecule is withdrawn by the thiazole group and as a result, in addition to LUMO (313 nm) of fluorene, another LUMO which is stable as a mixed orbital is formed by fluorene and thiazole, which newly generates absorption wavelength (443 nm) owing to electron transfer from HOMO of fluorene to thiazole LUMO. This means that owing to withdrawal of electrons from fluorene by thiazole, stable points of two LUMO electron orbitals are formed in the absorption wavelength.

Such an effect can be regarded as an influence of the splitting of the orbital of degenerate LUMO when it is presumed that at the fluorene portion, a similar effect to that in an external field occurs in the fluorene molecule owing to the electron withdrawing effect of thiazole and as a result, the effect resembling the Stark effect appears.

The splitting of fluorescence wavelength in the conductive polymer is observed mainly not in a solution but in a film so that there is a high possibility of recombination occurring between molecules, influenced by the formation of a conjugated π electron system excimer between molecules. In other words, appearance of two fluorescence wavelengths owes to existence of two recombination mechanism, that is, a recombination mechanism in which electrons return to fluorene and a recombination mechanism due to intermolecular hopping conduction.

Based on the above-described viewpoints, degree of the electron withdrawing property of each molecule can be judged. In short, the greater a difference between absorption wavelength and fluorescence wavelength, the stronger the electron withdrawing property (acceptor property).

The tertiary amine compounds of the invention will next be explained in detail by making use of the above-described finding.

The tertiary amine compounds of the invention each has, in the molecule thereof, two end functional groups having a quasi-planar structure and has, between these groups, an electron donative divalent biphenyl group excellent in orientation property via a nitrogen atom serving as a switch for separating holes and electrons so that overlapping of wave functions in the conjugated π-electron system between molecules becomes large (meaning improvement in packing property).

Such a low molecular weight organic material having a chemical structure capable of forming, in the molecule thereof, a donor and acceptor is excellent in arrangement. For example in copper phthalocyanine, the alignment property as a whole molecule is improved because copper becomes a positive ion and the centers of the molecules are arranged in the columnar form. This is also apparent from the existence of copper phthalocyanine in many crystal forms. This is presumed to improve the arrangement, increase the overlapping of wave functions of the conjugated π-electron systems between molecules (improve packing property) and facilitate the intermolecular hopping conduction. The copper phthalocyanine is therefore popularly used as an electron material. Nitrogen atoms around copper serve as a switch for separating the holes in copper and electrons in the surrounding aromatic group. As a result, it reduces an annihilation probability of electrons and holes, thereby extending their lifetime. The recombination is presumed as a phenomenon occurring only in electrons and holes having a long lifetime.

Based on the above-described results on the fluorene polymer showing that a luminous phenomenon occurs by filling holes generated in the fluorene with electrons of an adjacent connecting group, fluorescence emission is presumed to occur by accelerated collision of electrons with holes if fluorescence emission due to photoexcitation and fluorescence emission caused by electric field application are the same.

The bond unit [D] at the center of the tertiary amine represented by the formula (1'), (6), (8) or tertiary amine compounds represented by the following formula (10):

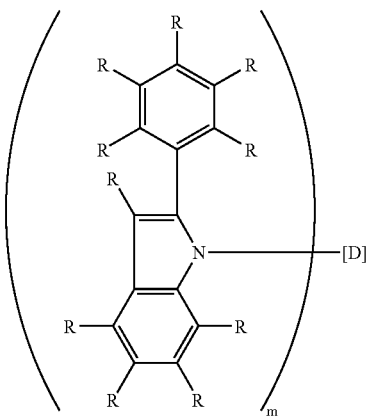

(10)

{wherein bond unit [D] represents an aromatic ring compound group or aromatic heterocyclic compound group having no substituent or one or more substituents, Rs each independently represents a substituent, and m stands for an integer of 1 or greater}) is preferably more electron donative than another bond unit (E) or (F). In addition, a bond unit having a stereostructure permitting large overlapping of wave functions between bond units (permitting easy packing) is preferred. A polyphenylene group such as a divalent biphenyl group which is three-dimensionally rotatable with a bond axis as an axis of symmetry and is an aromatic divalent conjugate molecule can be given as an example. As a molecule facilitating packing, those having not a complete planar structure but having a certain degree of stereostructure and polarizing property (intramolecular donor and intramolecular acceptor) are preferred. For example, triamine is a corn-like molecule with nitrogen atoms forming a solid angle of 109°, which improves packing property in the planar direction of the molecule and packing stability.

In the tertiary amine compounds of the invention, the bond units (E) and (F) have a great electron withdrawing property so that holes tend to appear easily in the polyphenylene group at the center of each compound. These compounds are presumed to be excellent in packing property and have high electrical conduction because the center portion serves as an intramolecular donor and the end group serves as an intramolecular acceptor so that molecular arrangement can be performed easily. Such a structure is effective for suppressing molecular vibration due to heat or electric field.

When the tertiary amine compound of the invention and a metal complex are mixed, the polyphenylene group at the center and the ligand of the metal complex are packed. The metal complex is then effective for increasing the density of the resulting low molecular weight film, thereby improving its time-dependent stability. A stereostructure having a similar shape is therefore desired in order to facilitate packing of the ligand of the metal complex and the polyphenylene group at the center.

In the formulas (1'), (6), (8) and (10), m preferably stands for an integer of from 2 to 4, more preferably 2, while n preferably stands for an integer of 1 or greater but not greater than 6, more preferably an integer of 2 or greater but not greater than 6, still more preferably an integer of 2.

In the tertiary amine compounds represented by the formulas (1'), (6), (8) and (10), the bond unit [D] (bond unit of a portion of the main chain) is characterized in that it has a skeleton structure composed of one or more electron system rings selected from the group consisting of K pieces of 6π-electron system rings, M pieces of 8π-electron system rings, N pieces of 10π-electron system rings, O pieces of 12π-electron system rings, P pieces of 14π electron system rings, Q pieces of 16π-electron system rings, R pieces of 18π-electron system rings, S pieces of 20π-electron system rings, T pieces of 22π-electron system rings, U pieces of 24π-electron system rings and V pieces of 26π-electron system rings (with the proviso that L, M, N, O, P, Q, R, S, T, U, and V each stands for an integer of from 0 to 6 and K+M+N+O+P+Q+R+S+T+U+V=from 1 to 6). The above-described tertiary amine compounds each has the above-described skeleton structure composed of π-electron ring systems and has, in the side chain of the compound, a group having an aromatic compound and/or aromatic heterocyclic compound as at least one end group.

Examples of the skeleton structure of the bond unit [D] include benzene, furan, thiophene, pyrrole, 2H-pyrane, 4H-thiopyrane, pyridine, oxazole, isoxazole, thiazole, isothiazole, furazane, imidazole, pyrazole, pyrazine, pyrimidine and pyridazine rings. Examples of the 8π-electron system rings include pentalene, indene, indolizine and 4H-quinolidine rings. Examples of 10π-electron system rings include naphthalene, azulene, benzofuran, isobenzofuran, 1-benzothiophene, 2-benzothiophene, indole, isoindole, 2H-chromene, 1H-2-benzopyrane, quinoline, isoquinoline, 1,8-naphthylidine, benzimidazole, 1H-indozole, benzoxazole, benzothiazole, quinoxaline, quinazoline, cinnoline, pteridine, purine and phthalazine rings. Examples of the 12π-electron system rings include heptalene, biphenylene, as-indacene, s-indacene, acenaphthylene, fluorene, and phenalene. Examples of the 14π-electron system rings include phenanthrene, anthracene, carbazole, xanthene, acridine, phenanthridine, perimidine, 1,10-phnanthroline, phenazine, phenarsazine, and tetrathiafulvalene rings. Examples of the 16π-electron system rings include fluoranthene, acephenanthrylene, aceanthrylene, pyrene, thianthrene, phenoxathiin, phenoxazine and phenothiazine. Examples of the 18π-electron system rings include triphenylene, chrysene, naphthacene and pleiadene rings. Examples of the 20π-electron system rings include perylene ring. Examples of the 22π-electron system rings include picene, pentaphene and pentacene rings. Examples of the 24π-electron system rings include tetraphenylene and coronene ring. Examples of the 26π-electron rings include hexaphene, hexacene and rubicene rings.

The bond unit [D] at the center of the molecule preferably has a structure excellent in symmetry relative to a plane including the bond axis of the nitrogen with the bond unit [D] and a central axis of the $sp^3$ hybrid orbital electron cloud containing a conjugated electron pair. When the bond unit [D] three-dimensionally rotates, influenced by thermal vibration or applied voltage, the above-described structure prevents an increase in the distance between the molecules of the tertiary amine compound used for the semiconductor layer and brings about excellent stability.

The bond unit [D] is selected from the above-described viewpoint. The bond unit [D] will hereinafter be expressed in the form of (L)n in which at least one bond unit (L) is linked. If in the formulas from (1') to (5), the end group composed of the chemical structure (E) and/or (F) and containing a nitrogen atom is expressed as (G), the formulas (1'), (6), (8) and (10) in which m stands for 2 and the formulas (2) to (5), (7), (9) and (11) can be expressed simply in the form of the following formula (12):

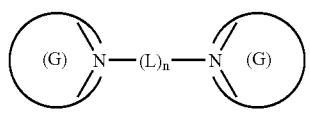

(12)

{wherein the end groups (G) may be the same or different and n stands for an integer of 1 or greater with the proviso that when n stands for 2 or greater, the bond units (L) may be the same or different}.

Similar to the formula (12), the formulas (1'), (6), (8) and (10) in which m stands for 3 can be expressed simply in the form of the following formula (13):

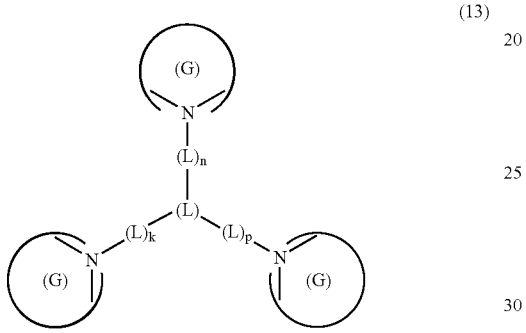

(13)

wherein the end groups (G) may be the same or different, the bond units (L) may be the same or different and n, k and p each stands for an integer of 1 or greater.

The bond unit (L) of the formula (12) or (13) will next be described. Specific examples of the bond unit (L) include derivatives of a phenylene group {for example, the below-described formulas (14) and (15)}, derivatives of a pyridine-diyl group, derivatives of a diazaphenylene group, divalent groups of oxathiazole derivatives {for example, the below-described formula (21)}, trivalent groups of triazine derivatives {for example, the below-described formula (22)}, nitrogen atoms {for example, the below-described formula (23)}, divalent groups of nitrogen- or sulfur-containing molecules, divalent groups of cardo derivatives {for example, the below-described formula (30)}, divalent groups of pyrene derivatives, divalent groups containing an unsaturated hydrocarbon {for example, the below-described formulas (32) and (33)}, divalent groups of thiophene derivatives (for example, the below-described formula (34)), divalent groups of fluorene derivatives {for example, the below-described formula (35) and fluorene-diyl group}, divalent groups of phenanthrene derivatives {for example, the below-described formula (35) and phenanthrylene group}, divalent groups of naphthalene, divalent groups of phenanthridine derivatives, derivatives of a divalent group of a nitrogen-containing heterocyclic compound, derivatives of a phenanthrine-diyl group, and derivatives of a cyclohexylidene group {the below-described formula (41)}. In addition, the bond unit (L) may be any one of arylene groups as exemplified in the formulas (1) to 117 of Japanese Patent Laid-Open No. 2001-329259. Specific examples of the bond unit (L) therefore also include derivatives of a naphthalene-diyl group, derivatives of an anthracenylene group, derivatives of a divalent biphenyl group, derivatives of a triph-enylene group, derivatives of a terphenylene group, derivatives of a quinoline-diyl group, derivatives of a quinoxaline-diyl group, derivatives of an acridine-diyl group and derivatives of a bipyridyl-diyl group.

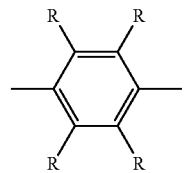

(14)

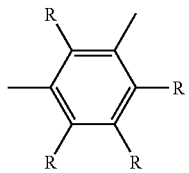

(15)

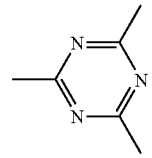

(21)

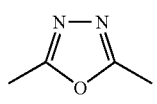

(22)

(23)

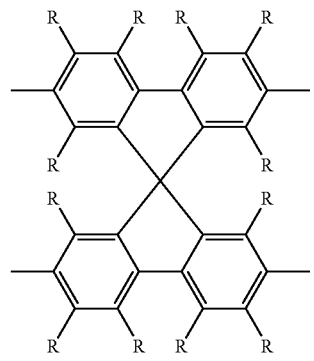

(30)

(32)

(33)

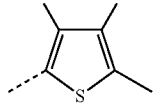

(34)

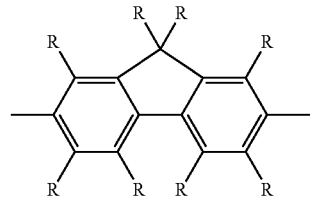

(35)

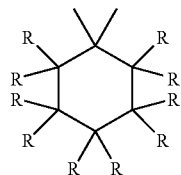
(41)

In the above-described tertiary amine compound, the substituents R each independently represents a group selected from the class consisting of hydrogen atom (atomic symbol: H), hydroxyl group, alkyl groups, alkoxy groups, alkylthio groups, alkylsilyl groups, alkylamino groups, aryl groups, aryloxy groups, arylalkyl groups, arylalkoxy groups, arylalkenyl groups, arylalkynyl groups, arylamino groups, monovalent heterocyclic compound groups, cyano group (—CN), arylalkyl groups having from 1 to 60 carbon atoms and from 0 to 60 oxygen atoms, each relating to covalent bond, oxygen atom, sulfur atom, silicon atom, phosphorus atom, bromine atom, fluorine atom, and halogen-substituted derivatives thereof. In the above-described examples, one structural formula has a plurality of substituents R which may be the same or different. They are selected independently.

The alkyl groups may be any of linear, branched and cyclic groups and they have usually from about 1 to 20 carbon atoms, with 13 as the preferred upper limit. Specific examples include methyl, ethyl, propyl, i-propyl, butyl, i-butyl, t-butyl, pentyl, hexyl, cyclohexyl, heptyl, octyl, 2-ehylhexyl, nonyl, decyl, 3,7-dimethyloctyl, and lauryl groups. Of these, methyl, pentyl, hexyl, octyl, 2-ethylhexyl, decyl and 3,7-dimethyloctyl groups are preferred, with methyl being more preferred.

The alkoxy groups may be any of linear, branched or cyclic groups and they have usually from about 1 to 20 carbon atoms. Specific examples include methoxy, ethoxy, propyloxy, i-propyloxy, butoxy, i-butoxy, t-butoxy, pentyloxy, hexyloxy, cyclohexyloxy, heptyloxy, octyloxy, 2-ethylhexyloxy, nonyloxy, decyloxy and 3,7-dimethyloctyloxy, and lauryloxy groups. Of these, penthyloxy, hexyloxy, octyloxy, 2-ethylhexyloxy, decyloxy and 3,7-dimethyloctyloxy groups are preferred.

The alkylthio groups may be any of linear, branched and cyclic group and have usually from about 1 to 20 carbon atoms. Specific examples include methylthio, ethylthio, propylthio, i-propylthio, butylthio, i-butylthio, t-butylthio, pentylthio, hexylthio, cyclohexylthio, heptylthio, octylthio, 2-ethylhexylthio, nonylthio, decylthio, 3,7-dimethyloctylthio and laurylthio groups. Of these, pentylthio, hexylthio, octylthio, 2-ethylhexylthio, decylthio and 3,7-dimethyloctylthio groups are preferred.

The alkylsilyl groups may be any of linear, branched and cyclic groups and has usually from about 1 to 60 carbon atoms. Specific examples include methylsilyl, ethylsilyl, propylsilyl, i-propylsilyl, butylsilyl, i-butylsilyl, t-butylsilyl, pentylsilyl, hexylsilyl, cyclohexylsilyl, heptylsilyl, octylsilyl, 2-ethylhexylsilyl, nonylsilyl, decylsilyl, 3,7-dimethyloctylsilyl, laurylsilyl, trimethylsilyl, ethyldimethylsilyl, propyldimethylsilyl, i-propyldimethylsilyl, butyldimethylsilyl, t-butyldimethylsilyl, pentyldimethylsilyl, hexyldimethylsilyl, heptyldimethylsilyl, octyldimethylsilyl, 2-ethylhexyl-dimethylsilyl, nonyldimethylsilyl, decyldimethylsilyl, 3,7-dimethyloctyl-dimethylsilyl and lauryldimethylsilyl groups. Of these, penthylsilyl, hexylsilyl, octylsilyl, 2-ethylhexylsi-lyl, decylsilyl, 3,7-dimethyloctylsilyl, pentyldimethylsilyl, hexyldimethylsilyl, octyldimethylsilyl, 2-ethylhexyl-diemthylsilyl, decyldimethylsilyl and 3,7-dimethyloctyl-dimethylsilyl groups are preferred.

The alkylamino groups may be any of linear, branched and cyclic groups. They may be monoalkylamino groups or dialkylamino groups and usually have from about 1 to 40 carbon atoms. Specific examples include methylamino, dimethylamino, ethylamino, diethylamino, propylamino, i-propylamino, butylamino, i-butylamino, t-butylamino, pentylamino, hexylamino, cyclohexylamino, heptylamino, octylamino, 2-ethylhexylamino, nonylamino, decylamino, 3,7-dimethyloctylamino and laurylamino groups. Of these, pentylamino, hexylamino, octylamino, 2-ethylhexylamino, decylamino and 3,7-dimethyloctylamino groups are preferred.

The aryl groups are each an atom group obtained by removing one hydrogen atom from an aromatic hydrocarbon and has usually from about 6 to 60 carbon atoms. Specific examples include phenyl, $C_1$-$C_{12}$ alkoxyphenyl ("$C_1$-$C_{12}$" means that it has from 1 to 12 carbon atoms, which will equally apply hereinafter), $C_1$-$C_{12}$ alkylphenyl, 1-naphthyl and 2-naphthyl groups, of which $C_1$-$C_{12}$ alkoxyphenyl and $C_1$-$C_{12}$ alkylphenyl groups are preferred.

The aryloxy groups usually have from about 6 to 60 carbon atoms and specific examples include phenoxy, $C_1$-$C_{12}$ alkoxyphenoxy, $C_1$-$C_{12}$ alkylphenoxy, 1-naphthyloxy, and 2-naphthyloxy groups, of which $C_1$-$C_{12}$ alkoxyphenoxy and $C_1$-$C_{12}$ alkylphenoxy groups are preferred.

The arylalkyl groups usually have from about 7 to 60 carbon atoms and specific examples include phenyl-$C_1$-$C_{12}$ alkyl, $C_1$-$C_{12}$ alkoxyphenyl-$C_1$-$C_{12}$ alkyl, $C_1$-$C_{12}$ alkylphenyl-$C_1$-$C_{12}$ alkyl, 1-naphthyl-$C_1$-$C_{12}$ alkyl and 2-naphthyl-$C_1$-$C_{12}$ alkyl groups, of which $C_1$-$C_{12}$ alkoxyphenyl-$C_1$-$C_{12}$ alkyl and $C_1$-$C_{12}$ alkylphenyl-$C_1$-$C_{12}$ alkyl groups are preferred.

The arylalkoxy groups usually have from about 7 to 60 carbon atoms and specific examples include phenyl-$C_1$-$C_{12}$ alkoxy, $C_1$-$C_{12}$ alkoxyphenyl-$C_1$-$C_{12}$ alkoxy, $C_1$-$C_{12}$ alkylphenyl-$C_1$-$C_{12}$ alkoxy, 1-naphthyl-$C_1$-$C_{12}$ alkoxy and 2-naphthyl-$C_1$-$C_{12}$ alkoxy groups, of which $C_1$-$C_{12}$ alkoxyphenyl-$C_1$-$C_{12}$ alkoxy and $C_1$-$C_{12}$ alkylphenyl-$C_1$-$C_{12}$ alkoxy groups are preferred.

The arylamino groups usually have from about 6 to 60 carbon atoms and specific examples include phenylamino, diphenylamino, $C_1$-$C_{12}$ alkoxyphenylamino, di($C_1$-$C_{12}$ alkoxyphenyl)amino, di($C_1$-$C_{12}$ alkylphenyl)amino, 1-naphthylamino, and 2-naphthylamino groups, of which $C_1$-$C_{12}$ alkylphenylamino and di($C_1$-$C_{12}$ alkylphenyl)amino groups are preferred.

The monovalent heterocyclic compound groups are each an atomic group obtained by removing one hydrogen atom from a heterocyclic compound and it usually has from 4 to 60 carbon atoms. Specific examples include thienyl, $C_1$-$C_{12}$ alkylthienyl, pyrrolyl, furyl, pyridyl, and $C_1$-$C_{12}$ alkylpyridyl groups, of which thienyl, $C_1$-$C_{12}$ alkylthienyl, pyridyl and $C_1$-$C_{12}$ alkylpyridyl groups are preferred.

Of the examples of the substituents R, substituents containing an alkyl chain may be any of linear, branched and cyclic groups or a combination thereof. When the substituent R is linear, examples include methyl, ethyl and methoxy groups. When the substituent R is not linear, on the other hand, examples include isoamyl, 2-ethylhexyl, 3,7-dimethyloctyl, cyclohexyl and 4-$C_1$-$C_{12}$ alkylcyclohexyl groups.

The substituent R also represents a halogen atom or a substituted or unsubstituted alkyl, aryl, alkoxy, aryloxy, dialkylamino, N-alkyl-N-arylamino or diarylamino group.

Specific examples include halogen atoms such as fluorine, chlorine, bromine and iodine and unsubstituted groups such as $C_{1-20}$ alkyl, $C_{3-36}$ aryl, $C_{1-20}$ alkoxy, $C_{6-36}$ aryloxy, $C_{2-20}$ dialkylamino, $C_{7-42}$ N-alkyl-N-arylamino and $C_{12-48}$ diarylamino groups.

Examples of the substituent R include alkyl groups such as methyl, ethyl, isopropyl, n-butyl, t-butyl, n-dodecyl, and cyclohexyl; aryl groups such as phenyl, naphthyl, anthracenyl, phenanthrenyl, pyranyl, naphthacenyl, pentacenyl and pentaphenyl; alkoxyl groups such as methoxy, ethoxy, isopropoxy, n-hexykloxy, cyclohexyloxy, octyloxy and dodecyloxy, aryloxy groups such as phenoxy, naphthoxy, anthracenoxy and pentacenoxy; dialkylamino groups such as dimethylamino, diethylamino, dibutylamino, dioctylamino and N-ethyl-N-butylamino; N-alkyl-N-arylamino groups such as N-methyl-N-phenylamino, N-ethyl-N-phenylamino, N-isopropyl-N-(3-methylphenyl)amino, N-methyl-N-(1-naphtyl)amino and N-butyl-N-(1-naphthacenyl)amino; and diarylamino groups such as diphenylamino, N-phenyl-N-(1-naphtyl)amino, N-(1-naphthyl)-N-(1-naphthyl)amino, N-phenyl-N-(1-anthracenyl)amino and N-(1-anthracenyl)-N-(1-phenanthrenyl)amino.

In addition, examples of the substituent R include halogen atoms, alkyl groups, aryl groups, heterocyclic groups, cyano group, hydroxy group, nitro group ($-NO_2$), carboxy group, sulfo group, amino group, alkoxy groups, aryloxy groups, acylamino group, alkylamino groups, anilino group, ureido group, sulfamoylamino group, alkylthio groups, arylthio groups, alkoxycarbonylamino groups, sulfonamide group, carbamoyl group, sulfamoyl group, sulfonyl group, alkoxycarbonyl groups, heterocyclic oxy groups, azo group, acyloxy group, carbamoyloxy group, silyloxy group, aryloxycarbonylamino groups, imide group, heterocyclic thio group, sulfinyl group, phosphonyl group, aryloxycarbonyl groups, acyl group, silyl group and azolyl group.

In the above-described example, a plurality of substituents R exist in one structural formula and they may be the same or different. They are selected independently. The substituent R is most preferred when it represents a hydrogen atom, because a long-chain substituent such as alkyl chain may presumably be decomposed by heat during vapor deposition. Moreover, in the film obtained by vapor deposition of the tertiary amine compound, such a substituent may presumably disturb intramolecular packing or undergo thermal decomposition during vapor deposition, which leads to deterioration in electrical conduction. This also applies to below-described substituents R.

In the formula (12) or (13), the end groups of the tertiary amine compound are represented by (G) with a triamine dimer or triamine trimer as an example. The end groups (G) will next be described specifically in consideration of the correspondence to the formulas (1') to formula (11).

The end groups (G) in the tertiary amine compounds represented by the formulas (12) and (13) exist at the terminal portions of the bond unit [D] as shown, for example, in the formula (1') {with the proviso that m stands for 2} and they are end groups of the tertiary amine compound which are asymmetric with respect to the bond axis of the bond unit [D] and the nitrogen atom in the bond unit {E} of the nitrogen-containing aromatic heterocyclic compound in the end group. The bond unit (E) constituting the end group of the tertiary amine and the bond unit (F) which is the side chain thereof have a molecular structure which has a higher electron withdrawing property than the bond unit [D] in the above-described order of the electron withdrawing group; and the bond unit (E) is a divalent group having an electron withdrawing property stronger than that of the bond unit (F) (which can be judged in accordance with the above-described "How to distinguish a bond unit serving as an intramolecular donor from a bond unit serving as an intramolecular acceptor"). The tertiary amine compound is thus characterized in that the bond unit (D) exhibits a donor property most strongly, the bond unit (F) exhibits an acceptor property most strongly and the bond unit (E) exhibits an electron withdrawing property at a level intermediate between them. The interaction between donor and acceptor which occurs in each bond unit in the molecules of the tertiary amine compound (charge transfer interaction or Van der Waals force) contributes to improvement in the performance (including time-dependent stability and electrical conduction) of a semiconductor layer in the organic semiconductor device of the invention.

The end groups (G) in the tertiary amine compound represented by the formula (12) or (13) exist at the terminal portions of a polyphenylene group as shown, for example, in the formulas (2) to (5) and they are end groups of tertiary amine which are asymmetric with respect to the bond axis of the polyphenylene group and the nitrogen atom in the bond unit {E} of the nitrogen-containing aromatic heterocyclic compound in the end group. The bond unit (E) is a divalent group which is more electron donative than a phenyl or naphthyl group (which can be judged in accordance with the above-described "How to distinguish a bond unit serving as an intramolecular donor from a bond unit serving as an intramolecular acceptor"). The tertiary amine compound is thus characterized in that the naphthyl or phenyl group is an intramolecular acceptor, while the bond unit (E) is an intramolecular donor. The bond unit (E') and bond unit (F') are also end groups of tertiary amine which are asymmetric with respect to the bond axis of the polyphenylene group and the nitrogen atom in the bond unit (E') of the nitrogen-containing aromatic heterocyclic compound in the end group. The bond unit (E') is a divalent group which is more electron donative than a phenyl or naphthyl group (which can be judged in accordance with the above-described "How to distinguish a bond unit serving as an intramolecular donor from a bond unit serving as an intramolecular acceptor"). The tertiary amine compound is thus characterized in that the naphthyl or phenyl group is an intramolecular acceptor, while the bond unit (E') is an intramolecular donor. The interaction between donor and acceptor which occurs in each bond unit or group (phenyl or naphthyl) in the molecules of the tertiary amine compound (charge transfer interaction or Van der Waals force) contributes to improvement in the performance (including time-dependent stability and electrical conduction) of the semiconductor layer in the organic semiconductor device of the invention.

The end groups (G) of the tertiary amine compound represented by the formula (12) or (13) correspond, for example, to compounds of the formulas (6) to (11) {with the proviso that in the formulas (6), (8) and (10), m stands for 2} having an indolyl group as each of the bond units (E) in the formula (1'), a naphthyl group as the bond unit (F) in the formulas (6) to (9) and a phenyl group as the bond unit (F) in the formula (10) or (11).

The end groups (G) in the formula (12) or (13) are substituents composed of an aromatic heterocyclic compound having in the molecule thereof at least one nitrogen atom and they may be the same or different. They are selected independently. In short, the end groups (G) may be the same substituent or may be different substituents. Specific examples of the end group will be represented by the below-described formulas (42) to (109). The below-described end groups can also be applied to cases other than triamine dimmers {m=1 or m=3 or greater in the formula (1'), formula (6), formula (8) or formula (10)}.

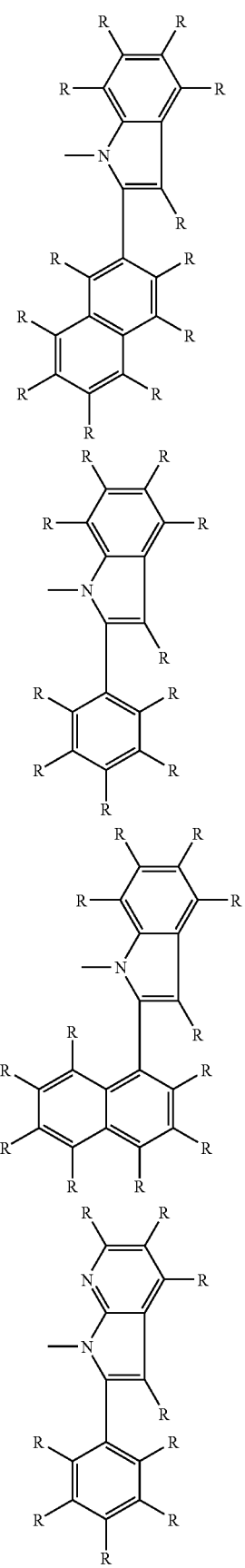
(42)
(43)
(44)
(45)
-continued
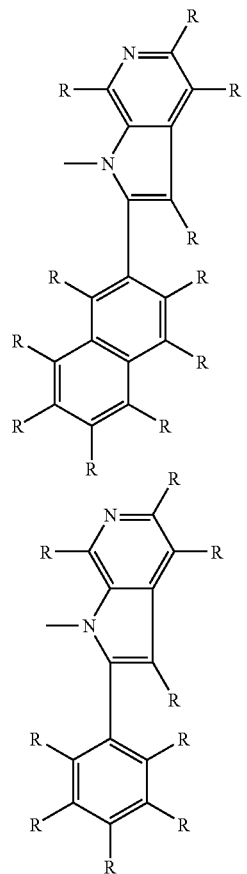
(51)
(52)
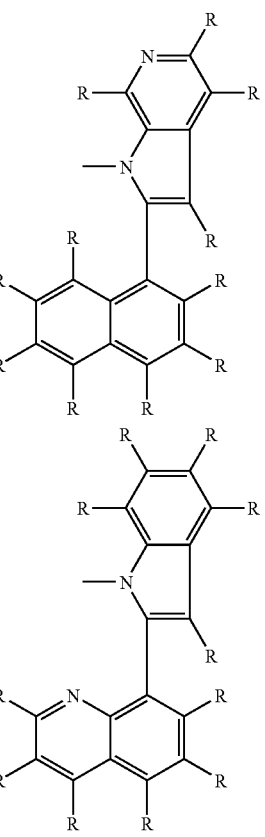
(53)
(57)

-continued
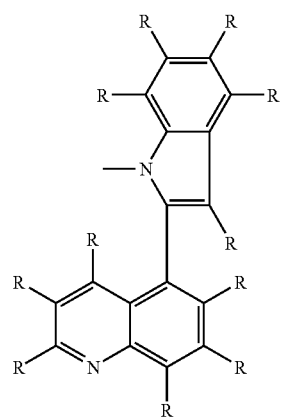 (58)
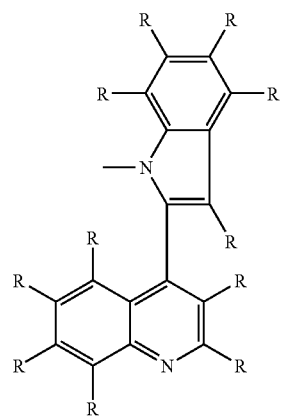 (59)
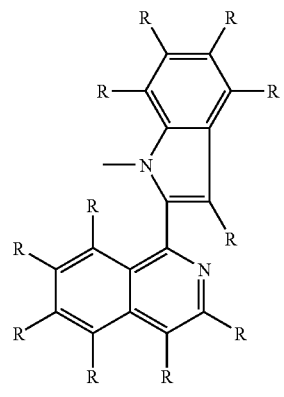 (60)
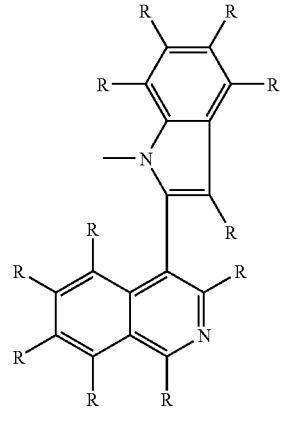 (61)
-continued
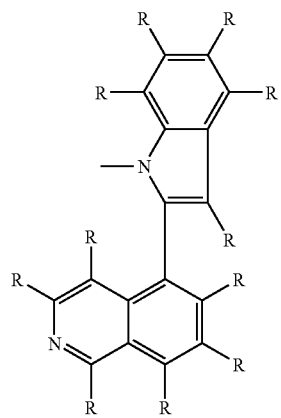 (63)
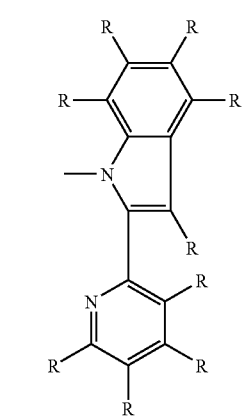 (90)
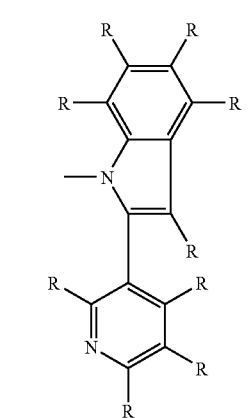 (91)
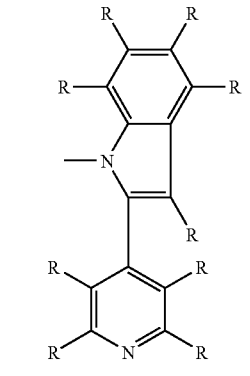 (92)

-continued

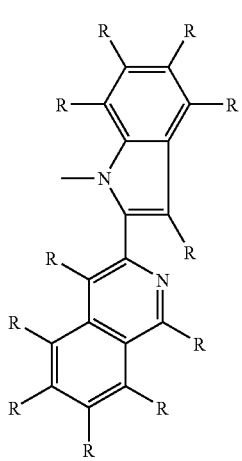

(108)

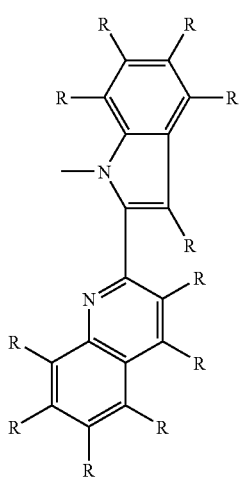

(109)

The tertiary amine compounds having the end group (G) represented by the formula (60), (90), (108) or (109) function as a ligand for forming a metal complex so that they can be used for the synthesis of the metal complex. If possible, in order to apply the metal complex together with a conductive polymer, the metal complex preferably has, in the molecule thereof, a substituent (a long chain alkyl group is introduced instead of a hydrogen atom) for heightening solubility in a solvent (there is a high possibility of the complex being decomposed before vapor deposition because it has a great molecular weight). Or, the substituents may be coupled together to form a ring.

Derivatives having a chemical structure asymmetric to a plane including the bond axis of the nitrogen atom with the bond unit [L] and a central axis of the sp$^3$ hybrid orbital electron cloud containing a non-conjugated electron pair of the nitrogen atom {typically, the bond unit (L) is bonded at 4' thereof to the 4-position of the divalent biphenyl group} can be given, for example, as the end group (G). Examples include chemical structures of tertiary amine compounds (typically, triamine dimers) having the bond unit (L) instead of the hydrogen atom at the nitrogen atom portion of a secondary amine compound to which the hydrogen atom has been bonded. Specific examples include 10H-quindoline derivatives, 6H-quindoline derivatives, 13H-acrindoline derivatives, 7H-phthaloperine derivatives, 7H-pyrazino[2,3-c]carbazole derivatives, 7H-benzo[2,3-c]carbazole derivatives, 6H-benzo[2,3-b]carbazole derivatives, 5-(2-naphthyl)pyrrole[2,3-b]pyridine derivatives, 5-(1-naphthyl)pyrrole[2,3-b]pyridine derivatives, 5-(2-naphthyl)pyrrole[3,2-b]pyridine derivatives, 5-(1-naphthyl)pyrrole[3,2-b]pyridine derivatives, 2-phenylindol-3-acetonitrile derivatives, 2-phenylindole-3-carboxyaldehyde derivatives, 2-(2-naphthyl)indole derivatives, 2-phenylindole derivatives, 2-(2-naphthyl)imidazole derivatives, 2-(1-naphthyl)imidazole derivatives, 2-phenylimidazole derivatives, 2-phenylimidazole derivatives, 2-(2-naphthyl)-1H-indazole derivatives, 2-(1-naphthyl)-1H-indazole derivatives and 2-phenyl-1H-indazole derivatives.

Of these, end groups which have therein a naphthalene skeleton and are asymmetric with respect to a plane containing a bond axis of the nitrogen atom with the bond unit [L] and a central axis of the sp$^3$ hybrid orbital electron cloud containing a non-conjugated electron pair of the nitrogen atom, such as 2-(2-naphthyl)indole derivatives and 2-(1-naphthyl)indole derivatives are especially preferred. Preferred examples of the terminal group (G) therefore include 2-(2-naphthyl)indol-1-yl{2-(2-naphthyl)indol-1-yl} group and 2-(1-naphthyl)indol-1-yl {2-(1-naphthyl)indol-1-yl} group.

In the tertiary amine compounds, any one of the substituents R of the terminal group (G) and bond unit (L) is a hydrogen atom or some of them are a methyl group, in order to avoid a fear of thermal decomposition during vapor deposition and disturb packing between molecules of the tertiary amine compound. In the tertiary amine compounds, conjugated π-electron system is preferred as a bond system of portions other than the nitrogen atom portion owing to the similar reason, because the portions other than the conjugated π-electron system inevitably become unstable, which is presumed to result in thermal decomposition during vapor deposition and deterioration in electrical conduction.

Some examples of the tertiary amine compounds represented by the formulas (1') to (11) will next be shown in the below-described formulas (136) to (138).

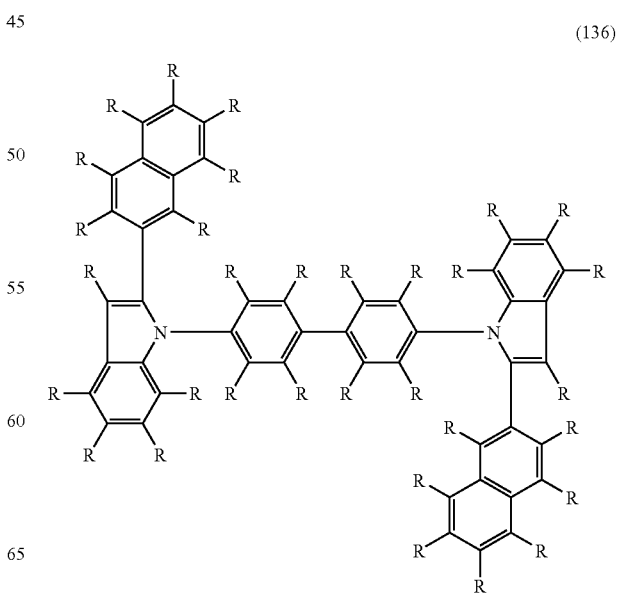

(136)

-continued

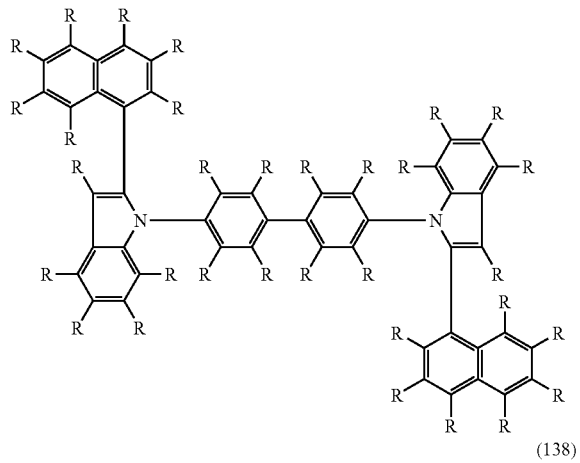
(137)

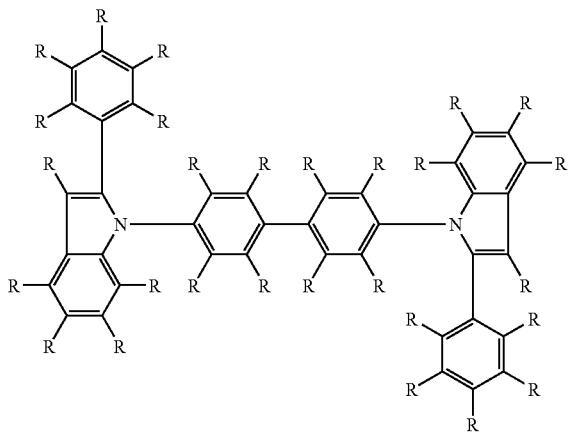
(138)

Specific examples of the tertiary amine compound include derivatives of compounds such as 4,4'-bis(2-(2-naphthyl)indol-1-yl)biphenyl, 4,4'-bis(2-(1-naphthyl)indol-1-yl)biphenyl, 4,4'-bis(2-phenylindol-1-yl)biphenyl, 4,4'-bis(2-(2-naphthyl)imidazolyl)biphenyl, 4,4'-bis(2-(1-naphthyl)imidazolyl)biphenyl, 4,4'-bis(2-phenylimidazolyl)biphenyl, 4,4'-bis(2-(2-naphthyl)indazol-1-yl)biphenyl, 4,4'-bis(2-(1-naphthyl)indazol-1-yl)biphenyl, 4,4'-bis(2-phenylindazol-1-yl)biphenyl, N-octyl-2-(2-naphthyl)indole, N-octyl-2-(1-naphthyl)indole, N-octyl-2-phenylindole, 4,4',4''-tris(2-(2-naphthyl)indolyl)triphenylamine, 4,4',4''-tris(2-(1-naphthyl)indolyl)triphenylamine, and 4,4',4''-tris(2-phenylindolyl)triphenylamine. In addition to the above-described tertiary amine compounds, the following tertiary amine compounds: 4,4'-bis(benzo[2,3-c]carbazol-7-yl)biphenyl, 4,4'-bis(benzo[2,3-b]carbazol-7-yl)biphenyl and 4,4'-bis(benzo[2,3-a]carbazol-7-yl)biphenyl may also be incorporated.

Compounds such as 4,4'-bis(2-(2-naphthyl)indol-1-yl)biphenyl represented by the formula (142) and 4,4'-bis(2-1-naphthyl)indol-1-yl)biphenyl represented by the formula (143) are especially preferred as the tertiary amine compounds.

The bond unit [D] is preferably a substituted or unsubstituted p-phenylene group or a p-polyphenylene group, while the bond unit [F] is preferably a phenyl group, 2-naphthyl group or 1-naphthyl group.

The bond unit (L) in the formula (12) or (13) is preferably a group derived from a compound containing at least one aromatic ring compound group. Specific examples of the "compound containing at least one aromatic ring compound group" include substituted or unsubstituted benzene, fused polycyclic hydrocarbons (such as naphthalene, anthracene, phenanthrene, fluoranthene, triphenylene, pyrene, chrysene, naphthacene, picene, perylene, pentaphene, pentacene and fluorene), aromatic hydrocarbon cyclic assembly (such as biphenyl, terphenyl, quaterphenyl, quinquephenyl, sexiphenyl, septiphenyl, 2,2'-binaphthyl, 1,3,5-triphenylbenzene and 9,10-diphenylanthracene), aromatic-substituted unsaturated hydrocarbons (1,2-diphenylethyne and diphenylacetylene), aromatic heterocycles (pyridine, furan, thiophene, pyrrole, 2,2'-bifuran, 2,2'-bithiophene, 2,2'-bipyrrole and 2,2'-bipyridyl), and aromatic ethers and amines (triphenylamine and diphenylether). The bond unit [D] is a group derived from these bond units (L) and it has the valence number of n.

The bond unit (L) is preferably substituted or unsubstituted benzene or a group derived from aromatic hydrocarbon ring assembly, aromatic ethers and aromatic amines, of which groups derived from an unsubstituted aromatic hydrocarbon group assembly are especially preferred.

Compounds given as examples of the tertiary amine compounds and represented by the formulas (1') to (11) will hereinafter be described in detail.

The bond unit [D] and/or bond unit (L) in the formula (1'), (6), (8) or 10 is substituted or unsubstituted arylene, a substituted or unsubstituted fused cyclic arylene or a substituted or unsubstituted heterocyclic divalent group. Specific examples include naphthylene, anthrylene, divalent biphenyl group, toluylene, pyrenylene, perylenylene, anisylene, terphenylene, phenanthrylene, xylylene, hydrofurylene, hydropyrenylene, dioxanylene, furylene, oxazolylene, oxadiazolylene, thiazolylene, thiadiazolylene, acridinylene, quinolylene, quinoxaloylene, phenanthrolylene, benzothienylene, benzothiazolylene, indolylene, silacyclopentadienylene and pyridylene groups. More specific examples include phenylene, biphenylene, tolylene, biphenyldiyl, naphthylene, fluorenediyl, binaphthalenediyl, anthrecenediyl, phenanthrenediyl, thiophenediyl, furanediyl, carbazolediyl, dibenzofuranediyl, biphenyl-4,4'-diyl, 3,3'-dimethylbiphenyl-4,4'-diyl, 3,5-dimethylbiphenyl-4,4'-diyl, 3,3',5,5'-tetramethylbiphenyl-4,4'-diyl, 3,3'-dimethoxybiphenyl-4,4'-diyl, 3,5-dimethoxybiphenyl-4,4'-diyl, 3,3',5,5'-tetramethoxybiphenyl-4,4'-diyl, diphenylmethane-4,4'-diyl, stilbene-4,4'-diyl, diphenylacetylene-4,4'-diyl, diphenylether-4,4'-diyl, benzophenone-4,4'-diyl, diphenylsulfide-4,4'-diyl, dihenylsulfone-4,4'-diyl, 1,4-naphthylene, fluorene-1,4-diyl, anthracene-1,4-diyl, furan-2,5-diyl, thiophene-2,5-diyl, isobenzofuran-1,3-diyl and thieno[2,3-b]thiophene-2,5-diyl. Of these, biphenyl-4,4'-diyl, 3,3'-dimethylbiphenyl-4,4'-diyl, diphenylmethane-4,4'-diyl, diphenylacetylene-4,4'-diyl, diphenylether-4,4'-diyl, diphenylsulfide-4,4'-diyl, diphenylsulfone-4,4'-diyl, 1,4-naphthylene, furan-2,5-diyl, thiophene-2,5-diyl, 1,3-phenylene, 5-methyl-1,3-phenylene, 1,8-biphenylene, 2,7-naphthylene, furan-2,5-diyl and thyiophene-2,5-diyl are preferred.

The tertiary amine compound of the invention is a compound represented by the above-described formula (1).

In the formula (1), n stands for an integer of from 1 to 6.
In the formula (1), p, q and r each stands for an integer of from 0 to 4.
In the formula (1), $R^1$ and $R^2$ each independently represents a group containing an aromatic ring and/or heterocycle. The aromatic ring is an aryl group having no substituent or one or more substituents in the bond unit (F) or bond unit (F'), while the heterocycle is an aromatic heterocyclic compound having no substituent or one or more substituents in the bond unit (F) or bond unit (F').

In the formula (1), $R^3$ and $R^4$ each independently represents a hydrogen atom or a $C_{1-20}$ alkyl group, preferably a hydrogen atom or a $C_{1-16}$ alkyl group, more preferably a hydrogen atom or a methyl group, still more preferably a hydrogen atom.

In one of the preferred modes of the tertiary amine compound of the invention, in the above-described formula (1), n stands for 2; p, q, and r each stands for 0; $R^1$ and $R^2$ each represents a naphthyl group; and $R^3$ and $R^4$ each represents a hydrogen atom.

In another one of the preferred modes of the tertiary amine compound of the invention, in the above-described formula (1), n stands for 2; p, q and r each stands for 0, $R^1$ and $R^2$ each represents a 1-naphthyl group; and $R^3$ and $R^4$ each represents a hydrogen atom.

In a further one of the preferred modes of the tertiary amine compound of the invention, in the above-described formula (1), n stands for 2; p, q and r each stands for 0, $R^1$ and $R^2$ each represents a phenyl group; and $R^3$ and $R^4$ each represents a hydrogen atom.

Such tertiary amine compounds can usually be analyzed for their physical properties and structures by various analysis apparatuses such as elemental analyzer, gas chromatograph mass spectrometer (which will hereinafter be abbreviated as GC-MS), infrared spectrophotometer (which will hereinafter be abbreviated as IR) and, nuclear magnetic resonance analyzer (which will hereinafter be abbreviated as NMR) and based on the data thus obtained, information on the molecules of polymer compounds can be confirmed.

Addition of Metal Complex or Metal Compound

In the organic semiconductor device of the invention, the metal content in the tertiary amine compound may be 0.1 wt. % or greater.

The organic semiconductor device of the invention comprises a substrate, a gate electrode, source and drain electrodes, and a semiconductor layer.

Substrate

No limitation is imposed on the substrate insofar as it is composed of a material having an insulating property. It is not necessarily a transparent one. Examples include, but not limited to, silicon substrate (p type or n type silicon wafer, substrate having an $SiO_2$ film formed by CVD on an n type or p type silicon wafer, or oxidized silicon wafer substrate), glass substrate (non-alkali glass substrate), plastic substrate (substrate made of polyimide, polyester, polyacryl, polyepoxy, polyethylene, polystyrene, polycarbonate, polyparaxylene, polyphenylene sulfide, polysulfone, or Teflon (trade name)), dry fused quartz substrate and a substrate made of an organic material such as sintered alumina. The substrate may be composed of a plurality of the above-described materials {for example, a substrate obtained by applying plastic (such as polyimide) to a metal substrate (such as aluminum) (used because of good heat dissipation}. The thickness of the substrate usable in the invention is from about 26 µm to 1.4 mm.

Pre-treatment

An undercoat layer is preferably laid on the substrate for increasing the adhesion strength between the substrate and an alignment layer and/or semiconductor layer. The undercoat layer is usually formed on the surface of a surface-treated substrate by the application method. Preferred examples of the surface treatment include rubbing treatment, chemical treatment (hydrophobic treatment, hydrophilic treatment or formation of a self assembled film), mechanical treatment, corona discharge treatment, flame treatment, UV treatment, RF treatment, glow discharge treatment, active plasma treatment, ozone oxidation treatment, oxygen plasma treatment, doping treatment (arsenic, boron or hydrogen), defect treatment (sputtering with an argon positive ion), surface treatment by forming a self assembled film (such as 2-mercapto-5-nitrobenzimidazolene), formation of a metal oxide film such as 1,1,1,3,3,3-hexamethyldisilazane, and treatment with an adhesion aid used for the modification of a wafer surface. Examples of the method for improving the constitution of the undercoat layer include so-called double layer method of forming, as a first layer, a layer which adheres well to a polymer film (which will hereinafter be called "first undercoat layer") and then applying thereto a hydrophilic resin layer (which will hereinafter be called "second undercoat layer") which adheres well to an alignment layer; and single layer method of applying only a resin layer containing both a hydrophobic group and a hydrophilic group. As the hydrophobic treatment, a method of treating the surface of a silicon oxide film with octadecyltrichlorosilane (OTS) is employed for example.

Formation Method of a Semiconductor Layer

A semiconductor layer in the organic semiconductor device using the tertiary amine compound of the invention features that it has the tertiary amine compound of the invention as a principal component {it may contain a metal complex and/or metal compound) and it is formed by deposition in vacuum (vacuum deposition). For example, it is formed by deposition of a material mixture of the tertiary amine compound and a metal complex and/or subjecting the tertiary amine compound and metal complex as respective materials to vacuum deposition (which is also called "co-deposition") and/or subjecting only the tertiary amine compound to vacuum deposition. It is needless to say that the vacuum deposition may be performed via a mask (such as shadow mask or hard mask), or that the semiconductor layer thus formed may be subjected to etching treatment (such as wet etching or dry etching). The semiconductor layer may be formed by any another known process. During and/or after formation of the semiconductor layer, it is exposed to ionizing radiation (such as X ray, UV light, infrared ray or electron ray) or ion beam.

In the organic semiconductor device of the invention, the semiconductor layer preferably contains the metal complex.

When the semiconductor layer contains the metal complex, the performance of the organic semiconductor device can be improved by intercalation of the metal complex and the molecule of and tertiary amine compound to form a laminar compound.

Examples of a metal (in the below description of metals, Y and R each represents an alphabet of atomic symbol) constituting the metal complex include Period 2 elements such as Li and Be, Period 3 elements such as Na, Mg and Al, Period 4 elements such as K, Ca, Sc, Ti, V, Cr, Mn, Fe, Co, Ni, Cu, Zn, Ga, Ge and Se, Period 5 elements such as Ag, Au, Pb, Rb, Sr, Y (this Y representing yttrium), Zr, Nb, Mo, Tc, Ru, Rh, Pt, Cd, In, Sn, Sb and Te, Period 6 elements such as Ba, Hf, Cs, Ir, W, Os, Hg, Tl and Bi, lanthanoid series elements such as La, Ce, Pr, Nd, Pm, Sm, Eu, Gd, Tb, Dy, Ho, Er, Yb and Lu and actinoid series elements such as Ac, Th, Pa, U, Np, Pu, Am, Cm, Bk, Cf and Es. Of these, Li, Be, Na, Mg, Sr, Cs, Rb, K, Ba, Ir, Zn, Cu and Al are preferred.

The identification and quantitative determination of such metals in the tertiary amine compound can be performed by various analytical instruments such as ICP-AES (Inductively Coupled Plasma-Atomic Emission Spectroscopy, which will hereinafter be abbreviated as ICP).

Examples of the metal complex used in combination with the tertiary amine compound of the invention include tris(phenylpyridyl)iridium complex {usually described as "Ir(ppy)$_3$", chemical formula: $C_{33}H_{24}IrN_3$}, tris(8-hydroxyquinoilnato)aluminum {usually described as "Alq3", chemical formula: $C_{27}H_{18}AlN_3O_3$}, and bis(2-(2-hydroxyphenyl)benzo-1,3-thiazolate)zinc complex (chemical formula: $C_{26}H_{16}N_2O_2S_2Zn$) and combination thereof. The metal complex usable in the invention is not limited to the above-described ones.

Organic Semiconductor Device

The organic semiconductor device of the invention has a semiconductor layer between at least a pair of electrodes. It is preferred that the semiconductor layer has an intramolecular donor and an intramolecular acceptor in the end group at the terminals of the above-described bond unit [D] and as the bond unit [D], has a structure which has good symmetry and therefore tends to cause packing by free rotation. The bond unit [D] may be typically a ligand or a bond unit having a stereostructure similar to the ligand. It may have, as the substituent, one or more than one substituents. The end group (G) is preferably a molecule having an almost similar structure to a plane structure (which will be called "quasi-planar structure") and it has, in one part of its molecular structure, nematic liquid crystals, smectic liquid crystals, discotic liquid crystals, cholesteric liquid crystals or a portion of them; a molecule capable of forming a helix structure; or a portion of the molecular structure. The organic semiconductor device of the invention may contain, in addition to the above-described tertiary amine compound, a metal complex.

The above-described tertiary amine compound incorporated in the semiconductor layer preferably has a structure comprising end groups with a quasi-planar structure typified by liquid crystals and between these end groups, a bond unit [L] {preferred typical example of the bond unit (L) is a point group $D_{nh}$, especially a point group $C_{nv}$ (n standing for 2 or greater)} having good symmetry.

The organic semiconductor device of the invention is characterized in that, for example when it has at least two electrodes and an electrically conductive semiconductor layer over a substrate, the semiconductor layer is formed using at least one of the tertiary amine compounds of the invention as a main component.

Examples of the organic semiconductor device of the invention include, but not limited to, vertical organic semiconductor devices and horizontal organic semiconductor devices.

Examples of the horizontal organic semiconductor devices include top contact type (substrate/gate electrode/gate insulating layer/semiconductor layer/source and drain electrodes or substrate/gate electrode/gate insulating layer/alignment layer (alignment layer formed by etching or vapor deposition)/semiconductor layer/source and drain electrodes) and bottom contact type (substrate/gate electrode/gate insulating layer/source and drain electrodes/semiconductor layer or substrate/gate electrode/gate insulating layer/source and drain electrodes/alignment layer (alignment layer formed by etching or vapor deposition)/semiconductor layer)(in the above description, the slash "/" means that two layers with/therebetween are stacked one after another).

Various structures of organic semiconductor device are described, for example, in Nature, 393, 619(1998), *Appl. Phys. Lett.*, 62, 1794 and *Appl. Phys. Lett.*, 63, 1372. The structure is also described in FIGS. 2(a), 2(b) and 2(c) in "Organic Polymer Transistor" of *High Polymers*, 51 (February issue), 79(2002)".

The vertical organic semiconductor transistor has a structure resembling a device called "permeable-base transistor" or "static induction transistor (SIT)". A typical example of this structure is described in FIG. 2(d) in "Organic-Polymer Transistor" of *High Polymers*, 51 (February issue), 79(2002)"

The organic semiconductor device may be a multi gate type device having at least two gate electrodes, for example, double gate type one. For example, it may have, in one circuit thereof, at least one gate electrode. Examples of the double gate type structure include planar structure, fin structure and vertical structure.

The organic semiconductor device of the invention may have another constitution, for example, (i) substrate/gate electrode/gate insulating layer (serving also as an alignment layer)/source and drain electrodes/semiconductor layer(/protection layer), (ii) substrate/gate electrode/gate insulating layer/source and drain electrodes/alignment layer/semiconductor layer(/protection layer), (iii) substrate/gate electrode/gate insulating layer (also serving as an alignment layer)/semiconductor layer/source and drain electrodes(/protection layer), (iv) substrate/gate electrode/gate insulating layer (also serving as an alignment layer)/semiconductor layer/substrate having source and drain electrodes patterned thereon (serving also as a protection layer), (v) substrate/source and drain electrodes/semiconductor layer/gate insulating layer (also serving as an alignment layer)/gate electrode/substrate (also serving as a protection layer), (vi) substrate (serving also as an alignment layer)/source and drain electrodes/semiconductor layer/gate insulating layer/gate electrode/substrate (serving also as a protection layer), or (vii) substrate/gate electrode/gate insulating layer/source and drain electrodes/semiconductor layer/substrate (serving also as an alignment layer) (in the above description, slash "/" means that two layers with/therebetween are stacked one after another".

The organic semiconductor device of the invention preferably comprises a gate electrode disposed on/above a substrate, a gate insulating layer disposed on/above the gate electrode, source and drain electrodes disposed on/above the gate insulating layer, and a semiconductor layer disposed on/above the gate insulating layer, and source and drain electrodes. The organic semiconductor device can be called a bottom gate type or an inverted staggard type of device.

The organic semiconductor device of the invention may comprise a source electrode, a semiconductor layer disposed on/above the source electrode, a gate electrode embedded in the semiconductor layer, and a drain electrode disposed on/above the semiconductor layer.

The organic semiconductor device of the invention may comprise a gate electrode, source electrode and a drain electrode disposed on/above a substrate, a gate insulating film formed only on/above the gate electrode ("film" is used here instead of "layer" because it is disposed on/above only a portion of the gate electrode), and a semiconductor layer disposed on/above the substrate, gate insulating film, source electrode and gate electrode. The organic semiconductor device can be called a bottom gate type or an inverted staggard type of device.

The organic semiconductor device of the invention may comprise a gate electrode disposed on/above a substrate, a gate insulating layer disposed on/above the gate electrode, a semiconductor layer disposed on/above the substrate and gate insulating layer, and a source electrode and drain electrode disposed on/above the semiconductor layer. The organic semiconductor device can be called a bottom gate type or an inverted staggard type of device.

The organic semiconductor device of the invention may comprise a semiconductor layer disposed on/above a substrate, a source electrode and a drain electrode disposed on/above the semiconductor layer, a gate insulating layer disposed on/above the semiconductor layer, source electrode and drain electrode, and a gate electrode disposed on/above the gate insulating layer. The organic semiconductor device can be called a top-gate type or a staggard structure type of device.

The organic semiconductor device of the invention may comprise a source electrode and a drain electrode disposed on/above a substrate, a semiconductor layer disposed on/above the substrate, source electrode and drain electrode, a gate insulating layer disposed on/above the semiconductor layer, and a gate electrode disposed on/above the gate insulating layer. The organic semiconductor device can be called a top-gate type or a staggard structure type of device.

The organic semiconductor device of the invention may comprise a source electrode, a drain electrode and a gate electrode disposed on/above a same substrate, a gate insulating layer disposed on/above the gate electrode, a semiconductor layer disposed on/above the gate insulating layer, the source electrode and the drain electrode. The organic semiconductor device can be called a planar type of device.

When the semiconductor layer contains the tertiary amine compound of the invention, the resistivity of the tertiary amine compound is preferably $10^5$ Ω·cm or greater but not greater than $10^9$ Ω·cm at an applied voltage of $2\times10^6$ V/cm when the thickness of the semiconductor layer is adjusted to 50 nm. In order to reduce the leakage current between luminance pixels, the resistivity is preferably $10^5$ Ω·cm or greater but not greater than $10^7$ Ω·cm, more preferably $10^5$ Ω·cm or greater but not greater than $10^6$ Ω·cm. When the thickness of the semiconductor layer is adjusted to 50 nm, the resistivity preferably falls within a range of from $10^6$ Ω·cm to $10^8$ Ω·cm at an applied voltage of $2.6\times10^5$ V/cm, while the resistivity preferably falls within a range of from $10^5$ Ω·cm to $10^7$ Ω·cm at an applied voltage of $2.6\times10^5$ V/cm.

Co-deposition of an adequate amount of a low molecular weight compound with the tertiary amine compound of the invention may be adopted as a conventional method for adjusting the electrical conductivity of the tertiary amine compound of the invention to fall within the above-described range.

In order to adjust the thickness of the semiconductor layer formed by the tertiary amine compound of the invention to optimum thickness, a film is deposited while measuring the film thickness by a film thickness meter utilizing, for example, a crystal oscillator and then, a shutter is closed when it reaches the optimum thickness.

In the organic semiconductor device of the invention, the tertiary amine compound preferably has a glass transition point of from 90 to 200° C., most preferably from 130 to 160° C. When the tertiary amine compound has a glass transition point exceeding 200° C., the orientation property sometimes lowers owing to stiffness of its main molecular chain, while when it has a glass transition point less than 90° C., the product loses its reliability (short product life).

In the organic semiconductor device, the tertiary amine compound has preferably a melting point of from 180 to 360° C., most preferably from 250 to 300° C. When the melting point of the tertiary amine compound exceeds 300° C., the orientation property sometimes lowers owing to excessive stiffness of its main molecular chain, while when the melting point is less than 180° C., the product loses its reliability.

The tertiary amine compound preferably has an evaporation temperature of from 280 to 490° C., most preferably from 350 to 450° C. When the evaporation temperature is less than 280° C., cohesive force of the deposited film is small, which leads to deterioration in electrical conduction and time-dependent stability. When the evaporation temperature exceeds 490° C., the compound undergoes thermal decomposition during vapor deposition, which disturbs formation of a uniform film.

The glass transition point and melting point of the tertiary amine compound can be measured using a differential scanning calorimeter (which will hereinafter be abbreviated as "DSC"). They are specified by a transition starting temperature at a heating rate of 10° C./min. For example, the transition point of the tertiary amine compound of the invention represented by the formula (136) in which substituents R each represents a hydrogen atom was 110° C. at a heating rate of 10 K/min and its melting point was 280° C. For the measurement, "EXSTAR 6000 DSC6200" (trade name; product of Seiko Instruments) can be used.

The evaporation temperature of the tertiary amine compound can be measured by a thermo-gravimetric/differential thermal analyzer (which will hereinafter be abbreviated as "TG/DTA"). For example, the decomposition temperature of the tertiary amine compound of the invention represented by the formula (136) in which substituents R each represents a hydrogen atom was 300° C. For the measurement, "EXSTAR TG/DTA 6200" (trade name; product of Seiko Instruments) can be used.

When measurement is performed using DSC or TG, a sample obtained by dissolving an organic semiconductor device in a solvent such as tetrahydrofuran which does not dissolve therein an alignment layer and then vacuum drying and/or heat drying the resulting solution, or a sample obtained by heating and melting even an isotropic layer and then collecting it. If an impurity is contained, the sample may be separated and purified, for example, by chromatography.

The tertiary amine compound of the invention may be used in the crystal form. The crystal system may be tetragonal, trigonal, rhombic, triclinic, monoclinic, cubic, hexagonal or rhombohedral or may have a system similar thereto. In particular, it preferably has a rhombic, trigonal or rhombohedral system or a system similar thereto. These crystal structures can be confirmed by an X-ray diffractometer. It may have a plurality of systems, depending on the voltage application time, that is, before application or after application, or voltage. It may have a polycrystalline compound having the above-described system. Or the tertiary amine compound of the invention may form a clathrate crystal with a solvent.

The semiconductor layer contains a metal compound preferably in an amount of from 0.5 to 20 wt. %, more preferably in an amount of from 1 to 10 wt. %. Such an amount of the metal compound is effective for heightening the electrical conductivity.

The resistivity of the semiconductor layer thus formed is preferably from $10^4$ Ω·cm to $10^{10}$ Ω·cm, more preferably from $10^4$ Ω·cm to $10^8$ Ω·cm at an applied voltage of $2.6\times10^5$ V/cm and preferably from $10^4$ Ω·cm to $10^9$ Ω·cm, more preferably from $10^4$ Ω·cm to $10^7$ Ω·cm at an applied voltage of $2 \times 10^6$ V/cm. The semiconductor layer having such a range of resistivity is effective for improving the performance of the organic semiconductor device because a current difference of the device between switching time and non-switching time becomes large. The above-described resistivity can be measured using an ordinary method such as two terminal measurement, three terminal measurement, four terminal measurement or van der Pauw method, or a method using a comb-shaped electrode substrate.

Thickness of Semiconductor Layer

The semiconductor layer has a thickness of from 1 nm to 10 µm, preferably from 2 nm to 2 µm, more preferably from 10 nm to 1 µm.

Orientation Method

In the organic semiconductor device of the invention, it is possible to control the orientation direction of the molecules of the tertiary amine compound of the semiconductor layer by forming an alignment layer using an alignment film made of a polymer and forming thereover the semiconductor layer containing the tertiary amine compound. As a result, the organic semiconductor device has improved performance. The alignment layer may be formed by oblique deposition of SiO via a mask or the alignment layer of the tertiary amine compound by a voltage or magnetic field.

In the organic semiconductor device, the formation of the semiconductor layer on the alignment layer may include a step of obtaining uniform oblique orientation.

In the invention, the orientation of the tertiary amine compound can be effected in various manners. Some combinations of the tertiary amine compound and substrate permit effective orientation when vapor deposition is conducted on a substrate surface after rubbing treatment. A method of forming an alignment layer from an alignment film is most popular method. The alignment layer is, for example, a film formed by oblique deposition of an inorganic substance or a film obtained by subjecting an alignment film formed using a specific polymer to rubbing treatment. A thin film, such as monomolecular film composed of an azobenzene derivative, obtained by isomerization by light and having molecules oriented uniformly is also embraced by the alignment layer. The term "alignment layer" in the broad sense means a glass substrate or silicon substrate subjected to simple rubbing treatment.

Especially Preferred Alignment Film

A polyimide film is a typical example of an alignment film constituting the alignment layer. The tertiary amine compound can be oriented by applying polyamic acid (for example, "SE-7210", trade name; product of Nissan Chemical) to a substrate surface, baking it at from 100 to 300° C., and then rubbing the surface. The film obtained using an alkyl-chain-modified POVAL (for example, "MP203" or "R1130", trade name; product of Kuraray) can be imparted with an orientation effect only by rubbing without baking. In addition, most of organic polymer films forming a hydrophobic surface such as polyvinyl butyral or polymethyl methacrylate acquire an orientation effect of the tertiary amine compound by rubbing the surface to which it has been applied. The typical example of the film formed by oblique deposition of an inorganic substance is an SiO obliquely deposited film. This alignment layer is available by obliquely applying SiO deposition particles to the surface of a base film in a vacuum chamber, thereby forming an obliquely deposited film of about 20 to 200 nm thick. When the tertiary amine compound is oriented by this deposited film, the optical axis of the semiconductor layer turns to a specific direction on a plane which includes the movement locus of the SiO deposition particles and is vertical to the surface of the base film.

The formation of the semiconductor layer by depositing the tertiary amine compound onto a glass substrate or the above-described alignment layer may include a step of applying an electric field and/or magnetic field at an optimum angle.

It may include a step of, while depositing a tertiary amine compound onto a glass substrate or the above-described alignment layer to form a semiconductor layer and heating the semiconductor layer by an IR lamp (infrared lamp), applying an electric field and/or magnetic field to the resulting semiconductor layer at an optimum angle and also a subsequent step of cooling the semiconductor layer.

Rubbing treatment for uniformly orienting the molecules of the tertiary amine compound of the invention may be added to the above-described steps after rubbing the glass substrate and/or forming the alignment layer on the surface of the substrate by the alignment film. A deposition crucible containing therein the tertiary amine compound to be deposited to a region of the semiconductor layer has preferably a temperature of 200° C. or greater but not greater than 500° C., especially preferably 300° C. or greater but not greater than 420° C.

The tertiary amine compound deposited onto the substrate can be obliquely oriented by magnetic field orientation or electric field orientation, as well as by the above-described method using an alignment film. In this method, a space for applying a magnetic field or electric field at a desired angle is disposed between a deposition source and the substrate when the tertiary amine compound is deposited onto the substrate.

The above-described alignment layer can determine the orientation direction of the molecule of the tertiary amine compound deposited on the alignment layer. The orientation of the molecule of the tertiary amine compound depends on the alignment film for the formation of the alignment layer so that their combination must be optimized. After orientation, the molecule of the tertiary amine compound is oriented at a certain angle θ relative to the surface of the substrate. When the tertiary amine compound is not a mixture, the angle of the oblique orientation does not show a large change depending on the kind of the alignment film and it tends to be a value specific to the molecule of the tertiary amine compound. When two or more tertiary amine compounds are mixed, the angle can be adjusted within a certain range in accordance with their mixing ratio. Accordingly, for the control of the angle of oblique orientation, selection of the kinds of the tertiary amine compounds and method such as deposition of a mixture of two or more tertiary amine compounds are effective.

As the alignment film, a film obtained by baking an alkyl-containing polyamic acid is especially preferred because it is excellent in the ability of uniformly orienting the tertiary amine compound. This ability is presumed to appear owing to strong interaction between the alkyl chain on the surface of the alignment layer formed using the alignment film and the alkyl side chain of the tertiary amine compound. Since the tertiary amine compound of the invention polarizes compared with ordinary tertiary amine compounds, an alkyl group having less carbon atoms than that used for the orientation of ordinary tertiary amine compounds can be used for the orientation. The number of carbon atoms is preferably from 1 to 30, more preferably from 1 to 14, most preferably from 1 to 7. Such shortening of the alkyl chain is preferred also from the viewpoint of electrical conduction.

A polyimide film (preferably, fluorine-containing polyimide) widely used as an alignment film for LCD (Liquid Crystal Display) is also preferred for the formation of the alignment layer. It is available by applying polyamic acid (for example, "LQ/LX series", trade name; product of Hitachi Chemical and "SE series", trade name; product of Nissan Chemical) onto the surface of a support, baking the resulting support at from 100° C. to 300° C. for 0.5 to 1 hour and then rubbing. Moreover, the alignment layer of the organic semiconductor device of the invention may be formed by a cured film available by introducing a reactive group into the polymer of the alignment film or using the polymer of the alignment film with a crosslinking agent such as isocyanate compound or epoxy compound, and thereby curing the polymer.

For the above-described rubbing, a rubbing method widely used in the orientation process of LCD can be utilized. Described specifically, the surface of the alignment layer is rubbed in a fixed direction with paper, gauze, felt, rubber, or nylon or polyester fiber. It is the common practice to carry out rubbing about several times with a cloth in which fibers uniform in length and width have been transplanted at equal intervals.

Examples of the deposition substance used for the formation of an obliquely-deposited inorganic film include, in addition to SiO as a representative, metal oxides such as $TiO_2$ and $ZnO_2$, fluorides such as $MgF_2$ and metals such as Au and Al. Metal oxides are not limited to the above-described ones and those having a high dielectric constant can be used as the substance for oblique deposition. The obliquely deposited organic film can be formed by a deposition apparatus. It can be formed by depositing while fixing a film (support) or continuously depositing while moving a long film.

Alignment Film

Examples of the organic compound used for the formation of the alignment film constituting the alignment layer of the organic semiconductor device of the invention include polymers such as polymethyl methacrylate (PMMA), polystyrene (PS), polyvinyl alcohol (PVA), polyvinylidene fluoride (PVdF), polyethylene tetrafluoride derivatives, perfluoroalkoxyfluorine resin (PFA) derivatives, copolymers of ethylene trifluoride derivative/propylene hexafluoride derivative, copolymers of ethylene derivative/ethylene tetrafluoride, vinylidene fluoride derivatives, polychlorotrifluoroethylene derivatives, vinyl fluoride derivatives, polydimethylsilane (PDMS) derivatives, polyvinylcarbazole derivatives, polymethyl methacrylate derivatives, derivatives of acrylic acid/methacrylic acid copolymer, derivatives of styrene/maleimide copolymer, polyvinyl alcohol derivatives, poly(N-methylol acrylamide) derivatives, derivatives of styrene/vinyl toluene copolymer, chlorosulfonated polyethylene derivatives, nitrocellulose derivatives, polyvinyl chloride derivatives, chlorinated polyolefin derivatives, polyester derivatives, polyimide derivatives (obtained by baking polyamic acid, soluble polyimide or mixture thereof), derivatives of vinyl acetate/vinyl chloride copolymer, derivatives of ethylene/vinyl acetate copolymer, carboxymethyl cellulose derivatives, polyethylene derivatives, polypropylene derivatives and polycarbonate derivative; compounds such as silane coupling agents; and polyamide resins (such as nylon), acrylate/styrene/acrylonitrile copolymers, acrylonitrile/butadiene/styrene copolymer, acrylate copolymers, olefin vinyl alcohol copolymers, alkyd resins, amino resins (urea resins, melamine resins, benzoguanamine resins), bismaleimide triazine resins, cellulose plastics (cellulose acetate derivatives, cellulose butyroacetate derivatives, ethyl cellulose derivatives), chlorinated polyether derivatives, coumarone reins, coumarone/indene/styrene copolymer, chlorinated polyethylene derivatives, allyl resins, ethylene-α-olefin copolymers, ethylene/vinyl acetate/vinyl chloride copolymer, ethylene/vinyl chloride copolymer, epoxy resins, polyethylene/vinyl acrylate copolymer, polyethylene derivatives, polypropylene derivatives, polyvinyl chloride derivatives, vinyl acetate derivatives, furan resins, fluorine resins (polyethylene fluoride derivatives, perfluoroalkoxyfluorine resins, ethylene tetrafluoride/propylene hexafluoride copolymer, vinylidene fluoride derivatives (such as polyvinyl fluoride), polychlorotrifluoroethylene derivatives, vinyl fluoride derivatives), methyl acrylate copolymers, butadiene copolymers, styrene copolymers, polyacrylonitrile, ionomers, ketone resins, oxybenzoyl polyesters, petroleum resins (such as terpin resins), phenol resins, polyacetal, polyamidoimide, polyarylate, polyallylsulfone, polybutadiene, thermosetting polybutadiene, polyetherimide, polybutylene, polybutylene terephthalate, polycarbonates, modified polycarbonates, polyesters, polyether sulfones, polyethylenes, water-crosslinked polyethylenes, polyethylene terephthalates, polyimides, polyaminobismaleimide, methacrylic resins, polymethylpentene, polyphenylene oxide, polyphenylene sulfide, polyphenylene sulfone, polysulfone, polystyrene resin, styrene-acrylonitrile copolymer, styrene copolymers, butadiene/styrene resins, polyether ether ketone, polyurethane, vinyl acetate resins, polyvinyl acetal, cyanoethylpullulan, polyoxymethylene, polychloroprene, polysulfone, polyvinyl chloride, polyvinyl alcohol, acryl-modified polyvinyl chloride, polyvinylidene chloride, thermoplastic elastomers (styrene/butadiene resins, polyester resins, polyethylene resins, urethane resins, vinyl chloride resins, silicone resins, unsaturated polyester resins, vinyl ester epoxy resins, xylene resins, alkyd resins, phenol resins, acrylonitrile resins, etc.) acrylonitrile graft copolymers, modified polyolefins, Novalloy (trade name, product of Daicel Polymer), "Superlex-W" (trade name; product of Mitsubishi Monsanto), alkyd phthalate resins, alkyd resins, modified alkyd resins (phenol modified resins, styrenated resins, aminoalkyd resins, etc.), acrylic resins, polyester resins and melamine resins. A plurality of these films may be used in combination. The molecule of the tertiary amine compound can be also anisotropically oriented in a specific direction by the contact of the alignment layer with a curable resin having minute unevenness on the surface thereof or a substrate material and a curable resin having minute unevenness on the surface thereof.

Particularly preferred examples of the polymer used for the alignment film include polyimides (obtained by baking polyamic acid, soluble polyimide or mixture thereof), polystyrene, polymers of a styrene derivative, gelatin, polyvinyl alcohol, and alkyl-modified polyvinyl alcohols having an alkyl group (preferably having at least 6 carbon atoms). Derivatives, mixtures or copolymers of the above-described materials can also be used. By the alignment layer available by subjecting such a polymer layer to the orientation treatment, the molecule of the tertiary amine compound can be oriented into a desired direction.

Even without alignment layer formed by a polymer, the molecule of the tertiary amine compound can be oriented into a desired direction by rubbing a glass substrate or a silicon substrate. The organic semiconductor device can be miniaturized by having the alignment film serve as a resist and employing photolithography to limit a region in which the molecule of the tertiary amine compound is oriented into a desired direction. For example, the electrical conduction of the tertiary amine compound can be controlled in a specific region (such as a region of a semiconductor layer and a region other than the semiconductor layer) because an alignment layer can be formed locally by using a photosensitive polyimide or photosensitive polyamide.

Method for Forming an Electrode, Semiconductor Layer and/or Alignment Layer Other than Vapor Deposition The above-described semiconductor layer is preferably formed by vapor deposition. It is also possible to apply coating solutions obtained by dissolving polymer of the alignment film and the tertiary amine compound of the invention in respective solvents and applying the resulting coating solutions in the below-described method. Examples of the coating method to be employed in the invention include spin coating, cast coating, dip coating, die coating, bead coating, bar coating, roll coating, spray coating, gravure coating, flexo printing, screen printing, offset printing, curtain coating, extrusion coating, printing coating, ink jet, slide coating, pulling method and transfer method. Of these, spin coating, spray coating and ink jet method are preferred, of which ink jet method and spray coating are most preferred. The semiconductor layer is formed by applying a solution of the tertiary amine compound by the above-described method, drying the resulting layer by heating and then cooling it. The term "coating solution" as used herein embraces a melt, solution, dispersion and mixture. The semiconductor layer can be formed by heating the tertiary amine compound of the invention to its melting temperature and at the same time, spin-coating the molten compound on a substrate. The formation processes of the semiconductor layer and alignment layer are not limited and any known process can be employed.

In the organic semiconductor device of the invention, examples of the solvent used for preparing a coating solution of the polymer of the alignment film include hydrocarbons, ethers, amides and halogenated hydrocarbon solvents such as pyridine, acetonitrile, ethyl lactate, n-butyl acetate, ethyl cellosolve acetate, propylene glycol monoethyl ether acetate (PGMEA), 3-methyl methoxypropionate, ethoxyethyl propionate, n-hexane, cyclohexane, γ-butyrolactone, o-dioxane, m-dioxane, p-dioxane (1,4-dioxane), N-methyl-2-pyrrolidone (NMP), N,N'-dimethylacetamide, dimethylformamide, N,N-dimethylformamide, dimethylsulfoxide, diglyme, chloroform, carbon tetrachloride, γ-butyrolactone, γ-valerolactone, phenol, o-cresol, m-cresol, p-cresol, ethanol, methanol, xylene, toluene, tetrahydrofuran, water, trichloroethylene, tetrachloroethylene, 1,1,1-trichloroethane, 1,1,2-trichloroethane, 1,2-dichloroethylene, 1,1-dichloroethylene, 1,3-dichloropropene, pentachlorophenol, dichloromethane, methyl ethyl ketone, cyclohexanone, 1-methoxy-2-propanol, 2-propanol, 2-butoxyethanol, ethyl 2-ethoxypropionate, acrylonitrile, propylene glycol, 1-monomethyl ether-2-acetate, ethyl 3-ethoxypropionate, oleic acid, diphenyl ether, diethyl ether, petroleum ether, 2-butoxyethanol, perchloric acid, 1-bromooctane, 1-bromododecane, 3-methoxybutyl acetate, 1,4-dimethylbenzene, dimethylsulfoxide, benzene, monochlorobenzene, pyridine, hydrochloride, tetraline, o-dichlorobenzene, acetic acid, ethyl acetate, diphenyl ether, biphenyl ether 1,2-dimethoxyethane, monochlorobenzene, benzonitrile, quinoline, 1,3-dimethylbenzene, nitrobenzene, aqueous ammonia, 1-butanol, diethylene glycol dimethyl ether, propylene glycol, 2-propanol, 2-butanone, 4-methyl-2-pentanone, dimethyl diglycol, 1,1, 2,2-tetrachloroethane, ethylbenzene, 1,2-dimethylbenzene, anisole, 1-cyclohexyl-2-pyrrolidone, n-dodecylmercaptane, carbon disulfide, 1-propanol, 1-dodecanol, n-pentyl alcohol, 2-dimethylaminoethanol, 2-aminoethanol, trifluoroacetic acid, ethyl 3-oxobutanoate, ethyl acetoacetate, n-pentyl alcohol, 3-methoxybutyl acetate, acetone, 2,2',2"-nitriloethanol, butyl acetate, tri-n-propylamine, n-hexylamine, dodecylamine, dibutylamine, aqueous dimethylamine solution, diethyltriamine, aniline, triethylamine, heptane, cholic acid, o-tolidine, 1,2,4-trimethylbenzene, 1,3,5-trimethylbenzene, methylene chloride, dichloroethane, and dimethyl adipate. The solvents usable in the invention are not limited to the above-described ones.

Materials Usable for Electrode

As electrodes (source electrode, drain electrode, gate electrode of the organic semiconductor device of the invention and/or cathode electrode and anode electrode of the organic electroluminescence device of the invention), conductive alloys, metal oxide films and thin metal films are employed. Examples of a metal used as the electrodes include Period 2 elements such as Li and Be, Period 3 elements such as Na, Mg and Al, Period 4 elements such as K, Ca, Sc, Ti, V, Cr, Mn, Fe, Co, Ni, Cu, Zn, Ga, Ge and Se, Period 5 elements such as Ag, Au, Pb, Rb, Sr, Y (this Y representing yttrium), Zr, Nb, Mo, Tc, Ru, Rh, Pt, Cd, In, Sn, Sb and Te, Period 6 elements such as Ba, Hf, Cs, Ir, Ta, W, Os, Hg, Tl and Bi, lanthanoid series elements such as La, Ce, Pr, Nd, Pm, Sm, Eu, Gd, Tb, Dy, Ho, Er, Yb and Lu and actinoid series elements such as Ac, Th, Pa, U, Np, Pu, Am, Cm, Bk, Cf and Es. Of these, Cr, Ta, W, Al, Mo, Ni, Au, Ag, Pt and Cu are preferred. As the metal compound, electrically conductive metal oxides such as tin oxide, zinc oxide, indium oxide, indium tin oxide (ITO) and alloys, mixtures or laminates of a metal such as gold, silver, chromium, nickel, tantalum, tungsten or molybdenum can be used, for example. From the viewpoints of electrical conduction and transparency, ITO is particularly preferred. A self assembled film and/or a film of a metal and/or metal compound may be coated on the surface of the electrode. Any known process is employed for the formation of the electrode and the electrode may be subjected to surface treatment such as ion beam, electroplating, electroless plating, anodization or chemical conversion treatment.

The electrode is doped by ion implantation, plasma doping (pulse modulation high-frequency plasma), vapor phase doping, solid phase doping, laser doping or the like method and mobility of electrons and/or holes from the electrode can be improved. During doping, only some electrodes can be surface-treated or doped by covering TFT with an interlayer insulating layer composed of a resist or the like. This makes it possible to minimize the influence of doping to TFT and at the same time, carry out surface treatment or doping of the electrode without deteriorating the switching function of TFT. When metallization can be carried out by a special epitaxial growth method over a silicon substrate having a surface with uniform crystal orientation, doping can be carried out during the epitaxial growth.

Gate Electrode

Gate electrodes are usually formed using a metal film such as aluminum or chromium. They may be made of a conductive polymer such as polyaniline or polythiophene, or formed by applying a conductive ink. These electrodes have an advantage of convenient formation because similar to the above-described alignment film (alignment layer), they can be formed by the application method.

When metal films are formed as electrodes (such as gate electrode, source electrode and drain electrode), the conventional vacuum film formation method, more specifically, mask film formation or photolithography can be employed. In this case, examples of the materials for the electrode formation include metals such as gold, platinum, chromium, palladium, aluminum, indium, molybdenum, nickel, tungsten and tantalum, alloys thereof, and inorganic materials such as polysilicon, amorphous silicon, tin oxide, indium oxide, zirconium oxide, yttrium oxide, and indium-.tin oxide (ITO). Two or more of these materials may be used in combination. The materials usable as the electrodes are not limited to the above-described ones. An electrode pattern may be formed by vacuum film formation via a mask or by patterning a film, which has been formed by vacuum film formation, using a resist. The electrode pattern formation method is not limited to them. As another method, printing method (including microcontact printing) can also be employed.

The thickness of the gate electrode differs depending on the electrical conductivity of the material used therefor. It is preferably from about 20 to 1100 nm. The lower limit of the thickness of the gate electrode differs depending on the electrical conductivity of the electrode material and adhesion strength with an underlying substrate. The upper limit of the thickness of the gate electrode is, on the other hand, the thickness at which a step difference between the underlying substrate and gate electrode is covered sufficiently with a gate insulating layer when the gate insulating layer and a pair of source and drain electrodes are formed, and disconnection of an electrode pattern is prevented. Particularly when a substrate with flexibility is employed, a stress balance must be taken into consideration.

Drain Electrode and Source Electrode

The drain electrode and source electrode are formed preferably using a metal having a large work function or are preferably electrodes having, on the surface thereof, a metal having a large work function, because the materials constituting the semiconductor layer, which will be described later, have holes as a charge transporting carrier so that ohmic contact with the semiconductor layer is required. The term "work function" as used herein means a potential difference necessary for withdrawing electrons to the outside from the solid and it is defined as an energy difference between vacuum level and Fermi level. A preferred work efficiency is from about 4.6 to 5.2 eV Specific examples of such a metal include gold, platinum and transparent conductive film (indium-tin oxide, indium.zinc oxide or the like). A transparent conductive film can be formed by sputtering or electron beam (EB) deposition. The thickness of the drain electrode and source electrode usable in the invention is from about 20 to 1100 nm. The distance (channel length) between the source and drain electrodes is from about 0.14 to 30 μm.

Annealing

The electrode may be annealed. Annealing of the electrode sometimes decreases a work function. Annealing may be conducted plural times and in this case, plural times of annealing may be conducted by the same or different methods during the formation of a layer. Annealing may be conducted during the above-described magnetization.

Examples of annealing include beam annealing, transient annealing and furnace annealing. The annealing temperature is preferably adjusted to not greater than the upper temperature limit of the substrate. This however does not apply to the case where limited heating of the electrodes can be effected by laser ablation. For example, beam annealing is carried out by exposure to line beam from a XeCl excimer laser light source at a fluence of from about 250 to 400 mJ/cm$^2$.

Work Function of Electrode

The work function on the surface of the electrode can be measured using a measuring instrument "AC-1" (trade name; product of Riken Keiki), or using absorption spectrum, ultraviolet photoelectron spectroscopy (UPS) or photoelectron spectroscopy. The work function of the surface modification layer on/above the surface of the electrode (for example, drain electrode and source electrode in the organic semiconductor device) used in the invention has an absolute value not greater than 4.0 eV but 0.1 eV or greater, preferably not greater than 3.5 eV but 0.1 eV or greater, more preferably not greater than 3.0 eV but 0.1 eV or greater. The organic semiconductor device and/or organic electroluminescence device formed using a surface modification layer having a work function falling within the above-described range has an advantage of high mobility in the semiconductor layer and low electrical resistance.

Surface Modification Layer Formed on Electrode Surface

A description will next be made of the surface modification layer for modifying the surface of each of the source electrode, drain electrode and gate electrode of the organic semiconductor device of the invention and/or the cathode electrode and anode electrode of the organic electroluminescence device of the invention which will be described next.

The term "surface modification layer" as used herein means a layer constituting a portion of an electrode layer, having a function of improving the mobility of electrons and/or holes in the semiconductor layer and/or emissive layer and having an effect of decreasing a drive voltage. As described above, it is said that the greater the work function of the source electrode and drain electrode in the organic semiconductor device, the higher the mobility in the semiconductor layer. The surface modification layer of the electrode layer formed by a magnetic material is effective for withdrawing charges to the side of the semiconductor layer by the influence of the Lorentz force. Effect in addition to the effect of the work function facilitates injection of charges from the electrode layer to the semiconductor layer, which can improve the mobility further.

The surface modification layer may cover therewith the entire surface of the electrode or a portion of the electrode.

In the source electrode and drain electrode having thereon a surface modification layer made of a magnetic material, when the magnetic materials have magnetic anisotropy in the same direction (for example, perpendicular to the substrate), the Lorentz force is applied to a direction so that holes and electrons face each other only when an electric current runs from the same direction. As a result, the mobility can be improved. In short, it is necessary to introduce holes and electrons from different directions in the drain electrode and source electrode. The electrodes are therefore preferably arranged like a comb, but the electrodes of the organic semiconductor device of the invention are not necessarily limited thereto.

The above-described electrodes (source electrode, drain electrode and gate electrode of the organic semiconductor device of the invention, and/or cathode electrode and anode electrode of the organic electroluminescence device of the invention) may have a migration inhibiting layer, capping layer and insulating layer further, depending on the using purpose.

The migration inhibiting layer has a function of inhibiting the components of the surface modification layer from being transported to the side of the electrode and mixing and/or improving the adhesion with the electrode. The capping layer has a function of isolating the surface modification layer from the outside to prevent its oxidation.

Two or more layers may be employed for each of the electrode, surface modification layer, migration inhibiting layer and/or capping layer. In order to improve the adhesion with the electrode or charge transfer from the electrode, an interlayer insulating layer of 2 nm or less thick may be laid on the interface between the electrode and the surface modification layer. The stacking order or number or thickness of the layers may be selected and used as needed in consideration of the mobility, electrical resistance, device brightness or device life.

In the organic semiconductor device and/or organic electroluminescence device of the invention, examples of the constitution of the electrode layer including the surface modification layer are shown below in a) to d). The slash "/" means that two layers with/therebetween are stacked adjacent to each other.
a) surface modification layer/electrode
b) surface modification layer/migration inhibiting layer/electrode
c) capping layer/surface modification layer/electrode
d) capping layer/surface modification layer/migration inhibiting layer/electrode Surface Modification Layer The surface modification layer is formed on the electrode directly or via the migration inhibiting layer to efficiently transfer charges fed from the electrode to the semiconductor layer or emissive layer. Its thickness is usually from 1 to 1000 nm, preferably from 5 to 100 nm. The surface modification layer containing a magnet, preferably containing a ferromagnet (permanent magnetic material) or having magnetic anisotropy is used for the organic semiconductor device of the invention. In the surface modification layer containing a permanent magnetic material, rare earth permanent magnet, nanocomposite magnet, PtCo alloy, SmCo alloy, NdCo alloy and the like can be used as the permanent magnetic material. The ferromagnets (magnets) usable for the surface modification layer will next be described. The invention is not limited to the below-described ferromagnets (magnets).

Nanocomposite Magnet

As the nanocomposite magnet, Nd and Sm rare earth elements are preferred. Of these, Nd series materials containing neodymium (Nd), iron (Fe) and boron (B) and Sm series materials containing samarium (Sm), cobalt (Co), copper (Cu) and iron (Fe) are preferred. Of these, Sm series materials are preferably employed owing to their rust resistance.

Specific examples of the nanocomposite magnet include $Nd_4Fe_{80}B_{20}$, $Nd_{4.5}Fe_{73}Co_3GaB_{18.5}$, $Nd_{5.5}Fe_{66}Cr_5Co_3GaB_{18.5}$, $Nd_{10}Fe_{74}Co_{10}SiB_5$, and $Sm_7Fe_{93}N_x$ (x standing for any integer greater than 0).

The nanocomposite magnet is not necessarily homogeneous in each portion of the structure of nano unit and usually, it has a commitment point (hard phase) and spring (soft phase), while forming a sea-island or layered structure. Such a magnet is called "exchange spring magnet" and exchange interaction occurs between phases (particles). The hard phase is not necessarily be composed of a rare earth magnet, but preferably is composed of $Ni_{0.8}Fe_{0.2}$, $Nd_2Fe_{14}B$, or $Sm_2Fe_{14}Nx$ (wherein $0<x\leq3$), while the soft phase is preferably composed of SmCo, $Fe_3B$ or α-Fe, or mixture thereof.

Rare Earth Permanent Magnet

Preferred examples of a rare earth ferrous magnet include Sm—Co series, Ce—Co series and Sm—Fe series. Their crystal structure may be either a $JCO_5$ type or $J_2Co_{17}$ type (rare earth element will hereinafter be abbreviated as "J"). They also include Sm, Nd and compounds obtained by doping thereinto nitrogen, boron and/or carbon.

$SmCo_5$ and $CeCo_5$ are typical examples having the $JCo_5$ type crystal structure. Additional examples include $YCo_5$, $LaCo_5$, $PrCo_5$, $NdCo_5$, $GdCo_5$, $TbCo_5$, $DyCo_5$, $HoCo_5$, $ErCo_5$ and $TmCo_5$.

$Sm_2Co_{17}$ is a typical example having the $J_2Co_{17}$ type crystal structure, and additional examples include $Y_2Co_{17}$, $La_2Co_{17}$, $Pr_2Co_{17}$, $Nd_2Co_{17}$, $Gd_2Co_{17}$, $Tb_2Co_{17}$, $Dy_2Co_{17}$, $Ho_2Co_{17}$, $Er_2Co_{17}$ and $Tm_2Co_{17}$.

As the alloy composition having nitrogen (N) doped therein, $J_2Fe_{17}N_x$ (wherein $0<x\leq3$, and J represents a rare earth element) can be given as an example: Specific examples include $Ce_2Fe_{17}N_3$, $Pr_2Fe_{17}N_3$, $Nd_2Fe_{17}N_3$, $Pm_2Fe_{17}N_3$, $Sm_2Fe_{17}N_3$, $Eu_2Fe_{17}N_3$, $Gd_2Fe_{17}N_3$, $Tb_2Fe_{17}N_3$, $Dy_2Fe_{17}N_3$, $Ho_2Fe_{17}N_3$, $Er_2Fe_{17}N_3$, $Tm_2Fe_{17}N_3$, $Yb_2Fe_{17}N_3$, and $Lu_2Fe_{17}N_3$.

As the alloy composition having carbon (C) doped therein, $J_2Fe_{17}C_x$ (wherein $0<x\leq3$, and J represents a rare earth element) and $J_2Fe_{14}C_x$ (wherein $0<x\leq1$, and J represents a rare earth element) can be given as examples. Specific examples of $J_2Fe_{17}C_x$ include $La_2Fe_{17}C_3$, $Y_2Fe_{17}C_3$, $Ce_2Fe_{17}C_3$, $Pr_2Fe_{17}C_3$, $Nd_2Fe_{17}C_3$, $Pm_2Fe_{17}C_3$, $Sm_2Fe_{17}C_3$, $Eu_2Fe_{17}C_3$, $Gd_2Fe_{17}C_3$, $Tb_2Fe_{17}C_3$, $Dy_2Fe_{17}C_3$, $Ho_2Fe_{17}C_3$, $Er_2Fe_{17}C_3$, $Tm_2Fe_{17}C_3$, $Yb_2Fe_{17}C_3$, $Lu_2Fe_{17}C_3$, and $Th_2Fe_{17}C_3$. Specific examples of $J_2Fe_{14}C_x$ include $La_2Fe_{14}C$, $Y_2Fe_{14}C$, $Ce_2Fe_{14}C$, $Pr_2Fe_{14}C$, $Nd_2Fe_{14}C$, $Pm_2Fe_{14}C$, $Sm_2Fe_{14}C$, $Eu_2Fe_{14}C$, $Gd_2Fe_{14}C$, $Tb_2Fe_{14}C$, $Dy_2Fe_{14}C$, $Ho_2Fe_{14}C$, $Er_2Fe_{14}C$, $Tm_2Fe_{14}C$, $Yb_2Fe_{14}C$, $Lu_2Fe_{14}C$, and $Th_2Fe_{14}C$.

As the alloy composition having boron (B) doped therein, $J_2Fe_{14}Bx$ (wherein $0<x\leq1$, and J represents a rare earth element) can be given as an example. Specific examples include $La_2Fe_{14}B$, $Y_2Fe_{14}B$, $Ce_2Fe_{14}B$, $Pr_2Fe_{14}B$, $Nd_2Fe_{14}B$, $Pm_2Fe_{14}B$, $Sm_2Fe_{14}B$, $Eu_2Fe_{14}B$, $Gd_2Fe_{14}B$, $Tb_2Fe_{14}B$, $Dy_2Fe_{14}B$, $Ho_2Fe_{14}B$, $Er_2Fe_{14}B$, $Tm_2Fe_{14}B$, $Yb_2Fe_{14}B$, $Lu_2Fe_{14}B$, and $Th_2Fe_{14}B$. In order to improve corrosion resistance, a portion of B may be substituted with C.

In the above-described $JCO_5$ (J representing a rare earth element), a portion of Co may be substituted with Cu. For example, $J(Co_{1-x}Cu_x)5$ (wherein $0.01<x<0.99$) can also be used in the invention. A stable electrode is available by heat treating it. Specific examples include $Ce(Cu_{0.86-x}Fe_{0.14}Cu_x)_5$ {wherein $0<x<0.86$}, $Ce(Cu_{0.72}Fe_{0.14}Cu_{0.14})_5$ and $Ce(Cu_{0.72}Fe_{0.14}Cu_{0.14})_5$.

Sm Series Permanent Magnet

As the Sm-series permanent magnet, materials containing Sm, Co, Fe and Cu are preferred. Their alloy composition is preferably $Sm(Cu_{0.94-x}Fe_{0.06}Cu_x)_{6.8}$ {wherein $0.1<x<0.93$}.

An alloy composition obtained by adding Zr to the above-described composition can also be used. Examples include $Sm(Cu_{0.88-x}Fe_{0.11}Cu_xZr_{0.01})_{7.4}$ {wherein $0<x<0.88$}, $Sm(Cu_{0.765-x}Fe_{0.22}Cu_xTi_{0.015})_{7.2}$ {wherein $0<x<0.765$}, $Sm(Cu_{0.75-x}Fe_{0.22}Cu_xTi_{0.03})_{7.2}$ {wherein $0<x<0.75$}, $Sm(Cu_{0.745-x}Fe_{0.20}Cu_{0.055}Zr_x)_{7.5}$ {wherein $0<x<0.745$}, Sm(Co$_{0.73-x}$Fe$_{0.20}$Cu$_x$Zr$_{0.02}$)$_y$ {wherein $0<x<0.73$, $0.<y<8.5$}, and Sm(Cu$_{0.69-x}$Fe$_{0.2}$Cu$_x$Zr$_{0.01}$)$_{7.2}$ {wherein $0<x<0.69$}. Specific examples include Sm(Cu$_{0.69}$Fe$_{0.2}$Cu$_{0.1}$Zr$_{0.01}$)$_{7.45}$.

The alloy composition in the Sm$_2$Co$_{17}$ series magnet is for example Sm(Co$_{1-x-y-b}$Fe$_x$Cu$_y$Zr$_b$)$_a$ {wherein $0<x<1$, $0<y<1$, $0<a<1$, and $0<b<1$}. Specific examples include Sm(Cu$_{0.925-x}$Fe$_x$Cu$_{0.055}$Zr$_{0.02}$)$_z$ {wherein $0<x<0.925, 0<z<8.5$}, Sm(Cu$_{0.72}$Fe$_{0.20}$Cu$_{0.055}$Zr$_{0.025}$)$_{7.5}$, Sm(Cu$_{0.65}$Fe$_{0.21}$Cu$_{0.05}$Zr$_{0.02}$)$_{7.65}$, Sm(Cu$_{0.69}$Fe$_{0.20}$Cu$_{0.10}$Zr$_{0.01}$)$_{7.4}$, and Sm(Cu$_{0.625}$Fe$_{0.3}$Cu$_{0.05}$Zr$_{0.025}$)$_{7.6}$. More specific examples include (Sm$_{0.70}$Ce$_{0.30}$)(Cu$_{0.72}$Fe$_{0.16}$Cu$_{0.12}$)$_7$, Ce(Cu$_{0.73}$Fe$_{0.12}$Cu$_{0.14}$Ti$_{0.01}$)$_{6.5}$, Ce(Cu$_{0.72}$Fe$_{0.14}$Cu$_{0.14}$)$_{5.2}$, SM$_{0.6}$Gd$_{0.4}$Co$_5$, Pr$_{0.6}$Sm$_{0.4}$Co$_5$, Sm$_2$Fe$_{17}$, Sm$_8$Zr$_3$Fe$_{85}$Co$_4$, (Sm$_8$Zr$_3$Fe$_{85}$Co$_4$)N$_{15}$, and Sm$_2$Fe$_{17}$Nx(wherein $0<x<3$).

JFe$_{11}$Ti (wherein $0<x<3$) and the like have an effect of stabilizing a magnetic field because an element other than iron is introduced. Alloys obtained by doping these alloys with nitrogen, boron and/or carbon can also be used. Examples of them include NdFe$_{11}$TiN$_x$ (wherein x stands for any integer greater than 0) and (Sm$_8$Zr$_3$Fe$_{84}$)$_{85}$N$_{15}$.

As the J(Fe$_{1-x}$Tx)$_{12}$ {wherein J stands for a rare earth element and T represents Ti, Mo or the like} series magnet, JFe$_{11}$Ti, JFe$_{11}$Mo and JFe$_{11.5}$Mo$_{0.5}$ can be used. Specific examples include SmFe$_{11}$Ti, YFe$_{11}$Ti, NdFe$_{11}$Ti, SmFe$_{11}$Ti, GdFe$_{11}$Ti, TbFe$_{11}$Ti, DyFe$_{11}$Ti, HoFe$_{11}$Ti, ErFe$_{11}$Ti, TmFe$_{11}$Ti, and LuFe$_{11}$Ti.

Examples of the alloy composition of JCo$_{11}$Ti (wherein J represents a rare earth element) series magnet include SmCo$_{11}$Ti, YCo$_{11}$Ti, NdCo$_{11}$Ti, SmCo$_{11}$Ti, GdCo$_{11}$Ti, TbCo$_{11}$Ti, DyCo$_{11}$Ti, HoCo$_{11}$Ti, ErCo$_{11}$Ti, TmCo$_{11}$Ti, and LuCo$_{11}$Ti.

As the magnetic material, a solid solution of the above-described JCo$_{11}$Ti (wherein J represents a rare earth element) and JFe$_{11}$Ti (wherein J represents a rare earth element) can also be used. As the JFe$_2$ {wherein $7<z<11$ and J represents a rare earth element} series alloy composition, (JZr)(FeCo)$_z$ {$7<z<12$ and J represents a rare earth element} can be given as an example. The alloy composition obtained by nitriding a quenched thin body of it is for example (J$_{0.75}$Zr$_{0.25}$)(Fe$_{0.7}$CO$_{0.3}$)$_z$N$_x$.

Nd Series Permanent Magnet

Examples of Nd series permanent magnet include Nd$_{1.1}$Fe$_4$B$_4$, Nd$_7$Fe$_3$B$_{10}$, and Nd(Fe$_{1-x}$Co$_x$)$_{14}$B {wherein $0<x<1$}, while examples of Nd—Fe—B series spring magnet include Nd$_{4.5}$Fe$_{77}$B$_{18.5}$, Nd$_{4.5}$Fe$_{74}$Co$_5$B$_{18.5}$, Nd$_{4.5}$Fe$_{73}$Co$_3$SiB$_{18.5}$, Nd$_{4.5}$Fe$_{73}$Co$_3$GaB$_{18.5}$, Nd$_3$.5DyFe$_{73}$Co$_3$GaB$_{18.5}$, Nd$_{5.5}$Fe$_{71}$Cr$_5$B$_{18.5}$, Nd$_{5.5}$Fe$_{66}$Cr$_5$Co$_5$B$_{18.5}$, and Nd$_{4.5}$Fe$_{73}$V$_3$SiB$_{18.5}$ Of the above-described permanent magnetic materials, rare earth magnets are most effective, but Zr and Y can also be used. Magnets weaker than rare earth magnets or rare earth ferrous magnets, for example, platinum iron series, alnico series, ferrite series, platinum cobalt series, chromium steel series, steel cobalt series, magnetite series, NKS steel series, MK steel series, KS steel series and OP series magnets are also usable.

Principal elements used for such alloy composition are mainly 3d transition metals such as Fe, Ni and Co and 4f rare earth metals such as Nd and Sm or Tb and Dy. The composition of a ferrite magnet is, for example, BaO.6Fe$_2$O$_3$, SrO.6Fe$_2$O$_3$, or PbO.6Fe$_2$O$_3$. In addition, Fe$_{16}$N$_2$ and Fe$_{16}$B$_2$ are also popularly known. A magnet is available by the deposition of Fe in an N$_2$ atmosphere.

Although Ca, B and C are each a non-magnetic element, when a solid solution of Ca, B and C is formed into a thin film, a magnetic susceptibility of the surface increases. This also applies to a solid solution of Ca, La and B. Such a phenomenon can also be observed in QB$_2$C$_2$ and JB$_2$C (Q representing an alkali metal and/or alkaline earth metal) composed of an alkaline earth metal, alkali metal, boron, carbon or the like. An alloy composition such as La$_{1-x}$Ca$_x$MnO$_2$ can be given as this example.

Such a nonmagnetic element acquires magnetism in a nanostructure because properties exhibited in a small cluster size are different from those in the form of a bulk. Ordinarily used BaO, Li$_2$O, MgO, Sm$_2$O$_3$ and Yb$_2$O$_3$ can also be used. Examples of another alloy composition capable of carrying out surface modification include binary type compositions such as GdCo, TbFe, GdFe, DyFe, MnBi and MnZn and multicomponent compositions such as GdTbFe, TbFeCo, GdFeCo, and GdTbFeCo. JFe$_2$ series magnetostrictive materials such as TbFe$_2$, DyFe$_2$, ErFe$_2$, TmFe$_2$, SmFe$_2$, Tb$_x$Dy$_a$Fe$_z$ ($0.27<x<0.3$, $0.7<z<0.73$, $1.9<a<2.0$) can also be used. A thin film of such a composition may be formed on the surface. When the surface modification layer is a film which can be epitaxially grown, it may be formed on an epitaxially grown film and a wiring metal film which have been stacked one after another. The surface modification layer which can be epitaxially grown is composed of, for example, (ZrO$_2$)$_{1-x}$(Y$_2$O$_3$)$_x$ {wherein $0<x<1$}.

Superconducting Magnet

Examples of the alloy composition of a superconducting magnet include Nb, Pb, NbTi, NbN, Nb$_3$Sn, Nb$_3$Al, V$_3$Ga, (La$_{1-x}$Sr$_x$)$_2$CuO$_4$ {wherein $0<x<1$}, La$_2$CuO$_4$, Sr$_2$CuO$_4$, LaSrCuO$_4$, JBa2Cu$_3$O$_x$ (wherein J represents a rare earth element, for example, Y, La, Nd, Sm, Eu, Gd, Dy, Ho, Er, Tm or Yb and $7<x<8$), (Bi$_{1-x}$Pb$_x$)$_2$Sr$_2$Cu$_3$O$_{10}$ {wherein $0<x<1$}, Bi$_2$Sr$_2$Cu$_3$O$_{10}$, Pb$_2$Sr$_2$Cu$_3$O$_{10}$, BiPbSr$_2$Cu$_3$O$_{10}$, Tl$_2$Ba$_2$Ca$_2$Cu$_3$, and HgBa$_2$Ca$_2$Cu$_3$O$_x$ (x stands for any integer of 0 or greater).

A pinning effect as can be observed in a superconducting magnet may be used for controlling the composition of a magnet, for example, by dispersing a hetero phase therein. It can be attained by adopting a method of forming a nonmagnetic composition before or after the formation of a magnetic composition.

Surface Modification Layer

The surface modification layer in the organic semiconductor device or organic electroluminescence device according to the invention is preferably composed of a layer made of a permanent magnetic material as described above. It causes surface polarization and has an electrical dipole moment. Particularly in the invention, the surface modification layer may have a magnetic dipole moment in a direction perpendicular to the substrate or in a direction parallel to the opposing faces (e.g. along the opposing faces) of the source electrode and the drain electrode so that electrons and/or holes are easily withdrawn in a direction of the opposing axis (that is, in a direction parallel to the substrate and vertical to the electrode (for example, a direction perpendicular to a long-side direction of a comb-shaped electrode)} of it, which improves the mobility in the semiconductor layer and/or emissive layer, thereby facilitating a reduction in the drive voltage.

This phenomenon will next be described specifically. When the surface modification layer shows magnetic anisotropy, it means that there exists a magnetic dipole moment in a direction perpendicular to the surface of the surface modification layer, that is, in an in-plane of the surface modification layer. The magnetic dipole moment in a direction perpendicular to the substrate acts so as to withdraw electrons from the electrodes in a direction of an opposing axis to both electrodes (for example, comb-shaped drain electrode and comb-shaped source electrode). The force appears in a direction vertical to both the direction of charges running through the electrodes and the direction of a magnetic force caused by magnetic anisotropy, whereby the force in a direction of an opposing axis to the both electrodes is applied to electrons running through the electrodes and charges are withdrawn from the electrodes. The charges thus withdrawn are released to the semiconductor layer so that the surface modification layer having such a magnetic dipole moment has both high mobility and low electrical resistance.

The force applied to electrons can be explained by the Lorenz force. Supposing that a force for withdrawing electrons is F, charge is q, and charge transfer rate is v, $F=q(v \times B)$. A magnetic field H formed by a magnetic dipole moment M at a position vector r has the following relation: $H=-\frac{1}{4} \times (\pi \mu) \text{grad}(Mr/r^3)$, and $B=\mu H$. The greater the magnetic dipole moment M (that is, the greater the magnetic anisotropy), the greater the electron withdrawing force, which leads to an increase in the mobility.

As in "Electronic Structure of Vanadium Cluster Anions-Measured and DV-Xα Calculation of Photoelectron Spectra" included in M. Iseda, T. Nishio, H. Yoshida, A. Terasaki, and T. Kondow, *RITU*, 4(2), 215(1996), the state of electrons can be investigated by the photoelectron spectroscopy after mass selection of clusters, and magnetic anisotropy depending on the cluster size can be forecasted to some extent by simulating the respective energy levels for up spin and down spin by the DV-Xα method.

In the invention, regular defects may be formed by exposing the above-described surface modification layer to Ar ions. By forming defects in the surface modification layer, the surface of the surface modification layer can be polarized to reduce a work function further. Such a reduction in work function caused by surface polarization facilitates withdrawing of electrons from the electrode, bringing further improvement in electron release efficiency.

Magnetization Method or Orientation Control Method

The surface modification layer is preferably magnetized or orientation-controlled in order to impart it with magnetic anisotropy or increase its magnetic anisotropy. The magnetization or orientation control of the surface modification layer is accomplished by a method using a magnetostatic field or a pulsed magnetic field, field cooling magnetization or zero field cooling magnetization.

As the method using a magnetostatic field, there is, for example, a method of placing strong magnets around the surface modification layer which is to be magnetized or orientation-controlled. This method enables to control the orientation direction of the surface of the surface modification layer. As the magnetization method by using a pulsed magnetic field, a method of placing a strong coiled electromagnet outside the sample and sending a current to the coil while synchronizing with a pulse. The orientation direction of the surface modification layer may also be controlled by this method. The magnetization by a pulsed magnetic field has merits in high mass productivity because magnetization can be completed in a short time and a pulse width can be changed. At this time, a direct current can be sent to the coil. The surface modification layer can also be magnetized using a superconducting permanent magnet.

The magnetic field applied to magnetize or orientation-control the surface modification layer is preferably 0.01 T (Tesla) or greater but not greater than 15T, more preferably 1T or greater but not greater than 15T, especially preferably 5T or greater but not greater than 15T.

The coercive force of the surface modification layer is preferably $7.96 \times 10^3$ A/m (100 Oersted) or greater, more preferably $7.96 \times 10^4$ A/m (1000 Oersted) or greater, especially preferably $7.96 \times 10^5$ A/m (10000 Oersted). The magnetism of the surface modification layer, which is a thin film, is measured by a vibrating sample magnetometer commonly known as VSM.

The magnetization or orientation control of the surface modification layer may be performed during or after film formation. If necessary, the layer may be annealed during magnetization.

Annealing temperature falls within a range of from 300 to 1200° C., preferably from 300 to 1000° C., more preferably from 300 to 600° C.

Compound/Compound Layer

In the structure of the organic semiconductor device or organic electroluminescence device of the invention, each of the below-described compounds can be incorporated in the surface modification layer or a layer composed of the below-described compound can be formed on one or both surfaces of the surface modification layer. When a layer composed of the compound is formed over one or both surfaces of the surface modification layer, its thickness is set in consideration of the resistance or magnetic anisotropy which varies depending on the kind of the compound layer. Usually, the thickness of from 10 to 2000 nm is preferred, with that of from 500 to 1500 nm being more preferred. The thickness within the above-described range is effective for exhibition of stable electron release performance. When the compound is incorporated in the surface modification layer, its content is set in consideration of the resistance, magnetic anisotropy or the size of crystal grain boundary which varies depending on the kind of the compound. The compound is usually added in an amount of from 0.1 to 50 wt %, preferably from 2 to 20 wt. % based on the total weight of the surface modification layer. The content within the above-described range is effective for forming an impurity level for heightening the electron release performance and at the same time, reducing a work function.

One or more compound materials selected from the group consisting of metal oxides, metal hydroxides, metal fluorides, metal carbides, metal nitrides, metal borides, metal phosphides, metal silicides, inorganic defects formed by ion irradiation and organic defects formed by ion irradiation can be used as such a compound. One or more metal elements selected from the group consisting of alkali metals, alkaline earth metals, lanthanoid metals, transition metals of Period 4 and transition metals of Period 5 can be used as a metal element contained in these compound materials. Inorganic defects formed by ion irradiation include, for example, defect films of diamond carbon and defect films of ZnO.

Migration Inhibiting Layer and Capping Layer

A migration inhibiting layer may be disposed between the surface modification layer and electrode and/or a capping layer may be disposed on the surface modification layer.

The migration inhibiting layer is a layer for inhibiting the components of the compound forming the surface modification layer from transferring to the side of the electrode. As materials for constituting the migration inhibiting layer having a large work function and high electrical conduction, titanium, aluminum, silver, copper, iron, platinum and gold and/or mixture thereof are preferred. The thickness of the migration inhibiting layer is usually from several hundred Å (several ten nm) or greater and is often about several thousand Å (several hundred nm).

The capping layer is composed of a metal with a great work function and it is disposed on the surface modification layer to provide continuous electrical connection to the surface modification layer. The capping layer is made of, for example, a material such as platinum, gold or silver. It usually has thickness preferably from 1 to 100 nm.

As described above, when the organic semiconductor device and/or organic electroluminescence device according to the invention has a film with magnetic anisotropy as the surface modification layer, the mobility of charges and electrical conducting performance are improved by the Lorenz force, resulting in a substantial reduction in work function. In addition, magnetic materials tend to form a stable film as the surface modification layer. As a result, the organic semiconductor device and or/organic electroluminescence device having an electrode which is driven by a low voltage and stable while having high mobility is available. Moreover, a cathode with less time-dependent change and resistant to oxidation is available by the structure in which a migration inhibiting layer, capping layer and insulating layer are used in combination.

Gate Insulating Layer

A gate insulating layer is preferably formed using an existing patterning process such as CVD (Chemical vapor deposition). When it is employed, an inorganic material such as $SiO_2$, SiNx, $Al_2O_3$, $Ta_2O_5$, $ZrO_2$, $La_2O_3$ or doped Si is preferably employed. These materials may be used in combination of two or more, for example, as a mixture or laminate.

The gate insulating layer may be formed by applying an organic material similar to formation of the above-described gate electrode. Examples of the organic material usable here include polychloropyrene, polyethylene terephthalate, polyoxymethylene, polyvinyl chloride, polyvinylidene fluoride, cyanoethyl pullulan, polymethyl methacrylate, polysulfone, polycarbonate and polyimide.

The mobility of the organic semiconductor device depends on the field intensity so that the gate insulating layer has a thickness of from 20 nm to 500 nm, preferably from 40 to 310 nm. The dielectric breakdown at this time is desirably 1.9 Mv/cm or greater.

Interlayer Insulating Layer

The organic semiconductor device has preferably an interlayer insulating layer. The interlayer insulating layer is formed in order to prevent the surfaces of a drain electrode and a source electrode from being contaminated when they are formed on the gate insulating layer. In the bottom gate type (inverted staggered structure type) organic semiconductor device, the interlayer insulating layer is formed on the gate insulating layer prior to the formation of a drain electrode and a source electrode. After formation of the drain electrode and source electrode, a portion of the interlayer insulating layer disposed on/above a channel region is completely or partially removed. A region of the interlayer insulating film to be removed is preferably equal in size to the gate electrode.

Examples of materials constituting the interlayer insulating layer include organic materials such as SiO, SiNx, $Al_2O_3$, $Ta_2O_5$, $ZrO_2$, $La_2O_3$ and doped Si, and organic materials such as polychloropyrene, polyethylene terephthalate, polyoxymethylene, polyvinyl chloride, polyvinylidene fluoride, cyanoethyl pullulan, polymethyl methacrylate, polysulfone, polycarbonate and polyimide. The invention is however not limited to them.

Protection Layer

After the formation of the electrode, it is desirable to form a protection layer or cover on the electrode in order to protect the organic semiconductor device. This enables stable use of the organic semiconductor device for a long period of time. The protection layer acts to protect the organic semiconductor device from the outside influence. As the protection layer, polymer compounds, metal oxides, metal fluorides, metal borides, silicon oxide and silicon nitride suited for the formation of it can be used. As the protection cover, glass plate, plastic plate (including sheet or film) having a surface subjected to hydraulic permeability reduction treatment. A method of hermetically sealing by putting this cover and the device together via a thermosetting resin or photosetting resin is preferably employed.

The organic electroluminescence device of the invention comprises a substrate, a cathode electrode, an emissive part and an anode electrode.

The term "emissive part" as used herein has a laminated structure having an emissive layer. The emissive part is a concept embracing not only the emissive layer but also an electron injection layer, electron transport layer, hole injection layer and a hole transport layer.

The emissive layer has a light emitting function. The hole transport layer transports holes, while the hole injection layer improves a hole injection efficiency from an anode (it is composed of, for example, a conductive polymer such as polyaniline derivative, polythiophene derivative, polyparaphenylene derivative, polyethylene vinylene derivative, polyvinyl carbazole derivative or polyvinyl indole derivative, a metal phthalocyanine derivative, A-NPD derivative or TPD derivative). The electron transport layer transports electrons, while the electron injection layer improves an electron injection efficiency from a cathode (it is composed of, for example, a phenanthrene derivative, perylene derivative, oxadiazole derivative, quinone derivative or anthracene derivative). In order to improve adhesion with the electrode or charge injection from the electrode, an insulating film (a metal oxide film, a metal fluoride or organic material) having a thickness not greater than 2 nm may be disposed adjacent to the electrode. It is also possible to insert a buffer layer between layers to improve adhesion of interface or prevent mixing. The order or number of the layers stacked and thickness of each layer can be determined as needed, in consideration of the luminous efficiency or emission lifetime.

A cathode electrode, emissive part and anode electrode can be arranged, for example, according to the below-described constitutions a) to d). The slash "/" means that two layers with/therebetween are stacked adjacently.

a) cathode electrode/emissive layer/anode electrode
b) cathode electrode/emissive layer/hole transport layer/ anode electrode
c) cathode electrode/electron transport layer/emissive layer/ anode electrode
d) cathode electrode/electron transport layer/emissive layer/ hole transport layer/anode electrode
e) cathode electrode/emissive layer/hole injection layer/ anode electrode
f) cathode electrode/electron injection layer/emissive layer/ anode electrode
g) cathode electrode/electron injection layer/emissive layer/ hole injection layer/anode electrode h) cathode electrode/electron injection layer/emissive layer/hole transport layer/anode electrode
i) cathode electrode/electron transport layer/emissive layer/hole injection layer/anode electrode
j) cathode electrode/emissive layer/hole transport layer/hole injection layer/anode electrode
k) cathode electrode/electron transport layer/emissive layer/hole transport layer/hole injection layer/anode electrode
l) cathode electrode/electron injection layer/emissive layer/hole transport layer/hole injection layer/anode electrode
m) cathode electrode/electron injection layer/electron transport layer/emissive layer/hole injection layer/anode electrode
n) cathode electrode/electron injection layer/electron transport layer/emissive layer/hole transport layer/anode electrode
o) cathode electrode/electron injection layer/electron transport layer/emissive layer/anode electrode
p) cathode electrode/electron injection layer/electron transport layer/emissive layer/hole transport layer/hole injection layer/anode electrode In the above-described constitution a), the emissive part is an emissive layer.

In the organic electroluminescence device of the invention, the emissive part contains the tertiary amine compound of the invention.

In the organic electroluminescence device of the invention, the tertiary amine compound of the invention may be contained in any one layer selected from the group consisting of emissive layer, electron injection layer, electron transport layer, hole injection layer and hole transport layer or may be contained in two or more layers of them.

The organic electroluminescence device of the invention preferably contains the tertiary amine compound of the invention and a metal complex in one layer.

Emissive Layer of Organic Electroluminescence Device

The emissive layer of the organic electroluminescence device of the invention can be formed using a metal complex or the tertiary amine compound as a host material and a metal complex as a guest material. The metal complex was already described above.

The host material is a main component of the emissive layer and the guest material is a secondary component.

As the host of the emissive layer, not only the tertiary amine compound of the invention, but also CBP, that is, {4,4'-bis(carbazol-9-yl)biphenyl}, a compound having a substituent soluble in CBP, a tertiary amine compound such as dendrimer containing a carbazole group or a polymer compound (conductive polymer such as polyaniline derivative, polyvinyl carbazole derivative or polyvinyl indole derivative) can be used. Examples of the guest material include metal complexes containing a metal such as Ir, Ru, Al, Ga, Mg, Be or Zn {for example, Ir(ppy)$_3$ and metal complexes having a substituent soluble in these ligands}.

Anode Electrode

The anode electrode (which is also called "positive electrode") of the organic electroluminescence device of the invention is preferably made of a material having a work function greater than about 4.5 eV Typical examples of the anode material include metal oxides such as ITO (indium-tin oxide) and IZO (indium-zinc oxide). Examples of the anode layer include thin metal films (such as aluminum, silver, platinum, gold, palladium, tungsten, indium, copper, iron, nickel, zinc, and lead), graphite and doped inorganic semiconductors (such as silicon, germanium and gallium arsenic). The metal anode is sufficiently thin so that it is semi-transparent to light. The anode is manufactured by a technology which is applied to the formation of a thin anode film constituting a light emitting device. The typical method was as described above. In such a manufacturing technology, a pure metal, alloy or another film precursor is, for example, employed. Typically, the anode layer is from about 100 nm to 2000 nm thick.

Cathode Electrode

The cathode electrode (which is also called "negative electrode") of the organic electroluminescence device of the invention is preferably made of a material having a work function not greater than about 3.0 eV The cathode is typically an electrode using an alkali metal or alkaline earth metal in combination with aluminum or silver, for example, an electrode obtained by capping Ca (film thickness: about 3 nm to 50 nm) with Al (film thickness: about 200 nm). The cathode is manufactured by a technology which is applied to the formation of a thin anode film constituting a light emitting device. The typical method was as described above. In such a manufacturing technology, a pure metal, alloy or another film precursor is, for example, employed. Typically in the cathode electrode, an alkali metal and/or alkaline earth metal layer has preferably a thickness of from about 1 nm to 50 nm and an Al or Ag layer for capping Ca has preferably a thickness of from about 50 nm to 2000 nm.

A description will next be made of the mode of the emissive layer when the tertiary amine compound is incorporated in the hole transport layer.

In the ordinary bottom emission structure, the emissive layer is stacked on the hole transport layer so that the emissive layer is formed by vapor deposition or application using a solvent which does not dissolve therein the hole transport layer. For the emissive layer, metal complexes such as the above-described Ir(ppy)$_3$, Alq$_3$ and bis(2-(2-hydroxyphenyl)-benzo-1,3-thiazolate) zinc complex and/or the tertiary amine compounds such as CBP are frequently used.

In the top emission structure, on the other hand, the hole transport layer is stacked on the emissive layer so that the hole transport layer is formed by vapor deposition or application using a solvent which does not dissolve therein the emissive layer. For the emissive layer, not only metal complexes such as the above-described Ir(ppy)$_3$, Alq$_3$ and bis(2-(2-hydroxyphenyl)-benzo-1,3-thiazolate) zinc complex and/or the tertiary amine compounds such as CBP but also polymer can be used.

A description will next be made of the mode of the hole transport layer when the tertiary amine compound of the invention is incorporated in the emissive layer.

When the emissive layer is formed by vapor deposition, no limitation is imposed on the formation of the hole transport layer. Any compound having a hole transporting property may be used for the hole transport layer.

When the emissive layer is applied using a solvent, the solvent which does not dissolve therein the hole transport layer must be used. In this case, a polymer film formed by an aqueous solution ("Baytron P CH-8000", trade name; product of Bayer) obtained by colloidal dispersion of PEDOT/PSS [poly(3,4-ethylenedioxythiophene)] which is a derivative of polythiophene sparingly soluble in an organic solvent and polystyrenesulfonic acid at a weight ratio of 20:1 can be used as the hole transport layer.

Film Formation Method

Next, the film formation method of each layer disposed in the organic semiconductor device and organic electroluminescence device of the invention will be described.

The electrode, compound layer, surface modification layer, migration inhibiting layer and capping layer can be formed by a variety of physical methods (physical vapor deposition) and chemical methods. Examples of the physical methods include vapor deposition, sputtering (DC sputtering, DC magnetron sputtering, RF sputtering, RF magnetron sputtering, facing target sputtering, ECR sputtering and ion beam sputtering), CVD, molecular beam epitaxy (MBE), spin coating, and method using an apparatus for ion beam deposition (IBD apparatus). Additional examples include laser abrasion (laser sputtering), electron beam deposition (EB method), vapor deposition using an arc plasma gun, ion assist vapor deposition, liquid molecular beam epitaxy, liquid phase epitaxy, hot wire cell (epitaxial growth), reactive deposition epitaxy (RDE), composition spreading, nitrogen atmosphere laser abrasion, pulse laser deposition, atmospheric pressure atomic layer deposition (AP-ALD), liquid molecular beam cluster deposition, plating, a method using thermal $SiO_2$ film, spraying, dipping (ITO method), sol-gel, ion plating and Langmuir-Blodgett method.

For the formation of various layers constituting the organic semiconductor device or organic electroluminescence device of the invention, various film formation methods embraced in the above-described methods can be adopted, but the invention is not limited thereto. If possible, the above-described methods can be used in combination.

As one example, for example, a metal oxide layer can be formed by thermal vapor deposition of a corresponding metal in pressure-controlled oxygen. The thickness of the metal oxide layer can be controlled by an evaporation/deposition rate or time. A typical evaporation/deposition rate is from about 0.2 to 1 Å (Å=0.1 nm) per second. In some cases, cluster ion beam obtained by ionization of clusters may be deposited after electrical neutralization and/or addition of an opposite charge.

The surface modification layer is preferably formed by vacuum arc deposition, particularly vacuum arc deposition using an arc plasma gun. This vacuum arc deposition is however limited by the use of a conductive substance (such as metal, conductive inorganic matter or carbon) as a deposition material. A drawback caused by the use of an arc plasma gun (product of ULVAC) is that large clusters (which have a particle size of about μm and may be called "macroparticles") are sometimes mixed in. In such a case, a thin film can be formed by bending the direction of ion beam and depositing ions on the substrate after neutralization and/or as are. The ultimate pressure of a vacuum chamber is preferably $1\times10^{-6}$ Pa or less, but even at the ultimate pressure exceeding the above-described range, the film can be formed. The film forming rate is from about 3.0 nm to 6.0 nm per minute. The upper limit of the ultimate pressure of the vacuum chamber is preferably $1\times10^{-4}$ Pa, more preferably $1\times10^{-5}$ Pa. This deposition rate is applied when a substrate to be deposited is 80 mm away from a deposition source and under such conditions, the in-plane distribution results in ±5% at Ø20 mm. The arc plasma gun can control a film thickness even within a range not greater than 1 nm and can maintain even 50000 times discharge while using carbon as a target. Preferred examples of another formation method of the surface modification layer include sputtering and MBE. A method relating to cluster growth by laser sputtering is described in J. P. Bucher, *Rev. Sci. Instrum.* 63, 5667(1992).

When the surface modification layer is formed by laser sputtering, conditions adopted therefor are: laser frequency of from 1 to 60 Hz and power of from 1 to 2000 $mJ \cdot cm^{-2} \cdot Pulse^{-1}$ can be adopted. The upper limit of the pressure in the chamber can be set at $5\times10^{-4}$ Pa and the lower limit is preferably $1\times10^{-9}$ Pa.

Clusters (grains) as large as several 10 nm are sometimes formed during film formation or doping and they are inevitably deposited onto the substrate. Such clusters (grains) are causative of failure as point defects. By making use of the fact that the force applied to charge particles passing through an electrostatic field or magnetostatic field depends on the mass and charge, grading by mass is performed, whereby only small-size metal clusters can be deposited. The upper limit of the cluster size is preferably 100 nm, more preferably 20 nm, particularly preferably 6 nm, while the lower limit is preferably 0.1 nm.

For example, after grading by mass is performed using a quadrupole deflector in combination with any of an electrostatic mass spectrometer, magnetostatic mass spectrometer, double-focusing mass spectrometer, and time-of-flight mass spectrometer or using a quadrupole mass filter, a ultrathin metal film may be formed on a substrate. The direction of ion beam may be bent using a quadrupole deflector. It is also possible to select a certain size of clusters by using a potential switch and deposit them on the surface.

The cluster ion is preferably deposited on the surface with energy as small as possible. The ion may be decelerated by exposing the electrode surface of the substrate to a flow of an active gas (oxygen, hydrogen, nitrogen or fluorine) in advance in a deposition chamber and then placing a decelerating electrode plate (to apply a decelerating voltage while synchronizing with a pulse laser) in an ion channel connecting a cluster production chamber to a vapor deposition chamber. When the cluster ion cannot be decelerated fully, the impact of clusters colliding with the substrate can be reduced by inclining the substrate. When the clusters do not have adequate strength, a cluster beam may be converged using an Einzel lens or the like.

Confirmation Method of Layer Structure

The structure of each of the organic semiconductor device and organic electroluminescence device of the invention is analyzed by forming a thin film of the cross-section of a thin layer, for example, by a focused ion beam system (FIB, "FB-2000", trade name, product of Hitachi Ltd.), observing the resulting thin film through a transmission electron microscopy (TEM-EDX, "H-8100", trade name; product of Hitachi Ltd.) and analyzing its metal elements by X-ray analysis. Its cross-section can be confirmed by the observation through a scanning electron microscopy (SEM, "S-5000H", trade name; product of Hitachi, Ltd.) instead of TEM.

The invention will be described in further detail by Examples and Comparative Examples. These examples are not intended to be limiting but rather exemplary. In all the below-described designations, "wt. %" means "mass %".

(1) SYNTHESIS METHOD IN EXAMPLES

It is the common practice to synthesize the tertiary amine compound of the invention by coupling of 4,4'-dihalogeno-biphenyl and raw materials in accordance with the Heck reaction.

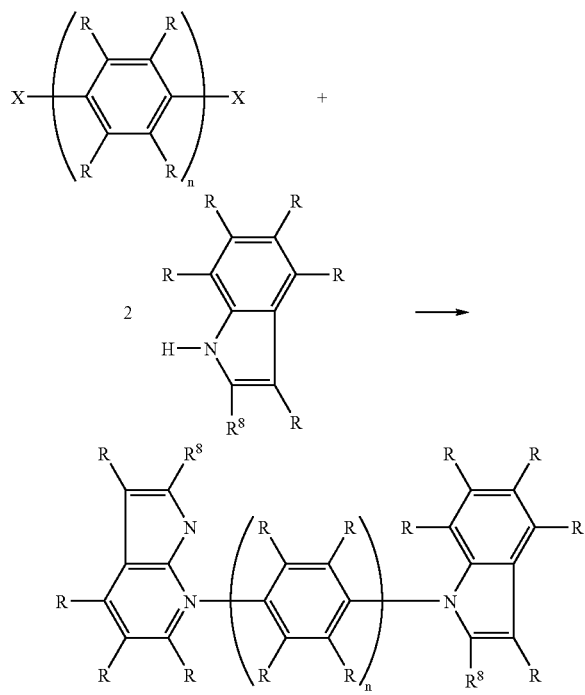

In the above formula, X represents a halogen atom, more specifically chlorine, bromine or iodine, n stands for an integer of from 1 to 6, $R^8$ represents a group composed of an aromatic cyclic compound and/or heterocyclic compound, preferably 1-naphthyl, 2-naphthyl or phenyl, especially preferably 1-naphtyl or 2-naphtyl, and the indole ring is connected to the conjugated system (without this connection, the compound does not exhibit desired performance).

Common Synthesis Method

A catalyst and phosphine were dissolved in a solvent used during reaction. To the resulting solution were added 4,4'-dihalogenobiphenyl, indole derivative and base, followed heating under reflux at an optimum temperature in a nitrogen atmosphere for a time necessary for completion of the reaction. A washing solvent was then added to the reaction mixture and the mixture was filtered. The organic layer was extracted and dried over magnesium sulfate. The solvent was distilled off under reduced pressure, whereby the desired compound was obtained as a crude product. The crude compound was purified by suitable chromatography and/or recrystallization. It was confirmed by NMR and infrared absorption spectrum that the resulting compound was the desired one.

(1) Kind of Catalyst

Examples of a palladium catalyst used in the synthesis include palladium acetate, tris(dibenzylideneacetone)dipalladium [which will hereinafter be referred to as "$Pd_2(DBA)_3$"] and palladium chloride. Of these, palladium acetate is preferred. The using amount of the palladium carbon is usually from 1 to 20 mole %, preferably from 1 to 13 mole %, more preferably from 2 to 6 mole % per mole of the indole derivative.

(1.1) Kind of Dihalogenobiphenyl (n=2)

Specific examples of the 4,4'-dihalogenobiphenyl of the above-described formula in which n=2 include, but not limited to, 4,4'-dibromobiphenyl, 4,4'-diiodobiphenyl and 4-bromo-4'-iodobiphenyl.

The 4,4'-dihalogenobiphenyl is usually added in an amount of from 0.1 to 1 mole, preferably from 0.4 to 0.6 mole per mole of the indole derivative.

(1.2) A Phosphorous Compound Such as Tertiary Phosphate or Phosphine Complex.

Examples of the phosphine used in the above reaction include 2,2'-bis(diphenylphosphino)-1,1'-binaphthyl (BINAP), 1,1'-bis(diphenylphosphino)ferrocene (DPPF), dicyclohexylphosphinobiphenyl, di-t-butylphosphinobiphenyl and tri-t-butylphosphine. Of these, tri-t-butylphosphine is preferred. The phosphine is usually added in an amount of from 3 to 15 mole %, preferably from 6 to 10 mole % per mole of the indole derivative.

(1.3) Kind of Base

Alkoxy potassiums and alkoxy sodiums are usable as the base. Examples of the alkoxy group include alkoxy groups having a linear or branched $C_{1-6}$ aliphatic hydrocarbon residue such as methoxy, ethoxy, n-propoxy, isopropopxy, n-butoxy, t-butoxy, n-pentyloxy, and n-hexyloxy groups. Of these, t-butoxy group is especially preferred. The base is usually added in an amount of from 1 to 5 equivalents, preferably from 2 to 3 equivalents to 1 mole of the indole derivative.

(2) Solvent Used During Reaction

As the solvent used during the Heck reaction, aromatic hydrocarbon solvents such as benzene, toluene and xylene can be used. Of these, xylene and toluene are preferred, with dehydrated xylene being especially preferred. The solvent is usually added in an amount of from 1 to 35 parts by weight based on 1 part by weight of the indole derivative.

(3) Reaction Temperature

The reaction temperature usually falls within a range of from 50 to 150° C., preferably from 70 to 130° C. A molecule having a greater steric hindrance to the NH portion of the indole requires higher temperature.

(4) Reaction Time

The reaction time is usually from 1 to 80 hours, preferably from 1 to 24 hours. A raw material having a greater steric hindrance to the NH portion of the indole requires a longer reaction time.

(5) Isolation and Purification

After the completion of the reaction, the reaction mixture is subjected to extraction, concentration, decoloration, drying, recrystallization or the like to isolate the tertiary amine compound of the invention in the crude form.

(5.1) Solvents for Washing and Extraction

Water can be used as a washing solvent, while chloroform, ethyl acetate or tetrahydrofuran can be used as an extraction solvent. A plurality of these solvents may be used in combination. The organic layer obtained by extraction may be washed further and at this time, water, a saturated aqueous solution of sodium chloride or a saturated aqueous solution of sodium bicarbonate can be used as the washing solvent.

(5.2) Solvent for Column Chromatography

Examples of the solvent include chloroform, hexane, toluene, xylene and ethyl acetate. These solvents may be used in combination.

(6) Recrystallization

After the crude desired compound is dissolved in a solvent, the resulting solution is recrystallized by any of the following three methods:

1) by precipitating crystals while making use of a difference in solubility of the solution depending on the temperature of the solution, 2) by precipitating crystals while concentrating the solution by distilling off the solvent, and 3) by precipitating crystals while adding another solvent to the solution and/or adding dropwise the solution to another solvent to lower the solubility. The desired compound is available by any of these methods.

(6.1)

Examples of the compound used as a solvent for dissolving and purifying the crude tertiary amine compound of the invention include $C_{1-2}$ aliphatic halides, amides and dimethylsulfoxide.

(6.2)

Examples of the $C_{1-2}$ aliphatic halides include dichloromethane, chloroform, 1,2-dichloroethane, 1,1-dichlorethane, and 1,1,1-trichloroethane, while those of the amides include dimethylformamide and dimethylacetamide.

(6.3)

Examples of the compound used as a solvent for precipitating crystals of the tertiary amine compound of the invention (the tertiary amine compound of the invention has a lower solubility) from the solution of the crude tertiary amine compound of the invention include alcohols, ethers, ketones, aromatic hydrocarbons and aliphatic hydrocarbons.

(6.4)

Specific examples of the alcohols include methanol, ethanol, n-propyl alcohol, 2-propanol, isopropyl alcohol, n-butyl alcohol and t-butyl alcohol; those of the ethers include dimethoxyethane, tetrahydrofuran, 1,4-dioxane and diethyl ether; those of the ketones include acetone and methyl ethyl ketone; those of the aromatic hydrocarbons include benzene, toluene and xylene; and those of the aliphatic hydrocarbons include pentane, hexane, methylcyclohexane and heptane.

(6.5)

Although no particular limitation is imposed on the amount of the solvent used for dissolving therein the crude tertiary amine compound of the invention, it is usually from 5 to 100 parts by weight, preferably from 30 to 70 parts by weight based on 1 part by weight of the tertiary amine compound of the invention.

(6.6)

The amount of the solvent used for precipitation of crystals is from 100 to 300 parts by weight, preferably from 150 to 250 parts by weight based on 1 part by weight of the tertiary amine compound of the invention.

Intermediates which will be raw materials, that is, 2-phenylindole, 2-(1-naphthyl)indole, and 2-(2-naphthyl)indole can be obtained or synthesized as described below.

1. How to Obtain These Raw Materials

In Japan, the raw materials 2-phenylindole and 2-(2-naphthyl)indole are commercially available as products of Alfa Aesar-Johnson Matthey Japan Incorporated. According to the 2003-2004 catalogue of Organics Inorganics Metals Materials, 2-phenylindole corresponds to CAS No. 753463-59-1 and Stock No. B23674 or B25045 and 2-(2-naphthyl)indole corresponds to CAS No. 23746-81-8 and Stock No. B20434 so that they are easily available. The synthesis method of 2-(1-naphthyl) indole was described in such as CAS No. 76902-25-1 or Robert L. Hudkins, James L. Diebold, and Frank D. Marsh, J. Org. Chem., 60(19), 6218~20(1995). The indole derivative, that is, an intermediate used in the invention can be readily synthesized making use of the existing synthesis method.

2. Synthesis Method

Examples of the synthesis method of an indole derivative include Reissert synthesis, Gassman synthesis, Madelung synthesis, McMurry synthesis, Bischler synthesis, Fischer synthesis, synthesis using copper acetylide (for example, refer to "C. E. Castro, E. J. Gaughan, and D. C. Owsley, *J. Org. Chem.*, 31, 4071(1996)), and synthesis utilizing a coupling reaction in the presence of a palladium catalyst (for example, refer to A. Arcadi, S. Cacchi, and F. Marinelli, *Tetrahedron Letters*, 30, 2581(1989), a synthesis method without eliminating the protecting group from a NH group in *Pharm. Bull.*, 36, 1305(1988), or a method of eliminating a protecting group in *Tetrahedron Letters*, 39, 595(1988) or Sharada. S. Labadie and Edmond Teng, J. Org. Chem., 59, 4250(1994)).

Synthesis example 1

In 50 mL of dehydrated xylene were dissolved 0.04 g of palladium acetate and 0.12 g of tri-t-butylphosphine. To the resulting solution were added 0.90 g of 4,4-dibromobiphenyl, 1.40 g of 2-(2-naphthyl)indole and 0.65 g of sodium-t-butoxide, followed by heating under reflux at 125° C. for 24 hours in a nitrogen atmosphere. Chloroform and water were added to the reaction mixture and the resulting mixture was filtered. After the organic layer thus extracted was dried over magnesium sulfate, the solvent was distilled off under reduced pressure to give 0.70 g of a desired compound represented by the formula (142) in the crude form. The resulting compound was purified by column chromatography using a 1:1 chloroform and n-hexane mixture, followed by recrystallization from methanol to give 0.51 g of the desired compound represented by the formula (142). Nuclear magnetic resonance [$^1$H-NMR] (solvent: $CDCl_3$, internal standard: tetramethylsilane) and infrared absorption spectrum ([IR] (KBR pellet) were conducted to confirm that the compound was the desired compound. The NMR chemical shift was: δ7.96-7.63(m, 6H), 7.59-7.03(m, 24H), 6.79 (m, 2H). The IR absorption peaks were located at 3056 $cm^{-1}$, 1604 $cm^{-1}$, 1481 $cm^{-1}$, 1340 $cm^{-1}$, 1305 $cm^{-1}$, 1000 $cm^{-1}$, 905 $cm^{-1}$, 858 $cm^{-1}$, 808 $cm^{-1}$ and 740 $cm^{-1}$.

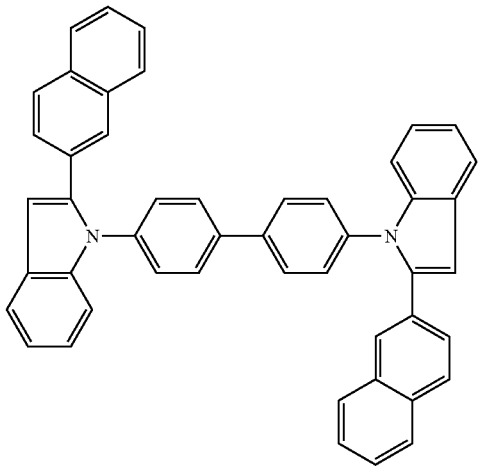

(142)

The tertiary amine compounds of the invention used in the below-described examples can also be synthesized in a manner similar to the above-described one. In addition, various tertiary amine compounds of the invention cay be synthesized. For example, they can be synthesized using, instead of 2-(2-naphthyl)indole, 5-(2-naphthyl)pyrrolo[2,3-b]pyridine, 5-(1-naphthyl)pyrrolo[2,3-b]pyridine, 5-(2-naphthyl)pyrrolo[3,2-b]pyridine, 5-(1-naphthyl)pyrrolo[3,2-b]pyridine, 2-phenylindol-3-acetonitrile, 2-phenylindol-3-carboxyaldehyde, 2-(2-naphthyl)indole, 2-(1-naphthyl)indole, 2-phenylindole, 2-(2-naphthyl)imidazole, 2-(1-naphthyl)imidazole, 2-phenylimidazole, 2-(2-naphthyl)-1H-indazole, 2-(1-naphthyl)-1H-indazole, 2-phenyl-1H-indazole or 1H-perimidine.

Synthesis Example 2

In 50 mL of dehydrated xylene were dissolved 0.04 g of palladium acetate and 0.12 g of tri-t-butylphosphine. To the resulting solution were added 0.90 g of 4,4-dibromobiphenyl, 1.40 g of 2-(1-naphthyl)indole and 0.65 g of sodium-t-butoxide, followed by heating under reflux at 130° C. for 32 hours in a nitrogen atmosphere. Chloroform and water were added to the reaction mixture and the resulting mixture was filtered. After the organic layer thus extracted was dried over magnesium sulfate, the solvent was distilled off under reduced pressure to give 0.74 g of a desired compound represented by the formula (143) in the crude form. The resulting crude compound was purified by column chromatography using a 1:1 chloroform and n-hexane mixture, followed by recrystallization from methanol to give 0.57 g of the desired compound represented by the formula (143). Nuclear magnetic resonance [$^1$H-NMR] (solvent: CDCl$_3$, internal standard: tetramethylsilane) and infrared absorption spectrum ([IR] (KBR pellet) were conducted to confirm that the compound was the desired compound. NMR chemical shift: δ8.12(d, 2H), 7.91-7.71(m, 4H), 7.65-7.06(m, 24H), 6.71(m, 2H). IR absorption peaks: at 3056 cm$^{-1}$, 1602 cm$^{-1}$, 1481 cm$^{-1}$, 1340 cm$^{-1}$, 1305 cm$^{-1}$, 1000 cm$^{-1}$, 917 cm$^{-1}$, 902 cm$^{-1}$, 795 cm$^{-1}$, 740 cm$^{-1}$.

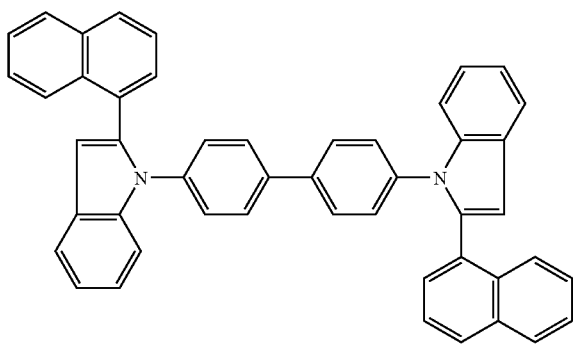

(143)

Synthesis Example 3

In 50 mL of dehydrated xylene were dissolved 0.04 g of palladium acetate and 0.12 g of tri-t-butylphosphine. To the resulting solution were added 0.90 g of 4,4-dibromobiphenyl, 1.11 g of 2-phenylindole and 0.65 g of sodium-t-butoxide, followed by heating under reflux at 120° C. for 20 hours in a nitrogen atmosphere. Chloroform and water were added to the reaction mixture and the resulting mixture was filtered. After the organic layer was extracted and dried over magnesium sulfate, the solvent was distilled off under reduced pressure to give 0.62 g of a desired compound represented by the formula (144) in the crude form. The resulting crude compound was purified by column chromatography using a 1:1 chloroform and n-hexane mixture, followed by recrystallization from methanol to give 0.44 g of the desired compound represented by the formula (144). Nuclear magnetic resonance [$^1$H-NMR] (solvent: CDCl$_3$, internal standard: tetramethylsilane) and infrared absorption spectrum ([IR] (KBR pellet) were conducted to confirm that the compound was the desired compound. The NMR chemical shifts: δ7.69-6.96(m, 26H), 6.83(m, 2H). IR absorption peaks: at 3049 cm$^{-1}$, 1600 cm$^{-1}$, 1480 cm$^{-1}$, 1340 cm$^{-1}$, 1305 cm$^{-1}$, 1000 cm$^{-1}$, 917 cm$^{-1}$, 902 cm$^{-1}$, 740 cm$^{-1}$, 695 cm$^{-1}$.

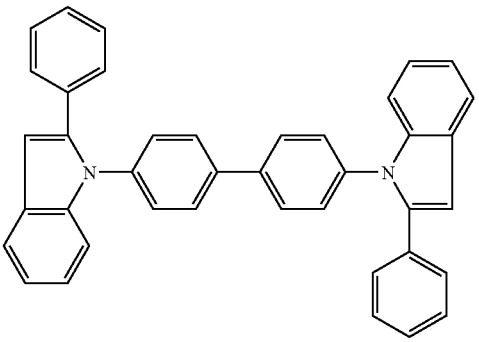

(144)

Figure 2:
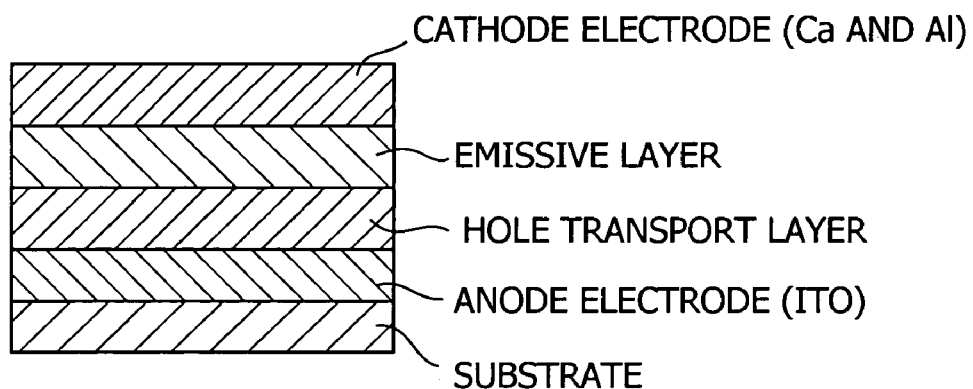
FIG. 2 is a cross-sectional view illustrating one example of the organic electroluminescence device (bottom emission type) of the invention.
Figure 3:
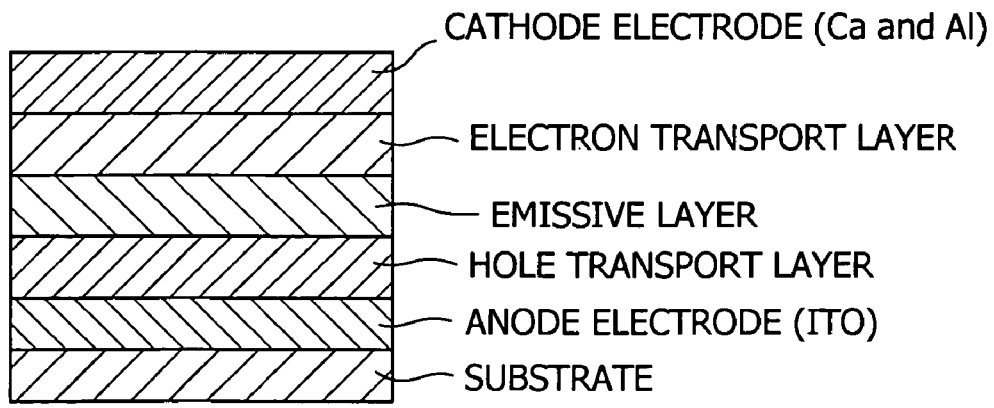
FIG. 3 is a cross-sectional view illustrating one example of the organic electroluminescence device (bottom emission type) of the invention.

In Examples 1 to 3 and Comparative Example 1, an organic semiconductor device having a cross-sectional structure as illustrated in FIG. 1 was used. In Example 4, an organic electroluminescence device having a cross-sectional structure as illustrated in FIG. 2 was used. In Example 5, an organic electroluminescence device having a cross-sectional structure as illustrated in FIG. 3 was used.

Example 1

Chromium was sputtered (film thickness of Cr: 400 Å) on an oxidized silicon wafer serving as a substrate to form a gate electrode and then SiO$_2$ was formed (film thickness: 150 nm) as a gate insulating layer on the gate electrode. A pair of chromium electrodes was formed on the gate insulating layer as a source electrode and a drain electrode and then, gold was coated on the surfaces thereof (electrodes in a 2 mm×4 mm rectangular shape, film thickness of Au: 300 Å, film thickness of Cr: 400 Å). The distance between the source electrode and the drain electrode was set to 6 μm. The tertiary amine compound obtained in Synthesis Example 1 was deposited via mask in a vacuum bell jar of 10$^{-3}$ Pa by vapor deposition to form a semiconductor layer composed of the tertiary amine compound and having a thickness of 0.5 μm. The organic semiconductor device as illustrated in FIG. 1 was thus fabricated.

Example 2

Chromium was sputtered (film thickness of Cr: 400 Å) on an oxidized silicon wafer serving as a substrate to form a gate electrode and then SiO$_2$ was formed (film thickness: 150 nm) as a gate insulating layer on the gate electrode. A pair of chromium electrodes were formed on the gate insulating layer as a source electrode and a drain electrode, and then gold was coated on the upper surface thereof (electrodes in a 2 mm×4 mm rectangular shape, film thickness of Au: 300 Å, film thickness of Cr: 400 Å). The distance between the source electrode and the drain electrode was set to 6 μm. The tertiary amine compound obtained in Synthesis Example 2 was deposited via mask in a vacuum bell jar of $10^{-3}$ Pa by vapor deposition to form a semiconductor layer composed of the tertiary amine compound and having a thickness of 0.5 μm. The organic semiconductor device as illustrated in FIG. 1 was thus fabricated.

Example 3

Chromium was sputtered (film thickness of Cr: 400 Å) on an oxidized silicon wafer serving as a substrate to form a gate electrode and then $SiO_2$ was formed (film thickness: 150 nm) as a gate insulating layer on the gate electrode. A pair of chromium electrodes was formed on the gate insulating layer as a source electrode and a drain electrode, and then gold was coated on the upper surface thereof (electrodes in a 2 mm×4 mm rectangular shape, film thickness of Au: 300 Å, film thickness of Cr: 400 Å). The distance between the source electrode and the drain electrode was set to 6 μm. An alignment layer was then formed between the source electrode and drain electrode over the resulting substrate by oblique deposition of SiO by CVD. The temperature of the evaporation source was 1800K and the minimum deposition angle was 85°. The tertiary amine compound obtained in Synthesis Example 3 was deposited in a vacuum bell jar of $10^{-3}$ Pa by vapor deposition to form a semiconductor layer composed of the tertiary amine compound and having a thickness of 0.5 μm. The organic semiconductor device as illustrated in FIG. 1 was thus fabricated.

Example 4

An organic electroluminescence device was fabricated by forming, on a glass substrate having the pattern of an ITO electrode formed as an anode electrode, a hole transport layer (film thickness: 50 nm) using the tertiary amine compound obtained in Synthesis Example 1, an emissive layer (film thickness: 40 nm) using Alq$_3$ {tris(8-hydroxychinolinato)-aluminum, a cathode electrode (film thickness: 10 nm) using Ca and an Al layer (film thickness: 200 nm) thereon by vacuum deposition. As a result, the electroluminescence device thus obtained had improved breakdown voltage and longer life {initial brightness at an applied voltage of 10V: 5000 cd/m², luminous efficiency: 0.51 m/W, half brightness time: 60000 hours; in the case where α-NPD was used as a hole transport layer instead of the tertiary amine compound of the invention, initial brightness at an applied voltage of 10V: 1000 cd/m², luminous efficiency: 1.21 m/W, half brightness time: 10000 hours).

Example 5

An organic electroluminescence device was fabricated by forming, on a glass substrate having the pattern of an ITO electrode formed as an anode electrode, α-NPD (film thickness: 50 nm) as a hole transport layer, Ir(ppy)$_3$ {tris-(phenylpyridyl)-iridium} as a guest of an emissive layer, the tertiary amine compound (film thickness: 40 nm, amounting to about 93% of the host of the emissive layer, co-deposition) of the invention obtained in Synthesis Example 1 as a host of the emissive layer, Alq$_3$ {film thickness: 40 nm) as an electron transport layer, Ca (10 nm) as a cathode electrode and an Al layer (film thickness: 200 nm) as an upper layer of the Ca layer by vacuum deposition. As a result, the electroluminescence device thus obtained had improved breakdown voltage and longer life {initial brightness at an applied voltage of 10V: 600 cd/m², luminous efficiency: 0.51 m/W, half brightness time: 500 hours; in the case where CBP {4,4'-bis(carbazol-9-yl)biphenyl} was used as a host of the emissive layer instead of the tertiary amine compound of the invention, initial brightness at an applied voltage of 10V: 300 cd/m², luminous efficiency: 0.91 m/W, half brightness time: 20 hours}.

Example 6

Stacking of a Surface Modification Layer on Electrodes of an Organic Semiconductor Device Chromium (film thickness of Cr: 400 Å) was sputtered on an oxidized silicon wafer serving as a substrate to form a gate electrode. On the gate electrode, an $SiO_2$ layer was formed as a gate insulating layer (film thickness: 150 nm). A pair of chromium electrodes was formed thereon as a source electrode and a drain electrode and the upper surface of them was coated with PtCo as a surface modification layer to give a thickness of 2 nm (the electrodes in a 2 mm×4 mm rectangular shape, film thickness of PtCo: 15 Å, film thickness of Cr: 700 Å). The distance between the source electrode and drain electrode was set at 6 μm.

The surface modification layer was formed using a laser sputtering apparatus. The pressure in a cluster growth chamber was $3\times10^{-4}$ Pa. Laser was focused to a target by using, as an oscillator of a pulse laser, a frequency-doubled (532 nm) Q-switched Nd:YAG laser ("DCR-11", trade name; product of Spectra Physics) while rotating and translating the target. The target was exposed to the pulse laser with a pulse width of 30 ns and ablated. The repetition frequency of the laser was set to 10 Hz. As the target, a PtCo alloy was employed. The method relating to the growth of clusters is described in J. P. Bucher, Rev. Sci. Instrum. 63, 5667(1992) or the like.

Between the source electrode and drain electrode formed over the substrate in the above-described manner, SiO was obliquely deposited by CVD as an alignment layer. The temperature of the evaporation source was 1800K and the minimum deposition angle was 85°. A semiconductor layer of 0.5 μm thick composed of the tertiary amine compound was then formed by depositing pentacene (product of Aldrich) by vapor deposition in a vacuum bell jar of $10^{-3}$ Pa. The organic semiconductor device as illustrated in FIG. 1 was thus fabricated.

Example 7

Stacking of a Surface Modification Layer on Electrodes of an Organic Semiconductor Device Chromium (film thickness of Cr: 400 Å) was sputtered on an oxidized silicon wafer serving as a substrate to form a gate electrode. On the gate electrode, an $SiO_2$ layer was formed as a gate insulating layer (film thickness: 150 nm). A pair of chromium electrodes was formed thereon as a source electrode and a drain electrode and then, the upper surface of them was coated with PtCo as a surface modification layer to give a thickness of 2 nm (the electrodes in a 2 mm×4 mm rectangular shape, film thickness of PtCo: 15 Å, film thickness of Cr: 700 Å) in a similar manner to that employed in Example 6. The distance between the source electrode and drain electrode was set at 6 μm.

Between the source electrode and drain electrode formed over the substrate in the above-described manner, SiO was obliquely deposited by CVD as an alignment layer. The temperature of the evaporation source was 1800K and the minimum deposition angle was 85°. A semiconductor layer of 0.5 μm thick composed of the tertiary amine compound of the invention obtained in Synthesis Example 1 was then formed by depositing the tertiary amine compound by vapor deposition in a vacuum bell jar of $10^{-3}$ Pa. The organic semiconductor device as illustrated in FIG. 1 was thus fabricated.

Comparative Example 1

No Stacking of a Surface Modification Layer Over the Electrode of an Organic Semiconductor Device In a bottom-gate type organic semiconductor device, an $SiO_2$ film was formed to give a thickness of 300 nm on an oxidized silicon wafer by CVD. Chromium was sputtered to form a gate electrode (film thickness of Cr: 400 Å) and on the gate electrode, $SiO_2$ was formed as a gate insulating layer (film thickness: 150 nm). A pair of chromium electrodes was formed thereon as a source electrode and a drain electrode, and then the upper surface thereof was coated with gold (electrode in a 2 mm×4 mm rectangular shape, film thickness of Au: 300 Å, film thickness of Cr: 400 Å). The distance between the source electrode and drain electrode was set to 6 μm. A 0.5 μm-thick semiconductor layer composed of pentacene was then formed by depositing pentacene (product of Aldrich) via a mask in a vacuum bell jar of $10^{-3}$ Pa by vapor deposition.

The tertiary amine compound of the invention can be identified by dissolving a semiconductor layer in a solvent such as toluene, obtaining a remaining compound by recrystallization, distillation under reduced pressure, natural drying and/or Soxhlet extraction and then subjecting it to elemental analysis. It is also possible to dissolve the semiconductor layer in a solvent such as toluene, drying the solution, and then purifying the remaining compound by sublimation purification.

Comparative Example 2

No Stacking of a Surface Modification Layer Over the Electrode of an Organic Semiconductor Device In a bottom-gate type organic semiconductor device, an $SiO_2$ film was formed to give a thickness of 300 nm on an oxidized silicon wafer by CVD. Chromium was sputtered to form a gate electrode (film thickness of Cr: 400 Å) and on the gate electrode, $SiO_2$ was formed as a gate insulating layer (film thickness: 150 nm). A pair of chromium electrodes was formed thereon as a source electrode and a drain electrode, and then the upper surface thereof was coated with gold (electrode in a 2 mm×4 mm rectangular shape, film thickness of Au: 300 Å, film thickness of Cr: 400 Å). The distance between the source electrode and drain electrode was set to 6 μm. A 0.5-μm thick semiconductor layer composed of the tertiary amine compound of the invention obtained in Synthesis Example 1 was then formed by depositing the tertiary amine compound via a mask in a vacuum bell jar of $10^{-3}$ Pa by vapor deposition.

Evaluation Results

The organic semiconductor devices obtained in Examples 1 to 7 and Comparative Examples 1 and 2 were evaluated for resistivity, threshold voltage (Vth) and current ratio (Ion/Ioff), that is, a ratio of a current during gate voltage application to a current during no gate voltage application.

The resistivity of the tertiary amine compound was evaluated by ordinarily employed two-terminal measurement. It has already been revealed that the resistivity of the tertiary amine compound of the invention is relatively higher on a low voltage side (at $2.6 \times 10^5$ V/cm) than on a high voltage side (at $2 \times 10^6$ V/cm) and the resistivity decreases drastically with a certain voltage as a peak. The resistivity of the tertiary amine compound of the invention was evaluated based on three grades 1 to 3, 1 being resistivity of $10^{10}$ Ω·cm or greater but less than $10^{10}$ Ω·cm, 2 being resistivity of $10^8$ Ω·cm or greater but less than $10^{10}$ Ω·cm and 3 being resistivity of $10^4$ Ω·cm or greater but less than $10^8$ Ω·cm. The resistivity on a high voltage side ($2 \times 10^6$ V/cm) when the tertiary amine compounds (film thickness: about 50 nm) of the invention obtained in Examples 1 to 3 were used were evaluated as grades 3, 3, and 2, respectively, while that when pentacene was used as a semiconductor layer in Comparative Example 1 was evaluated as grade 1.

The tertiary amine compounds of the invention were evaluated for a current ratio (Ion/Ioff, that is, a current ratio of a current value (Ion) during voltage application of $2 \times 10^6$ V/cm to a current value (Ioff) during no voltage application) based on three grades 1 to 3, 1 being a current ratio of 0 or greater but less than $10^2$, 2 being that of $10^2$ or greater but less than $10^3$ and 3 being that of $10^3$ or greater but less than $10^4$. The current ratios on a high voltage side ($2 \times 10^6$ V/cm) when the tertiary amine compounds (film thickness: about 50 nm) of the invention obtained in Examples 1 to 7 were used were evaluated as grades 3, 3, 2, 3, 2, 2 and 3, respectively, while those in Comparative Example 1 and Comparative Example 2 were each evaluated as grade 1.

The tertiary amine compounds of the invention were evaluated for a threshold voltage (Vth) defined as a current value which will be 1/e of the ultimate current and it was evaluated based on three grades 1 to 3, 1 being a threshold voltage of 0 or greater but less than $10^2$, 2 being that of $10^2$ or greater but less than $10^3$ and 3 being that of $10^3$ or greater but less than $10^4$. The threshold voltage when the tertiary amine compounds (film thickness: about 50 nm) of the invention obtained in Examples 1 to 7 were used were evaluated as grades 3, 3, 2, 3, 2, 2 and 3, respectively, while those in Comparative Example 1 and Comparative Example 2 were each evaluated as grade 1.

The semiconductor layer constituting the organic semiconductor device of the invention brings about the above-described effects because of the following reasons.

The factor which causes deterioration in the reliability (lifetime) or performance of the organic semiconductor device is that a formed film using a low molecular weight substance such as pentacene derivative has a weak cohesive force, has many defects due to crystallization and becomes clouded with time.

The factor is not the moisture in the atmosphere because the solubility of pentacene in water is very low.

Paying attention to such points, the invention has been made. By using a tertiary amine compound which can easily be packed, the film thus obtained hardly causes a time-dependent change even influenced by electric field or heat and becomes stable. As a result, the lifetime of the organic semiconductor device can be extended.

Example 8

Figure 4:
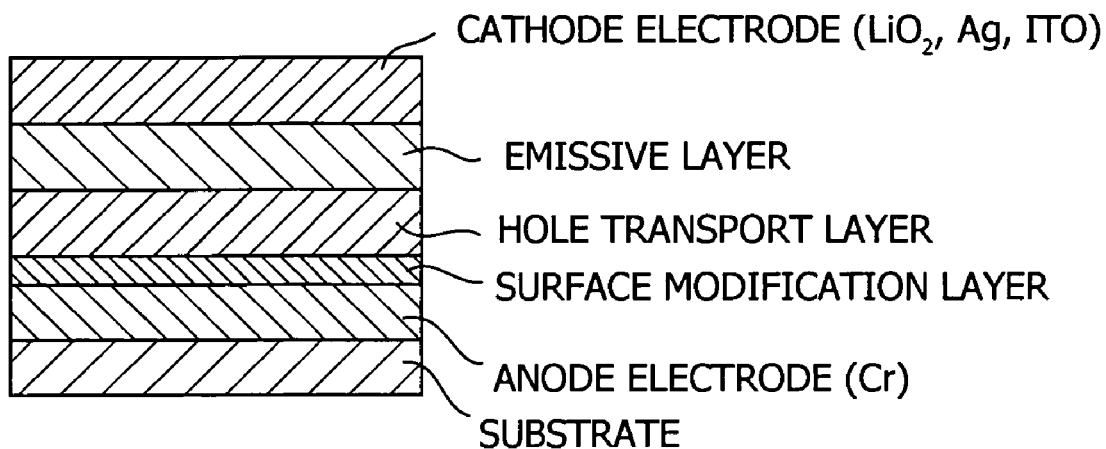
FIG. 4 is a cross-sectional view illustrating one example of the organic electroluminescence device (top emission type) of the invention.

Chromium was sputtered over a glass substrate by sputtering to form an anode electrode (film thickness of Cr: 400 Å), followed by application, onto the chromium electrode, of PtCo as a surface modification layer in a similar manner to Example 6 to give a film thickness of 2 nm (electrode in a 2 mm×4 mm rectangular shape, film thickness of PtCo: 15 Å, film thickness of Cr: 700 Å). A hole transport layer (film thickness: 50 nm) was formed thereon by using the tertiary amine compound of the invention obtained in Synthesis Example 1 by vapor deposition in a vacuum bell jar of $10^{-3}$ Pa. On the hole transport layer, $Alq_3$ (film thickness: 40 nm) was formed as an emissive layer. Then, as a cathode electrode, $LiO_2$ (film thickness: 1 nm), Ag (film thickness: 9 nm) and ITO (100 nm) were formed sequentially by ion plating, whereby a top emission type organic EL device having a cross-sectional structure as illustrated in FIG. 4 was formed. The organic electroluminescence device thus obtained had an initial brightness of 1200 cd/m² during voltage application of 10V, luminous efficiency of 0.61 m/W and half brightness time of 21000 hours.

Comparative Example 3

Figure 5:
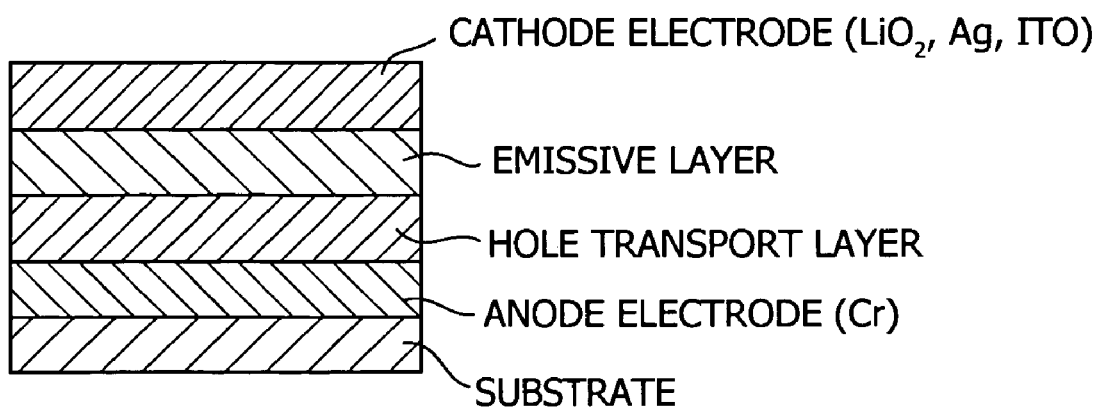
FIG. 5 is a cross-sectional view illustrating one example of the organic electroluminescence device (top emission type).

Chromium was sputtered on a glass substrate as an anode electrode (film thickness of Cr: 400 Å). A hole transport layer (film thickness: 50 nm) was formed thereon by using the tertiary amine compound of the invention obtained in Synthesis Example 1 by vapor deposition in a vacuum bell jar of $10^{-3}$ Pa. On the hole transport layer, $Alq_3$ (film thickness: 40 nm) was formed as an emissive layer. Then, as a cathode electrode, $LiO_2$ (film thickness: 1 nm), Ag (film thickness: 9 nm) and ITO (100 nm) were formed sequentially by ion plating, whereby a top emission type organic EL device having a cross-sectional structure as illustrated in FIG. 5 was fabricated. The organic electroluminescence device thus obtained had an initial brightness of 300 cd/m² during voltage application of 10V, luminous efficiency of 1.41 m/W and half brightness time of 6000 hours.

What is claimed is:

1. A tertiary amine compound represented by formula (1):

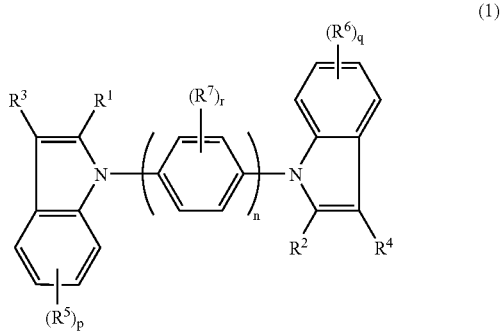

wherein n is an integer from 1 to 6; p, q and r each is an integer from 0 to 4; $R^1$ and $R^2$ each independendy represents a naphthyl group; $R^3$ and $R^4$ each independently represents a hydrogen atom or a $C_{1-20}$ alkyl group; and $R^5$, $R^6$ and $R^7$ each independently represents a $C_{1-20}$ alkyl group.

2. The tertiaiy amine compound of claim 1, wherein n is 2; p, q and r each is 0; $R^1$ and $R^2$ each represents a 2-naphthyl group; and $R^3$ and $R^4$ each represents a hydrogen atom.

3. The tertiary amine compound of claim 1, wherein n is 2; p, q and r each is 0; $R^1$ and $R^2$ each represents a 1-naphthyl group; and $R^3$ and $R^4$ each represents a hydrogen atom.

4. The tertiary amine compound of claim 1, wherein $R^1$ and $R^2$ each represents a 2-naphthyl group.

5. The tertiary amine compound of claim 1, wherein $R^1$ and $R^2$ each represents a 1-naphthyl group.

* * * * *

UNITED STATES PATENT AND TRADEMARK OFFICE
CERTIFICATE OF CORRECTION

PATENT NO. : 7,388,100 B2
APPLICATION NO. : 11/295925
DATED : June 17, 2008
INVENTOR(S) : Nishio It is certified that error appears in the above-identified patent and that said Letters Patent is hereby corrected as shown below:

On Title Page:
Foreign Application Priority Data, Item 30: Please add
-- JAPAN 2004-209725 07/16/2004 --

Abstract, Item 57, Line 11:    Please correct "comuound" to read -- compound --

Column 22, Lines 54 - 58:    Please correct formula 34 to read:

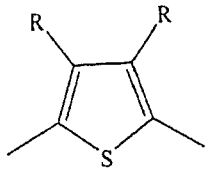

Column 61, Lines 19 - 28:    Please correct formula to read:

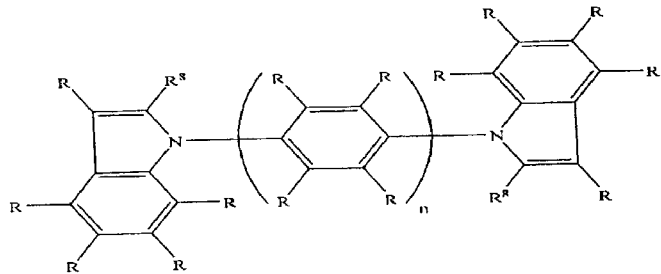

Column 72, Claim 2, Line 26:   Please correct "tertiaiy" to read -- tertiary --

Signed and Sealed this

Twenty-seventh Day of January, 2009

JOHN DOLL
*Acting Director of the United States Patent and Trademark Office*